(12) United States Patent
Lowsky et al.

(10) Patent No.: US 11,547,842 B2
(45) Date of Patent: *Jan. 10, 2023

(54) METHODS FOR CANCER TREATMENT

(71) Applicant: The Board of Trustees of the Leland Stanford Junior University, Stanford, CA (US)

(72) Inventors: Robert Lowsky, Stanford, CA (US); Edgar George Engleman, Atherton, CA (US); Samuel Strober, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 327 days.

This patent is subject to a terminal disclaimer.

(21) Appl. No.: 16/716,102

(22) Filed: Dec. 16, 2019

(65) Prior Publication Data

US 2020/0164195 A1 May 28, 2020

Related U.S. Application Data

(63) Continuation of application No. 14/783,997, filed as application No. PCT/US2014/034485 on Apr. 17, 2014, now Pat. No. 10,549,082.

(60) Provisional application No. 61/847,380, filed on Jul. 17, 2013, provisional application No. 61/813,063, filed on Apr. 17, 2013.

(51) Int. Cl.

| | |
|---|---|
| *A61K 31/713* | (2006.01) |
| *A61K 41/00* | (2020.01) |
| *A61K 45/06* | (2006.01) |
| *A61N 1/30* | (2006.01) |
| *A61B 18/08* | (2006.01) |
| *A61N 7/00* | (2006.01) |
| *A61B 18/14* | (2006.01) |
| *C12N 15/117* | (2010.01) |
| *A61N 5/10* | (2006.01) |
| *A61B 18/00* | (2006.01) |
| *A61M 37/00* | (2006.01) |
| *A01K 67/027* | (2006.01) |

(52) U.S. Cl.
CPC ..... *A61M 37/0092* (2013.01); *A01K 67/0271* (2013.01); *A61K 31/713* (2013.01); *A61K 41/00* (2013.01); *A61K 45/06* (2013.01); *A61N 1/30* (2013.01); *A01K 2207/12* (2013.01); *A01K 2207/35* (2013.01); *A01K 2227/105* (2013.01); *A01K 2267/0331* (2013.01); *A61B 18/08* (2013.01); *A61B 18/14* (2013.01); *A61B 2018/00577* (2013.01); *A61M 2037/0007* (2013.01); *A61N 5/10* (2013.01); *A61N 7/00* (2013.01); *A61N 2005/1098* (2013.01); *C12N 15/117* (2013.01); *C12N 2310/17* (2013.01); *C12N 2310/315* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 9,504,715 B2 | 11/2016 | Strober et al. | |
| 9,833,477 B2 | 12/2017 | Strober et al. | |
| 10,549,082 B2* | 2/2020 | Lowsky | ............ A61M 37/0092 |
| 2005/0215501 A1 | 9/2005 | Lipford et al. | |
| 2009/0082295 A1 | 3/2009 | Jungnelius et al. | |
| 2011/0212090 A1 | 9/2011 | Pederson et al. | |
| 2013/0261370 A1 | 10/2013 | Diaconescu et al. | |
| 2017/0014453 A1 | 1/2017 | Strober et al. | |

FOREIGN PATENT DOCUMENTS

WO    2011/068491    6/2011

OTHER PUBLICATIONS

Bregni et al. (Blood Jun. 1, 2002 99(11): 4234-4236) (Year: 2002).*
Brody et al. (J. Clin. Oncology Oct. 1, 2010, 28(28): 4324-4332) (Year: 2010).*
Childs et al. "Regression of Metastatic Renal-Cell Carcinoma after Nonmyeloablative, Allogeneic Peripheral-Blood Stem-Cell Transplantation," The New England Journal of Medicine, Sep. 14, 2000 (Sep. 14, 2000), vol. 343, No. 11, pp. 750-758.
Friedman, Eric. "Immune Modulation by Ionizing Radiation and its Implications for Cancer, Immunotherapy," Current Pharmaceutical Design, 2002, vol. 8, Iss.19, pp. 1765-1780.
Baron et al. (2006) "Chimerism and outcomes after allogeneic hematopoietic cell transplantation following nonmyeloablative conditioning".
Intraoperative radiation therapy (NCI Dictionary of Cancer Terms, https://www.cancer.gov/publications/dictionaries/cancer-terms/def/intraoperative-radiation-therapy, retrieved Mar. 5, 2019) (Year: 2019).
Stereotactic body radiation therapy (NCI Dictionary of Cancer Terms, https://www.cancer.gov/publications/dictionaries/cancer-terms/def/stereotactic-body-radiation-therapy, retrieved Mar. 5, 2019) (Year: 2019).
American Heritage Dictionary Entry: allogeneic (https://www.ahdictionary.com/word/search.html?q=allogeneic, obtained Jun. 4, 2018) (Year: 2018).
Chimera 1 Definition of chimera in US English by Oxford Dictionaries (https://en.oxforddictionaries.com/definition/us/chimera, obtained Jun. 4, 2018) (Year: 2018).
Bio Rad (The T Cell Marker, CD3 Antigen and Antibodies, 2016).

* cited by examiner

*Primary Examiner* — Peter J Reddig
(74) *Attorney, Agent, or Firm* — Bozicevic, Field & Francis LLP; Pamela J. Sherwood

(57) ABSTRACT

Residual, refractory or relapsed cancer is treated by immunostimulation in the presence of allogeneic immune effector cells, optimally in combination with radiation therapy. The methods of the disclosure induce a systemic allogeneic anti-tumor immune response that results in tumor regression in untreated sites of disease, i.e. non-injected, non-irradiated, etc.

11 Claims, 3 Drawing Sheets

Specification includes a Sequence Listing.

METHODS FOR CANCER TREATMENT

CROSS-REFERENCE

This application claims benefit and is a Continuation of U.S. application Ser. No. 14/783,997, filed Oct. 12, 2015, issued as U.S. Pat. No. 10,549,082, which claims benefit of 371 International Application No. PCT/US2014/034485, filed Apr. 17, 2014, which claims the benefit of 61/813,063 filed on Apr. 17, 2013 and the benefit of 61/847,380 filed on Jul. 17, 2013 under 35 USC § 365.

INCORPORATION BY REFERENCE OF SEQUENCE LISTING

A Sequence Listing is provided herewith as a Sequence Listing text file, S13-016 STAN-1008CON Seq List created on Dec. 16, 2019 and having a size of 703 bytes. The contents of the Sequence Listing text file are incorporated herein by reference in their entirety.

BACKGROUND

Cytoreductive therapy and allogeneic bone marrow or blood stem cell transplantation (HCT) is a treatment strategy that utilizes the administration of anti-cancer drugs and/or radiation therapy for the purpose of killing cancer cells and transplantation of hematopoietic cells to "rescue" or restore bone marrow blood and immune cell production. There can be significant side-effects, but type and severity of the side effects are influenced by the degree of HLA matching between donor and recipient; the condition and age of the patient; the specific treatment regimen; and the degree of suppression of the immune system.

Graft-versus-host disease is a common complication of allogeneic stem cell transplant. In this reaction, lymphocytes from the donor attack cells in the body of the recipient, particularly in the skin, gastrointestinal tract and liver. Common symptoms of acute graft-versus-host disease are skin rashes, jaundice, liver disease and diarrhea. Graft-versus-host disease also increases a patient's susceptibility to infection. Graft-versus-host disease can develop within days or as long as 3 years after transplantation. Graft-versus-host disease can also have an anti-cancer effect because donor lymphocytes can kill cancer cells as well as normal cells. When donor lymphocytes kill cancer cells, it can be referred to as graft-versus-tumor effect.

For patients who do not achieve or sustain a complete response to primary therapy, stem cell rescue by allogeneic HCT is often the treatment of choice. Allogeneic HCT can be considered a treatment option for select patients, especially those who have bone marrow involvement or who have relapse of diagnosis after autologous HCT. Allogeneic HCT can induce prolonged remissions and even cure some patients with chemotherapy refractory disease. An important mechanism of cancer eradication comes from the recognition of residual host tumor cells by donor-derived immune cells contained in the donor graft; termed the graft versus tumor (GVT) effect. This concept was initially developed from studies that used T-cell-depleted donor grafts in which graft-versus-host disease (GVHD) was eliminated. Without donor T-cells, patients suffered a high incidence of disease recurrence.

The demonstration that donor immune-mediated mechanisms are critical in controlling residual disease challenged the concept that relatively toxic full-dose chemoradiation is required for cure following allogeneic HCT. Transplant regimens that use significantly lower doses of chemoradiation, termed reduced intensity conditioning (RIC), that at the same time remain sufficiently immune-ablative to allow full donor hematopoietic cell engraftment have shifted the burden of tumor eradication to GVT effects. In an effort to reduce GVHD without compromising GVT reactions, a model has been developed for clinical practice where patients who receive low-dose total lymphoid irradiation (TLI) combined with depletive T-cell antibodies (anti-thymocyte serum) are infused with donor grafts. The majority of patients developed sustained donor-derived hematopoiesis and had a very low incidence of acute GVHD and non-relapse mortality.

Irrespective of whether a full dose or RIC transplant approach is pursued, relapse and disease progression remain the single largest cause of treatment failure after allogeneic HCT. Disease relapse after allogeneic HCT portends a poor outcome as typically allogeneic HCT was performed as a "last effort" for cure. Patients who experience relapse of lymphoma after allogeneic HCT remain in a unique circumstance in that they have progressive host-derived lymphoma with mixed (5-95%) or complete (>95%) donor hematopoietic cell chimerism. In some settings the 3-year cumulative risk of relapse after transplantation is 37% for patients who achieve complete donor hematopoietic cell chimerism and 78% among patients with mixed donor chimerism.

Interventions to treat relapsed disease included chemotherapy and/or radiation therapy (RT), withdrawal of immunosuppression or donor lymphocyte infusion (DLI). Despite these interventions, overall survival from time of relapse at 5 years is poor. Salvage treatment with radiation to bulky or symptomatic sites with or without chemotherapy induced responses in the majority of patients (>50%), yet the responses were generally of short duration (<6 months). Alternatively, in the absence of GVHD, DLI can be given yet this strategy is often complicated by the subsequent development of severe GVHD.

SUMMARY

Methods are provided for the treatment of cancer, e.g. residual, refractory or relapsed cancer, by immunostimulation in the presence of allogeneic immune effector cells, optimally in combination with radiation therapy. Immune stimulants of interest include, without limitation, nucleotide immunostimulatory sequences (ISS), e.g. oligodeoxynucleotides (ODN) containing CpG that bind to the Toll-like receptor (TLR) 9 and activate dendritic cells and B-cells. Other potentiators of immune responses of interest include for example, anti-CTLA4, anti-PD1, GM-CSF, dendritic cells, and the like. In some aspects the immune stimulant is injected intratumorally, i.e. into at least one tumor nodule. The methods of the disclosure induce a systemic allogeneic immune response that results in tumor regression in untreated sites of disease, i.e. non-injected, non-irradiated, etc.

In some aspects, immunostimulation is performed concurrently with involved field radiation therapy. At least one tumor site is irradiated in such methods. Various radiation modalities can be used for this purpose, including radiofrequency ablation (RFA); light combined with a photosensitizer; X-rays, proton beam, gamma radiation; etc. Low dose RT can be selected, as a low dose is adequate to induce tumor cell death, does not affect the ability for patients to receive higher treatment doses to the same sites in the future and minimizes radiation-induced inhibition of DC function.

In other aspects a chemotherapeutic regimen is applied that results in the release of tumor cell specific antigens, e.g. doxorubicin, etc.

The methods of the disclosure exploit the ability of allogeneic immune cells to generate an anti-tumor response to HLA alloantigens expressed by the tumor, and can include a response to tumor specific antigens. Immunostimulation by the methods of the disclosure is performed on an individual who is a mixed or complete hematopoietic chimera, i.e. where at least about 5% of circulating leukocytes are allogeneic relative to the individual, for example where at least about 5% of the circulating CD3+ cells are allogeneic relative to the individual.

In some aspects the individual has been treated with an allogeneic HCT prior to the immunostimulatory treatment, e.g. at least about 1 month prior, at least about 3 months prior, at least about 6 months prior, or more. In other aspects the individual selected for treatment by the methods of the disclosure has not had a prior allogeneic HCT, but an allogeneic HCT is performed in combination with the methods of the disclosure.

In some aspects the cancer is a lymphoma, where the lymphoma can be HL or NHL. In other aspects the cancer is a leukemia or myeloma. In other aspects the cancer is a cutaneous T-cell lymphoma, e.g. mycosis fungoides. In other aspects the cancer is a non-hematolymphoid malignancy, including without limitation carcinomas, e.g. carcinoma, renal cell carcinoma, and the like.

In one aspect, the disclosure comprises a method of (i) identifying a patient having a residual, relapsed or refractory cancer, where the patient has had a prior allogeneic HCT and is chimeric with respect to donor type leukocytes; and (ii) intratumorally injecting an immunostimulant in combination with local irradiation at one or more tumor nodules to induce a systemic allogeneic anti-tumor immune response that results in tumor regression in untreated sites of disease.

In another aspect, the disclosure comprises a method of (i) identifying a patient having a residual, relapsed or refractory cancer; (ii) performing allogeneic HCT to achieve at least about 5% allogeneic leukocytes; and (iii) intratumorally injecting an immunostimulant in combination with local irradiation at one or more tumor nodules to induce a systemic allogeneic anti-tumor immune response that results in tumor regression in untreated sites of disease.

Another aspect of the present disclosure relates to the use of an immunostimulant in the manufacture of a medicament for the treatment of a residual, relapsed or refractory cancer, wherein the medicament is administered to a patient that is a mixed or full chimera in combination with local irradiation at one or more tumor nodules.

In one aspect, the disclosure comprises a method of treating cancer in a subject, the method comprising administering to the subject an immunostimulant in combination with irradiation, wherein said irradiation induces a systemic allogeneic anti-tumor T-cell immune response that results in tumor regression in untreated sites of disease, and wherein the subject has undergone bone marrow transplant prior to said administering.

In another aspect, the disclosure comprises a method of treating a cancer, the method comprising: (a) identifying a subject having the cancer where the subject is chimeric for allogeneic hematopoietic stem cells; and (b) intratumorally injecting an immunostimulant in combination with irradiation at a tumor nodule to induce an immune response resulting in tumor regression.

In yet another aspect, the disclosure comprises a method of treating residual, relapsed or refractory cancer, the method comprising: (a) identifying a subject having a residual, relapsed or refractory cancer where the patient is chimeric for allogeneic hematopoietic stem cells and has at least about 5% allogeneic type leukocytes; and (b) intratumorally injecting an immunostimulant in combination with involved field local irradiation at a tumor nodule to induce a systemic allogeneic anti-tumor immune response that results in tumor regression in untreated sites of disease.

Still another aspect of the present disclosure provides kits for treatment of residual, relapsed or refractory cancer. In one aspect, the kit includes an immunostimulant, e.g. ISS, in an amount sufficient to induce a systemic allogeneic anti-tumor immune response that results in tumor regression in untreated sites of disease when administered to a patient at one or more tumor nodules in combination with local irradiation, when administered to a patient comprising allogeneic leukocytes. The kit can also include a reagents for HLA typing leukocytes as part of a step of determining chimerism. The kit can also include allogeneic hematopoietic cells, e.g., allogeneic BMT, mobilized peripheral blood cells, cord blood cells, or hematopoietic cells derived from cultured stem/progenitor cells for inducing complete or mixed chimerism.

In another aspect, the kit can be for treating residual, relapsed or refractory cancer, the kit comprising: (a) an immunostimulant; (b) a means for administering involved field local irradiation to a tumor nodule of a subject; and (c) a set of instructions for administering the immunostimulant and the involved field radiation to the subject.

In yet another aspect, the kit can be for treating cancer, the kit comprising: (a) an immunostimulant; (b) a means for administering radiation to a tumor nodule of a subject; and (c) a set of instructions for administering the immunostimulant and the radiation to the subject.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative aspects, in which the principles of the disclosure are utilized, and the accompanying drawings of which:

DETAILED DESCRIPTION

Figure 1:
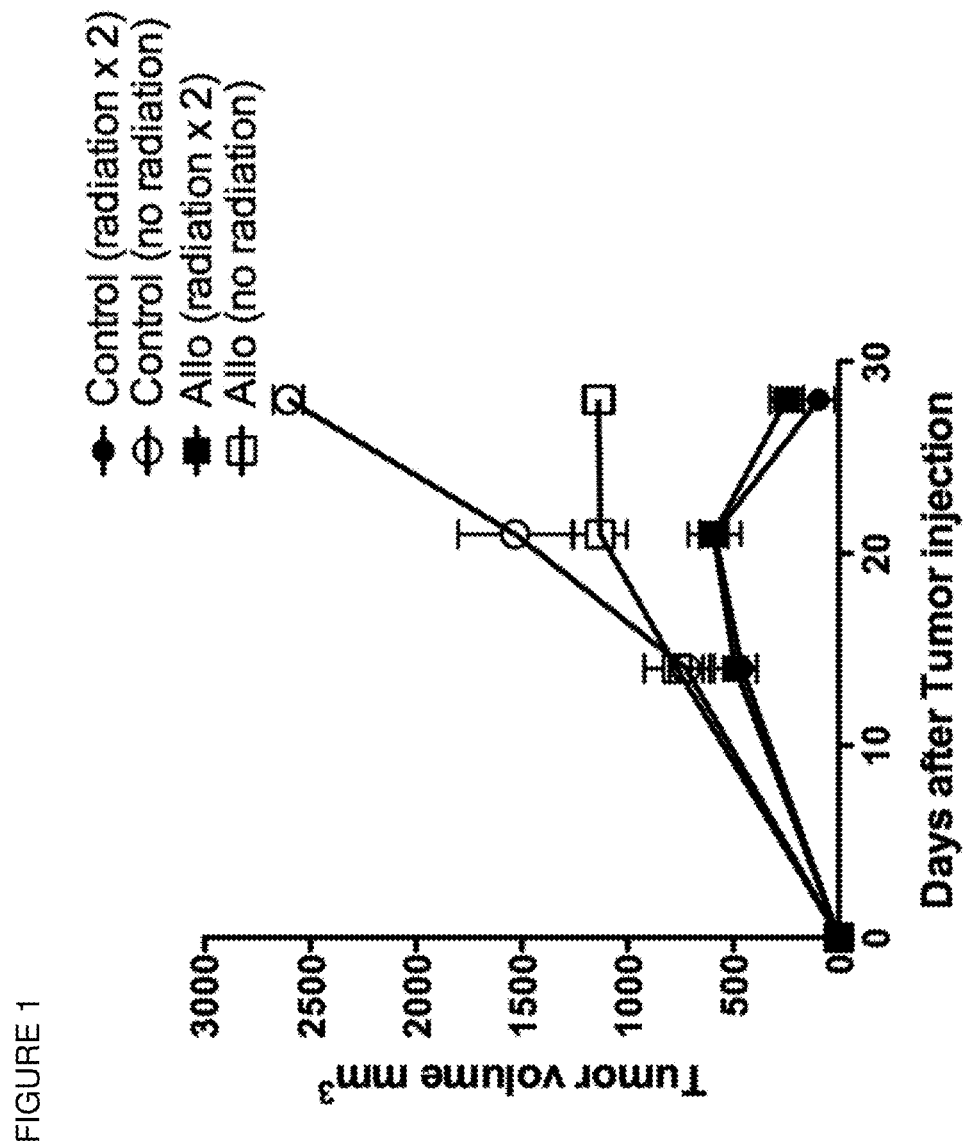
FIG. 1 depicts administration of CpG for lymphoma tumor relapse in mice.
Figure 2:
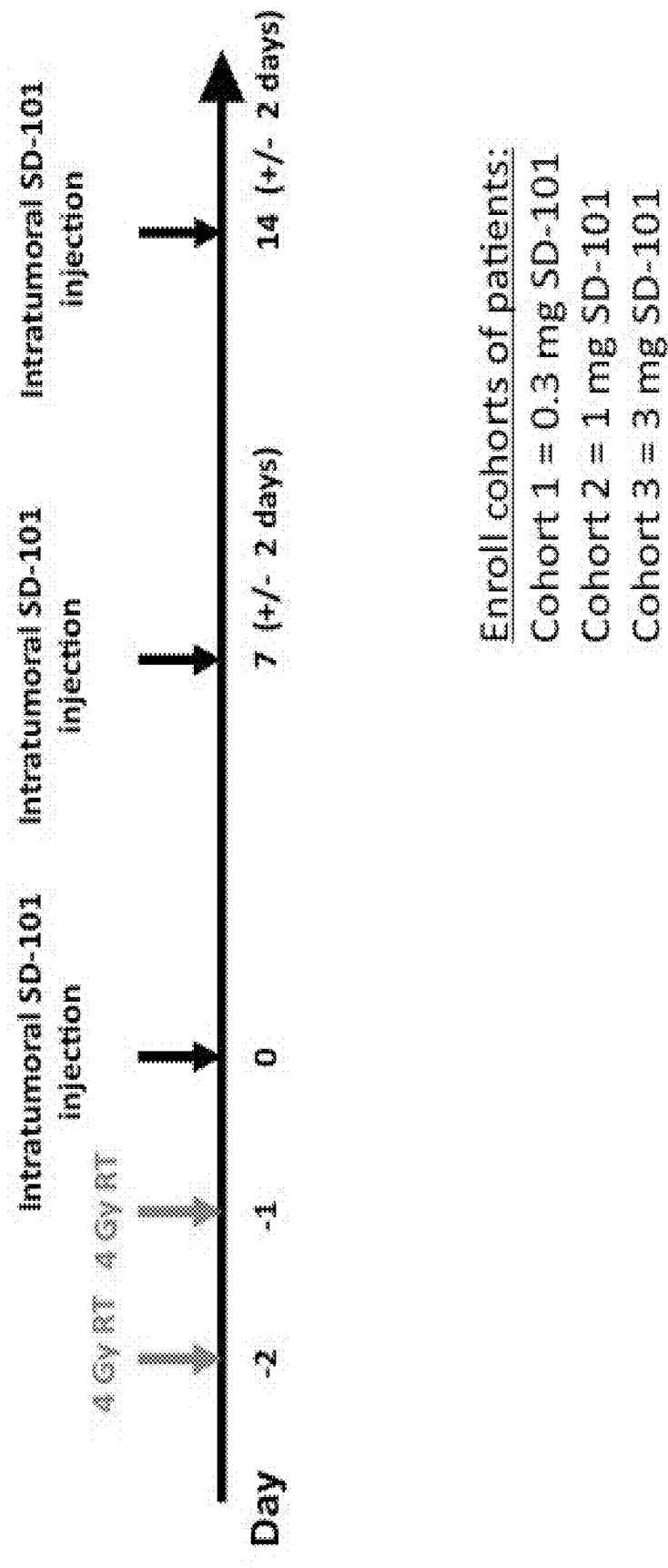
FIG. 2 shows an exemplary schema for an exemplary treatment protocol.

The methods described herein include the treatment of residual, relapsed or refractory cancer using methods comprising intratumoral immunostimulation. In some aspects, the methods comprising intratumoral immunostimulation can be performed in the presence of allogeneic immune effector cells. In other aspects, the methods comprising intratumoral immunostimulation can be performed in combination with low dose radiation therapy. Often, the methods of the disclosure can induce a systemic allogeneic antitumor T-cell immune response which in some aspects, may result in tumor regression.

To facilitate an understanding of the disclosure, a number of terms are defined below.

Before the present active agents and methods are described, it is to be understood that this disclosure is not limited to the particular methodology, products, apparatus and factors described, as such methods, apparatus and formulations can, of course, vary. It is also to be understood that the terminology used herein is for the purpose of describing particular aspects only, and is not intended to limit the scope of the present disclosure which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

While preferred aspects of the present disclosure have been shown and described herein, it is to be understood that the disclosure is not limited to the particular aspects of the disclosure described below, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims. In this specification and the appended claims, the singular forms "a," "an" and "the" include plural reference unless the context clearly dictates otherwise.

Definitions

Unless defined otherwise, all technical and scientific terms used herein have the same meaning as commonly understood by one of ordinary skill in the art to which this disclosure belongs. All publications mentioned herein are incorporated herein by reference for the purpose of describing and disclosing devices, formulations and methodologies which are described in the publication and which might be used in connection with the presently described disclosure.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges can independently be included in the smaller ranges is also encompassed within the disclosure, subject to any specifically excluded limit in the stated range. Where the stated range includes one or both of the limits, ranges excluding either both of those included limits are also included in the disclosure.

In the following description, numerous specific details are set forth to provide a more thorough understanding of the present disclosure. However, it will be apparent to one of skill in the art that the present disclosure can be practiced without one or more of these specific details. In other instances, well-known features and procedures well known to those skilled in the art have not been described in order to avoid obscuring the disclosure.

Generally, conventional methods of protein synthesis, recombinant T-cell culture and protein isolation, and recombinant DNA techniques within the skill of the art are employed in the present disclosure. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

As used herein, the terms "treat," "treatment," "treating," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented. Similarly, a person with cancer is "responsive" to a treatment if at least one symptom of the cancer is alleviated, terminated, slowed, or prevented. As used herein, a person with cancer is also "responsive" to a treatment if recurrence or metastasis of the cancer is reduced, slowed, delayed or prevented.

The term "subject" as used herein includes humans as well as other mammals. The term "treating" as used herein includes achieving a therapeutic benefit and/or a prophylactic benefit. By therapeutic benefit is meant eradication or amelioration of the cancer. Also, a therapeutic benefit is achieved with the eradication or amelioration of one or more of the physiological symptoms associated with cancer such that an improvement is observed in the animal subject, notwithstanding the fact that the animal subject can still be afflicted with that cancer.

Cancers and cancer cells that can be treated include, but are not limited to, hematological cancers, including leukemia, lymphoma and myeloma, and solid cancers, including for example tumors of the brain (glioblastomas, medulloblastoma, astrocytoma, oligodendroglioma, ependymomas), carcinomas, e.g. carcinoma of the lung, liver, thyroid, bone, adrenal, spleen, kidney, lymph node, small intestine, pancreas, colon, stomach, breast, endometrium, prostate, testicle, ovary, skin, head and neck, and esophagus.

In an aspect, the cancer is a hematological cancer. In an aspect, the hematological cancer is a leukemia. In another aspect, the hematological cancer is a myeloma. In an aspect, the hematological cancer is a lymphoma. A plurality of classifications for lymphomas are known to one of ordinary skill in the art. For example, lymphomas can be classified as precursor T-cell lymphoma, follicular lymphoma, diffuse large B-cell lymphoma, mantle cell lymphoma, B-cell chronic lymphocytic lymphoma, MALT lymphoma, Burkitt's lymphoma, mycosis fungoides, peripheral T-cell lymphoma, nodular sclerosis, mixed cellularity Hodgkin lymphoma, Hodgkin's lymphoma and Non-Hodgkin lymphomas (NHLs).

Non-Hodgkin lymphomas are a heterogeneous group of disorders involving malignant monoclonal proliferation of lymphoid cells in lymphoreticular sites, including lymph nodes, bone marrow, the spleen, the liver, and the gastrointestinal tract. Presenting symptoms usually include peripheral lymphadenopathy. Compared with Hodgkin lymphoma, there is a greater likelihood of disseminated disease at the time of diagnosis. Diagnosis is usually based on lymph node or bone marrow biopsy or both. Conventional treatment involves radiation therapy, chemotherapy, or both.

Most (80 to 85%) NHLs arise from B-cells; the remainder arise from T-cells or natural killer cells. Either precursor or mature cells can be involved. Overlap exists between lymphocytic leukemia and NHL because both involve proliferation of lymphocytes or their precursors. A leukemia-like picture with peripheral lymphocytosis and bone marrow involvement can be present in up to 50% of children and in about 20% of adults with some types of NHL. A prominent leukemic phase is less common in aggressive lymphomas, except Burkitt's and lymphoblastic lymphomas.

Specific diseases of the disclosure include, without limitation, precursor B-lymphoblastic leukemia/lymphoma; B-cell chronic lymphocytic leukemia/small lymphocytic lymphoma; B-cell prolymphocytic leukemia; lymphoplasmacytic lymphoma; splenic marginal zone B-cell lymphoma (±villous lymphocytes); hairy cell leukemia; plasma cell myeloma/plasmacytomas; extranodal marginal zone B-cell lymphoma of the MALT type; nodal marginal zone B-cell lymphoma (±monocytoid B-cells); follicular lymphoma; mantle cell lymphoma; diffuse large B-cell lymphomas (including mediastinal large B-cell lymphoma and primary effusion lymphoma); and Burkitt's lymphoma. In some aspects, the lymphoma being treated has a lymph node involvement.

Another disease of interest for treatment by the methods of the disclosure is mycosis fungoides, which is the most common form of cutaneous T-cell lymphoma, which is an uncommon chronic T-cell lymphoma primarily affecting the skin and occasionally the internal organs. Mycosis fungoides occurs in about 1 in 100,000 to 350,000 individuals. It accounts for approximately 70 percent of cutaneous T-cell lymphomas. Unlike most other lymphomas, it is insidious in onset, sometimes appearing as a chronic, pruritic rash that is difficult to diagnose. It begins focally but can spread to involve most of the skin. Lesions are plaquelike but can become nodular or ulcerated. Eventually, systemic involvement of lymph nodes, liver, spleen, and lungs occurs, resulting in the advent of symptoms, which include fever, night sweats, and unintentional weight loss. Although the skin is involved, the skin cells themselves are not cancerous. Mycosis fungoides usually occurs in adults over age 50, although affected children have been identified.

Mycosis fungoides progresses slowly through several stages. Most affected individuals initially develop skin lesions called patches, which are flat, scaly, pink or red areas on the skin that can be itchy. Cancerous T-cells, which cause the formation of patches, are found in these lesions. Skin problems result when cancerous T-cells move from the blood into the skin. Patches are most commonly found on the lower abdomen, upper thighs, buttocks, and breasts. They can disappear and reappear or remain stable over time. In most affected individuals, patches progress to plaques, the next stage of mycosis fungoides.

Plaques are raised lesions that are usually reddish, purplish, or brownish in color and itchy. Plaques commonly occur in the same body regions as patches. While some plaques arise from patches, others develop on their own, and an affected person can have both patches and plaques simultaneously. As with patches, cancerous T-cells are found in plaques. Plaques can remain stable or can develop into tumors. Not everyone with patches or plaques develops tumors.

The tumors in mycosis fungoides, which are composed of cancerous T-cells, are raised nodules that are thicker and deeper than plaques. They can arise from patches or plaques or occur on their own. In any stage of mycosis fungoides, the cancerous T-cells can spread to other organs, including the lymph nodes, spleen, liver, and lungs. In addition, affected individuals have an increased risk of developing another lymphoma or other type of cancer.

Hematopoietic cell transplantation (HCT) is the transplantation of donor cells including multipotent hematopoietic cells, usually derived from bone marrow, peripheral blood, or umbilical cord blood. For the methods of the disclosure, the hematopoietic cells are allogeneic to the cancer patient, i.e. are other than identical (not autologous or identical twin. Hematopoietic cells can be obtained from bone marrow, e.g. vertebrae, pelvic bone, etc. or hematopoietic cells can be mobilized, e.g. with G-CSF, and collected by apheresis or similar methods, as is known in the art. For a review, see, for example, Warren et al. (2012 Blood 120(14):2796-806; Li and Sykes (2012) Nat. Rev. Immunol. 12(6):403-16.

The term "histocompatibility" refers to the similarity of tissue between different individuals. The level of histocompatibility describes how well matched the patient and donor are. The major histocompatibility determinants are the human leukocyte antigens (HLA). HLA typing is performed between the potential marrow donor and the potential transplant recipient to determine how close a HLA match the two are. The closer the match the less the donated marrow and the patient's body will react against each other.

The term "human leukocyte antigens" or "HLA", refers to proteins (antigens) found on the surface of white blood cells and other tissues that are used to match donor and patient. For instances, a patient and potential donor can have their white blood cells tested for such HLA antigens as HLA-A, B and DR. Each individual has two sets of these antigens, one set inherited from each parent. In hematopoietic transplantation, the word "match" relates to how similar the HLA typing is between the donor and the recipient. For the purposes of the present disclosure, the HCT can be matched or mismatched between donor and recipient, e.g. matching at 1, 2, 3, 4, 5, or 6 of the alleles at HLA-A, HLA-B and HLA-DR. It will be understood by one of skill in the art that even a perfect match at these 6 alleles does not provide for perfect identity between donor and recipient, as a number of minor histocompatibility loci can be mismatched.

"Major histocompatibility complex antigens" ("MHC", also called "human leukocyte antigens", HLA) are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals can carry class I HLA-B, genes B5, and Bw41, respectively. Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA matched" refers to a donor recipient pair in which none of the HLA antigens are mismatched between the donor and recipient. HLA matched (i.e., where all of the 6 alleles are matched) donor/recipient pairs have a decreased risk of graft v. host disease (GVHD) relative to mismatched pairs (i.e. where at least one of the 6 alleles is mismatched).

As used herein, the term "HLA mismatched" refers to a donor recipient pair in which at least one HLA antigen, in particular with respect to HLA-A, HLA-B and HLA-DR, is mismatched between the donor and recipient. In some aspects, one haplotype is matched and the other is mismatched. This situation is frequently found with organs from living or deceased donors. HLA mismatched donor/recipient pairs have an increased risk of GVHD relative to perfectly matched pairs (i.e. where all 6 alleles are matched).

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S can follow an allele's designation to specify an expression level or other non-genomic data known about it. Thus, a completely described allele can be up to 9 digits long, not including the HLA-prefix and locus notation.

Hematopoietic stem cell transplantation (HCT) is the transplantation of multipotent hematopoietic stem cells, usually derived from bone marrow, peripheral blood, or umbilical cord blood. For the methods of the disclosure, the hematopoietic cells can be engineered into one of two products. The hematopoietic cells are engineered into a product for infusion having a specific pre-determined number of purified (e.g., 70% purity) CD34+ progenitor cells and CD3+ T-cells. The hematopoietic cells can be obtained from the solid organ donor, and thus are HLA-matched to the solid organ, and HLA-mismatched to the organ recipient. The hematopoietic cells can be obtained from the solid organ donor, and thus are HLA-matched to the solid organ, and HLA-matched to the organ recipient.

Where the donor is deceased, hematopoietic cells can be obtained from bone marrow (e.g. vertebrae, pelvic bone, etc). Where the donor is a living donor, hematopoietic cells can be mobilized (e.g. with G-CSF), and collected by apheresis or similar methods. Alternatively, cells can be obtained from bone marrow (e.g. pelvic bone, etc).

Hematopoietic cells can be frozen (e.g., cryopreserved) for prolonged periods without damaging a significant number of cells. To cryopreserve HSC, a preservative, DMSO, must be added, and the cells must be cooled very slowly in a controlled-rate freezer to prevent osmotic cellular injury during ice crystal formation. HSC can be stored for years in a cryofreezer, which typically uses liquid nitrogen.

In aspects that include HCT, the recipient's immune system is conditioned prior to infusion of the hematopoietic cells, e.g. with a myeloablative or non-myeloablative (RIC) procedure. Non-myeloablative transplants use doses of chemotherapy, antibody and/or radiation that are too low to eradicate all the bone marrow cells of a recipient, thus enabling stable mixed chimerism where both recipient and donor HSC coexist in the bone marrow space.

The recipient's immune system is conditioned with a non-myeloablative procedure prior to infusion of the hematopoietic cells. Non-myeloablative transplants use doses of antibody and radiation that are too low to eradicate all the bone marrow cells of a recipient, thus enabling the desired goal of stable mixed chimerism where both recipient and donor HSC coexist in the bone marrow space. The conditioning regimen includes treatment with anti-thymocyte globulin (ATG); total lymphoid irradiation, and corticosteroids (e.g. prednisone) usually for a period of from about 10 to 12 days (e.g. for about 11 days).

"Immunosuppression", as used herein, refers to the treatment of a graft recipient with agents, primarily to diminish the immune responses of the host immune system against the graft, although the agents can also diminish GVHD of the donor hematopoietic cells. Exemplary immunosuppression regimens are described in more detail herein, but will generally be conventional for a period of about 6 to 12 months. The recipient is tested for mixed chimerism of the hematopoietic system, and if found to have maintained mixed chimerism after at least 6 months, will be tapered off immunosuppression.

Immunosuppressive treatment of the transplantation patient begins with the induction phase, perioperatively and immediately after transplantation. Maintenance therapy then continues until withdrawal for individuals showing stable mixed chimerism. Induction and maintenance strategies use different medicines at specific doses or at doses adjusted to achieve target therapeutic levels to give the transplantation patient the best hope for long-term graft survival.

Primary immunosuppressive agents include calcineurin inhibitors, which combine with binding proteins to inhibit calcineurin activity, and which include, for example, tacrolimus, cyclosporine A, etc. Levels of both cyclosporine and tacrolimus must be carefully monitored. Initially, levels can be kept in the range of 10-20 ng/mL, but, after 3 months, levels can be kept lower (5-10 ng/mL) to reduce the risk of nephrotoxicity.

Adjuvant agents are usually combined with a calcineurin inhibitor and include, but are not limited to, steroids, azathioprine, mycophenolate mofetil, and sirolimus. Protocols of interest include a calcineurin inhibitor with mycophenolate mofetil. The use of adjuvant agents allows clinicians to achieve adequate immunosuppression while decreasing the dose and toxicity of individual agents.

Antibody-based therapy uses monoclonal (e.g., muromonab-CD3) or polyclonal antibodies or anti-CD25 antibodies (e.g., basiliximab, daclizumab) and can be administered in the early posttransplant period (up to 8 wk). Antibody-based therapy allows for avoidance or dose reduction of calcineurin inhibitors, possibly reducing the risk of nephrotoxicity. The adverse effect profile of the polyclonal and monoclonal antibodies limits their use in some patients.

"Graft-versus-host disease (GVHD)" is an inflammatory disease that is peculiar to transplantation of hematopoietic cells. GVHD is an attack of the donor bone marrow's immune cells against the recipient's tissues. GVHD is a risk for both HLA-matched and -mismatched transplantations. GVHD can occur even if the donor and recipient are HLA-matched because the immune system can still recognize other differences between their tissues. GVHD is usually mediated by T-cells, which react to foreign peptides presented on the MHC of the host. The risk of GVHD is markedly reduced in patients with mixed instead of complete chimerism and achieving mixed chimerism is desirable for this reason. In addition, immunodeficiency and infection are more frequently observed in complete versus mixed chimerism.

There are two types of GVHD, acute and chronic. Acute GVHD typically occurs in the first 3 months after transplantation and can involve the skin, intestine, or the liver. High-dose corticosteroids such as prednisone are a standard treatment.

Chronic GVHD can also develop after haplotype matched transplant and typically occurs after the first 3 months following transplant. Chronic GVHD is the major source of late treatment-related complications, although it less often results in death. In addition to inflammation, chronic GVHD can lead to the development of fibrosis, or scar tissue, similar to scleroderma; it can cause functional disability and require prolonged immunosuppressive therapy.

"Chimerism", as used herein, refers to chimerism of the hematopoietic system. A determination of whether an individual is a full chimera, mixed chimera, or non-chimeric can be made by an analysis of a hematopoietic cell sample from the graft recipient, e.g. peripheral blood, bone marrow, etc. as known in the art. Analysis can be done by any convenient method of typing. For example, the degree of chimerism amongst all mononuclear cells, T-cells, B-cells, CD56$^+$ NK cells, and CD15$^+$ neutrophils can be determined using PCR with probes for microsatellite analysis. Commercial kits that distinguish polymorphisms in short terminal repeat lengths of donor and host origin are available. Automated readers provide the percentage of donor type cells based on standard curves from artificial donor and hosT-cell mixtures. Individuals who exhibited more than a 95% donor cells in a given blood cell lineage by such analysis at any time post-transplantation are referred to as having full donor chimerism.

"Mixed chimerism" is defined as greater than 5% donor but less than 95% donor DNA in such analysis. Mixed chimeras can have greater than 5%, greater than 10%, greater than 20%, greater than 30%, greater than 40%, greater than 50%, greater than 60%, greater than 70%, greater than 80%, greater than 90%, greater than 95% donor cells in a given blood cell lineage at the time of treatment.

An "immunostimulant" is an agent that increases the effective immune response to an antigen. For the purposes of the present disclosure, an antigen can be tumor antigens and/or allogeneic histocompatibility antigens, which can be released in response to cytoreductive therapy, e.g. radiation, chemotherapy, and the like. Immunostimulants often act on dendritic cells, which present antigen to effector T-cells. Immunostimulant agents of interest for this purpose include Freunds adjuvant, anti-CTLA4, anti-PD1, GM-CSF, dendritic cells, and the like. Further, immunostimulatory DNA sequences are of particular interest.

The immunostimulant can be administered to the patient, parenterally, including intramuscular, intraarterial, intrathecal, intradermal, intraperitoneal, intrasplenic, subcutaneous, and intravenous administration, and particularly injected directly into the tumor, for example to at least one tumor nodule. The dose of immunostimulant can be delivered at appropriate intervals, e.g. 1, 2, 3, or more injections at daily, semi-daily, weekly intervals concurrent with, or following radiation.

Assays for determining the effectiveness of a T-cell response can be measured by various assays known in the art, for example mixed lymphocyte reaction; ELISA, flow cytometry, immunohistochemistry, etc. Some assays for determining effectiveness of a T-cell response are described in the examples disclosed herein.

Efficacy of the cancer treatment can be monitored by known methods to those of ordinary skill in the art, including a decrease in size of a palpable tumor, etc., as appropriate for the specific cancer being treated.

In some aspects the immunostimulant is an immunostimulatory sequence (ISS). Oligodeoxynucleotides (ODNs) containing CpG, (also known as ISS) induce immunomodulation by binding to Toll-like receptor (TLR) 9 in B-cells and DCs, which become activated and in turn, cause recruitment and/or activation of T lymphocytes, macrophages, monocytes and NK cells. DCs at tumor sites are a heterogeneous population and include myeloid DCs and plasmacytoid DCs (PDCs). Myeloid DCs (MDCs) preferentially express TLR-2 and TLR-4, and produce IL-12, while PDCs express TLR-7 and TLR-9, and produce interferon alpha (IFN-$\alpha$). A broad range of DNA sequences will act on TLR receptors, which have been shown in the art to recognize a range of bacterial DNA sequences, for example as reviewed by Gosu et al. (2012) *Molecules* 17(11):13503-29; Adams (2009) Immunotherapy 1(6):949-64; and Engel (2011) Expert Rev. Clin. Pharmacol. 4(2):275-89.

Three classes of ISS—A, B, and C—have been described; all bind to the same receptor, TLR-9. These classes can be discriminated by their structure, biologic activity, and the intracellular compartment where they exert their effect. ISS of the A class produce stable, complex, higher order multimeric structures. The B class remains as discrete ODN. The C class can bind to itself due to its palindromic nature, producing double-stranded duplex or hairpin structures. The A class promotes the production of IFN-$\alpha$ by PDCs, but has little effect on B-cells or PDC maturation. The B class contains strong B-cell stimulators and induces PDC maturation, but is a poor inducer of IFN-$\alpha$. The C class has properties intermediate between the A and B classes.

The initial DC response to TLR-9 in humans is largely initiated by plasmacytoid dendritic cells (pDC), which respond by secreting substantial IFN-$\alpha$, small amounts of tumor necrosis factor-alpha (TNF-$\alpha$), and a number of other cytokines and chemokines, as well as maturing into more efficient antigen-presenting cells. These activated pDCs become mobilized and migrate from the tissue to lymph nodes. The activation and maturation of pDCs initiate a rapid cascade of responses by other cell types, leading to potent stimulation of both innate and adaptive immune responses.

Pharmacodynamic measure of the effects of ISS can be accomplished through assessing PDC activation, plasma cytokines, or more conveniently through the increase in levels of IFN-α inducible gene messenger ribonucleic acid (m-RNA) in blood mononuclear cells.

In some aspects, the immunostimulant is SD-101, a 30-mer phosphorothioate molecule of the following sequence: 5'-TCG AAC GTT CGA ACG TTC GAA CGT TCG AAT-3' (SEQ ID NO: 1). SD-101 contains juxtaposed unmethylated CpG motifs with flanking regions, in a self-complimentary palindromic sequence that is designated as a Class C-type sequence (CpG-C). SD-101 is highly active in stimulating primate and rodent immune cells. In other aspects, the immunostimulant is ODN1826, which has the sequence 5'-TCCATGACGTTCCTGACGTT-3' (SEQ ID NO: 2).

Phosphorothioate (PS) ODNs (15-30 nucleotides in length) have relatively well defined half-lives, volumes of distribution, metabolism, and tissue/cellular destinations based upon their phosphorothioate structure. The change in chemistry which interferes with the activity of ubiquitous nuclease enzymes extends the plasma half-life and thus their ability to penetrate and distribute through tissue compartments. Sequence has little effect on the PK tissue distribution, clearance, and excretion of PS ODNs.

Generally, PS ODNs behave similarly across species except for their specifically designed activities. The significant alterations in the PK of such entities are dependent upon the mode of administration (IV, intramuscular [IM], SC, inhaled, or oral) and the dosing intervals.

Radiation therapy is used broadly, and includes a number of modalities, including radiation therapy or ionizing radiation, thermal stress or thermal therapy, irreversible electroporation (IRE), oxidative stress, radiofrequency ablation, and combinations thereof. Tumors can be pretreated with a cell-sensitizing composition prior to exposure. Radiation therapy can include both "sealed" and "unsealed" sources of therapeutic radiation including, but not limited to, ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, gamma-ray therapy, and cobalt therapy.

In some aspects, radiation is delivered locally to the tumor, i.e. with shielding of the body, and is delivered at a non-curative dose, e.g. from about 1 to about 36 Gy, from about 2 to about 30 Gy, from about 3 to about 20 Gy, or around about 4, 8, 12, 16, 20 Gy. In other aspects, radiation is delivered locally to the tumor, i.e. with shielding of the body, and is delivered at a non-curative dose, e.g. from 1 to 36 Gy, from 2 to 30 Gy, from 3 to 20 Gy, or 4, 8, 12, 16, 20 Gy. However, the use of higher doses is not necessarily contraindicated, depending on the patient status.

In some aspects, recipients are treated with radiation. The radiation can be fractionated or unfractionated. In the aspect that a recipient is treated with more than one dose of radiation, all doses can be fractionated. In another aspect that a recipient is treated with more than one dose of irradiation, all doses can be unfractionated. In another aspect that a recipient is treated with more than one dose of irradiation, the doses can be a mix of fractionated unfractionated.

In some aspects, the radiation is delivered intraoperatively. In some aspects, the radiation is delivered intravenously. In some aspects, the radiation is delivered intraarterially. In some aspects, the radiation is delivered subcutaneously. In some aspects, the radiation is delivered intraperitoneally.

In some aspects, a single dose of radiation can be delivered to the recipient. In other aspects, the recipient can receive more than one dose of radiation. For example, a recipient can receive at least one dose of radiation, two doses of radiation, three doses of radiation, four doses of radiation, five doses of radiation, six doses of radiation, seven doses of radiation, eight doses of radiation, nine doses of radiation, 10 doses of radiation, 11 doses of radiation, 12 doses of radiation, 13 doses of radiation, 14 doses of radiation, 15 doses of radiation, 16 doses of radiation, 17 doses of radiation, 18 doses of radiation, 19 doses of radiation, or at least 20 doses of radiation.

In some aspects, each dose of radiation can be at least 1 Gy, 2 Gy, 3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy, 20 Gy, 21 Gy, 22 Gy, 23 Gy, 24 Gy, 25 Gy, 26 Gy, 27 Gy, 28 Gy, 29 Gy, 30 Gy, 31 Gy, 32 Gy, 33 Gy, 34 Gy, 35 Gy, 36 Gy, 37 Gy, 38 Gy, 39 Gy, 40 Gy, 41 Gy, 42 Gy, 43 Gy, 44 Gy, 45 Gy, 46 Gy, 47 Gy, 48 Gy, 49 Gy or at least 50 Gy.

In other aspects, about each dose of radiation can be at least about 1 Gy, about 2 Gy, about 3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy, about 20 Gy, about 21 Gy, about 22 Gy, about 23 Gy, about 24 Gy, about 25 Gy, about 26 Gy, about 27 Gy, about 28 Gy, about 29 Gy, about 30 Gy, about 31 Gy, about 32 Gy, about 33 Gy, about 34 Gy, about 35 Gy, about 36 Gy, about 37 Gy, about 38 Gy, about 39 Gy, about 40 Gy, about 41 Gy, about 42 Gy, about 43 Gy, about 44 Gy, about 45 Gy, about 46 Gy, about 47 Gy, about 48 Gy, about 49 Gy or at least about 50 Gy.

Thermal stress or therapy can include focused ultrasound (FUS or HIFU), radiofrequency, infrared sauna, microwave heating, induction heating, magnetic hyperthermia, infusion of warmed liquids, or direct application of heat. The thermal stress can include local hyperthermia and/or regional hyperthermia. The thermal stress or thermal therapy can also include exposure to sub-lethal heat. For example, a hyperthermia modality can heat a cancer cell too much lower therapeutic temperatures compared to other tissue ablation techniques. For instance, the elevation above a normal body temperature of 37° C. will fall within a range of 42° C. to 45° C.

Irreversible electroporation uses a series of microsecond electrical pulses instead of extreme heat, freezing, radiation or microwave energy—to permanently open cell membranes in tumors. Once the cell membrane pores are opened, the death of the targeted cancer cells is induced. Surrounding veins, nerves and ducts within the targeted area are largely unaffected by the process around them.

The radiation can be image guided. For example, clinical HIFU procedures are typically image-guided to permit treatment planning and targeting before applying a therapeutic or ablative level of ultrasound energy. When MRI is used for guidance, the technique is sometimes called Magnetic Resonance-guided Focused Ultrasound, often shortened to MRgFU. When ultrasonography is used, the technique is sometimes called Ultrasound-guided Focused Ultrasound, often shortened to USgFUS.

In some aspects where the immunostimulant is an ISS, it is injected intratumorally with 24 hours of radiation, and is optionally administered 1-3 additional times, e.g. at weekly intervals. The dose can be at least about 0.1 mg/injection, at least about 0.3 mg, at least about 0.5 mg, at least about 1 mg, at least about 3 mg, at least about 5 mg, and not more than about 10 mg.

The term "relapse" refers to the recurrence of illness after recovery from the illness.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect can be prophylactic in terms of completely or partially preventing a disease or symptom thereof and/or can be therapeutic in terms of a partial or complete stabilization or cure for a disease and/or adverse effect attributable to the disease. Treatment as used herein covers any treatment of a disease in a mammal, particularly a human, and includes: (a) preventing the disease or symptom from occurring in a subject which can be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans.

The term "graft management" refers to therapeutic methods that induce and/or promote repair engraftment of a solid organ, but not limited to, kidney transplantation.

The term "pharmaceutically acceptable" as used herein refers to a compound or combination of compounds that will not impair the physiology of the recipient human or animal to the extent that the viability of the recipient is compromised. Preferably, the administered compound or combination of compounds will elicit, at most, a temporary detrimental effect on the health of the recipient human or animal.

The term "carrier" as used herein refers to any pharmaceutically acceptable solvent of agents that will allow a therapeutic composition to be administered directly to a wound of the skin. The carrier will allow a composition to be topically applied to an exposed surface of an organ for transplantation and the site of the recipient where the organ is to be placed. A "carrier" as used herein, therefore, refers to such solvent as, but not limited to, water, saline, oil-water emulsions, or any other solvent or combination of solvents and compounds known to one of skill in the art that is pharmaceutically and physiologically acceptable to the recipient human or animal.

The term "assessing" and "evaluating" are used interchangeably to refer to any form of measurement, and includes determining if an element is present or not. The terms "determining," "measuring," "assessing," and "assaying" are used interchangeably and include both quantitative and qualitative determinations. Assessing can be relative or absolute. "Assessing the presence of" includes determining the amount of something present, as well as determining whether it is present or absent.

The methods described herein include treatment of residual, relapsed or refractory cancer comprising administration of an immunostimulant to a subject in need thereof. In some aspects, the methods may include administration of an immunostimulant in the presence of allogeneic immune effector cells. Often, the immunostimulant is administered in combination with radiation therapy as described herein.

In some aspects, the subject in need thereof can have been engrafted with an allogeneic HCT and the subject can have maintained a mixed or full allogeneic chimerism following engraftment. Often, chimerism can be determined by the percentage of circulating $CD3^+$ T-cells within a subject following HCT. In an exemplary aspect, chimerism can include at least about 5% circulating $CD3^+$ T-cells that are allogeneic to the subject in need thereof. In another exemplary aspect, chimerism can include at least 5% circulating $CD3^+$ T-cells that are allogeneic to the subject in need thereof. In some aspects, the methods described herein can further include administration of radiation and an administration of an immunostimulant to a subject in need thereof.

In other aspects, in the absence of an allogeneic HCT, the subject in need thereof can be engrafted with an allogeneic HCT. Often, in the absence of an allogeneic HCT, the subject in need thereof can be engrafted with an allogeneic HCT concurrently or prior to radiation and immunostimulation. In some aspects, radiation and/or immunostimulation can be administered to the subject in need thereof once at least about 5% circulating $CD3^+$ T-cells are allogeneic to the subject in need thereof.

In some aspects, the methods disclosed herein include a method of treating cancer in a subject, the method comprising administering to the subject an immunostimulant in combination with irradiation, wherein said irradiation induces a systemic allogeneic anti-tumor T-cell immune response that results in tumor regression in untreated sites of disease, and wherein the subject has undergone bone marrow transplant prior to said administering. Often the subject is a patient.

In some aspects, the subject has previously had an allogeneic hematopoietic cell transplantation resulting in mixed or complete chimerism. In some aspects, the subject has at least about 5% allogeneic type leukocytes. Often, the allogeneic type leukocytes are at least about 5% circulating allogeneic type $CD3^+$ T-cells.

In some aspects, the irradiation is local-type irradiation. Often, the irradiation is selected from ionizing radiation, thermal therapy, ultrasound, irreversible electroporation (IRE), oxidative stress, radiofrequency ablation, and combinations thereof. In some aspects, the irradiation is ionizing radiation delivered at from 1 to 36 Gy. In some aspects, the immunostimulant is oligodeoxynucleotides (ODN) containing CpG that bind to the Toll-like receptor (TLR) 9 and activate dendritic cells and B-cells.

In some aspects, the cancer is a solid tumor. In other aspects, the cancer is a lymphoma. Often, the lymphoma is a Non-Hodgkin's lymphoma or a Hodgkin's lymphoma. In some aspects, the lymphoma is a cutaneous T-cell lymphoma or mycosis fungoides. In other aspects, the cancer is a carcinoma. In some aspects, the carcinoma is renal cell carcinoma. Often, cancer is selected from the group comprising residual cancer, relapsed cancer and refractory cancer.

In some aspects, the methods described herein include a method of treating a cancer, the method comprising: (a) identifying a subject having the cancer where the subject is chimeric for allogeneic hematopoietic stem cells; and (b) intratumorally injecting an immunostimulant in combination with irradiation at a tumor nodule to induce an immune response resulting in tumor regression. In some aspects, the subject has previously had an allogeneic hematopoietic cell transplantation resulting in mixed or complete chimerism. In some aspects, the subject has at least about 5% allogeneic type leukocytes. Often, the allogeneic type leukocytes are at least about 5% circulating allogeneic type CD3$^+$ T-cells.

In some aspects, the irradiation is local-type irradiation. Often, the irradiation is selected from ionizing radiation, thermal therapy, ultrasound, irreversible electroporation (IRE), oxidative stress, radiofrequency ablation, and combinations thereof. In some aspects, the irradiation is ionizing radiation delivered at from 1 to 36 Gy. In some aspects, the immunostimulant is oligodeoxynucleotides (ODN) containing CpG that bind to the Toll-like receptor (TLR) 9 and activate dendritic cells and B-cells.

In some aspects, the cancer is a solid tumor. In other aspects, the cancer is a lymphoma. Often, the lymphoma is a Non-Hodgkin's lymphoma or a Hodgkin's lymphoma. In some aspects, the lymphoma is a cutaneous T-cell lymphoma or mycosis fungoides. In other aspects, the cancer is a carcinoma. In some aspects, the carcinoma is renal cell carcinoma. Often, cancer is selected from the group comprising residual cancer, relapsed cancer and refractory cancer.

In some aspects, the methods described herein include a method of treating residual, relapsed or refractory cancer, the method comprising: (a) identifying a subject having a residual, relapsed or refractory cancer where the patient is chimeric for allogeneic hematopoietic stem cells and has at least about 5% allogeneic type leukocytes; and (b) intratumorally injecting an immunostimulant in combination with involved field local irradiation at a tumor nodule to induce a systemic allogeneic anti-tumor immune response that results in tumor regression in untreated sites of disease.

In some aspects, the subject has previously had an allogeneic hematopoietic cell transplantation resulting in mixed or complete chimerism. Often, the allogeneic type leukocytes are at least about 5% circulating allogeneic type CD3$^+$ T-cells.

In some aspects, the irradiation is local-type irradiation. Often, the irradiation is selected from ionizing radiation, thermal therapy, ultrasound, irreversible electroporation (IRE), oxidative stress, radiofrequency ablation, and combinations thereof. In some aspects, the irradiation is ionizing radiation delivered at from 1 to 36 Gy. In some aspects, the immunostimulant is oligodeoxynucleotides (ODN) containing CpG that bind to the Toll-like receptor (TLR) 9 and activate dendritic cells and B-cells.

In some aspects, the cancer is a solid tumor. In other aspects, the cancer is a lymphoma. Often, the lymphoma is a Non-Hodgkin's lymphoma or a Hodgkin's lymphoma. In some aspects, the lymphoma is a cutaneous T-cell lymphoma or mycosis fungoides. In other aspects, the cancer is a carcinoma. In some aspects, the carcinoma is renal cell carcinoma. Often, cancer is selected from the group comprising residual cancer, relapsed cancer and refractory cancer.

In some aspects, the disclosure further describes kits for use with the methods described herein. In some aspects, the disclosure includes a kit for treating residual, relapsed or refractory cancer, the kit comprising: (a) an immunostimulant; (b) a means for administering involved field local irradiation to a tumor nodule of a subject; and (c) a set of instructions for administering the immunostimulant and the involved field radiation to the subject.

In some aspects, the subject has previously had an allogeneic hematopoietic cell transplantation resulting in mixed or complete chimerism. In some aspects, the subject has at least about 5% allogeneic type leukocytes. Often, the allogeneic type leukocytes are at least about 5% circulating allogeneic type CD3$^+$ T-cells.

In some aspects, the irradiation is local-type irradiation. Often, the irradiation is selected from ionizing radiation, thermal therapy, ultrasound, irreversible electroporation (IRE), oxidative stress, radiofrequency ablation, and combinations thereof. In some aspects, the irradiation is ionizing radiation delivered at from 1 to 36 Gy. In some aspects, the immunostimulant is oligodeoxynucleotides (ODN) containing CpG that bind to the Toll-like receptor (TLR) 9 and activate dendritic cells and B-cells.

In some aspects, the cancer is a solid tumor. In other aspects, the cancer is a lymphoma. Often, the lymphoma is a Non-Hodgkin's lymphoma or a Hodgkin's lymphoma. In some aspects, the lymphoma is a cutaneous T-cell lymphoma or mycosis fungoides. In other aspects, the cancer is a carcinoma. In some aspects, the carcinoma is renal cell carcinoma. Often, cancer is selected from the group comprising residual cancer, relapsed cancer and refractory cancer.

In some aspects, the disclosure includes a kit for treating cancer, the kit comprising: (a) an immunostimulant; (b) a means for administering radiation to a tumor nodule of a subject; and (c) a set of instructions for administering the immunostimulant and the radiation to the subject.

In some aspects, the subject has previously had an allogeneic hematopoietic cell transplantation resulting in mixed or complete chimerism. In some aspects, the subject has at least about 5% allogeneic type leukocytes. Often, the allogeneic type leukocytes are at least about 5% circulating allogeneic type CD3$^+$ T-cells.

In some aspects, the irradiation is local-type irradiation. Often, the irradiation is selected from ionizing radiation, thermal therapy, ultrasound, irreversible electroporation (IRE), oxidative stress, radiofrequency ablation, and combinations thereof. In some aspects, the irradiation is ionizing radiation delivered at from 1 to 36 Gy. In some aspects, the immunostimulant is oligodeoxynucleotides (ODN) containing CpG that bind to the Toll-like receptor (TLR) 9 and activate dendritic cells and B-cells.

In some aspects, the cancer is a solid tumor. In other aspects, the cancer is a lymphoma. Often, the lymphoma is a Non-Hodgkin's lymphoma or a Hodgkin's lymphoma. In some aspects, the lymphoma is a cutaneous T-cell lymphoma or mycosis fungoides. In other aspects, the cancer is a carcinoma. In some aspects, the carcinoma is renal cell carcinoma. Often, cancer is selected from the group comprising residual cancer, relapsed cancer and refractory cancer.

Typing Human Leukocyte Antigens

Any method known in the art can be used for HLA typing. For example, three main procedures can be used to perform HLA typing. The first is conventional serological cytotoxicity method, where samples of lymphocytes (e.g., taken from blood or spleen) are added to Terasaki plates. In some aspects, B lymphocytes can be used for class II typing. In other aspects, class I typing can be performed with the remaining leucocytes. Magnetic beads can be used to purify cells from blood or spleen.

In some aspects, each of the wells of the Terasaki plates can contain a plurality of antibodies (e.g., from either maternal sera or manufactured monoclonal antibodies). In some aspects, the HLA antigen expressed by a cell binds to an antibody in the well. After the addition of complement, cells located in a well where the HLA antigen and antibody were bound can be killed. In some aspects, a pattern of cell death can be determined from the wells. The pattern can allow for deduction of the combination of HLA antigens that were present on the original tissue. In some aspects, the deduction of the combination of HLA antigens can result in typing of HLA antigens.

Another method that can be used for HLA typing is flow cytometry. Unlike the conventional serological cytotoxicity method, flow cytometry can be used to identify one or more HLA alleles. In this method, leukocytes can be combined with antibodies that bind to the HLA types of interest. In some aspects the antibodies can be monoclonal or polyclonal. In some aspects, the antibodies can contain a detectable label. In some aspects, the antibodies can be directly conjugated to a detectable label. In other aspects, a different antibody with a detectable label binds to the HLA antibody and the complex is then detected. The types of detectable labels that can be used for HLA typing by flow cytometry are readily available and known to those of skill in the art. The sample can be analyzed to determine which HLA antibodies have bound to the cells.

Yet another method that can be used for HLA typing is DNA typing. In some aspects, DNA typing involves extracting DNA from cells and amplifying the genes that encode for the HLA peptides using polymerase chain reaction techniques which generate sequence data. The polymerase chain reaction techniques can include any polymerase chain reaction technique which generates sequence data that is known to one of skill in the art.

In some aspects, the sequence of the genes can be matched with the known nucleotide sequences of HLA alleles located in at least one of several genetic (e.g., gene bank) databases. In some aspects, the gene bank data base can be the IMGT/HLA (International Immunogenetics Project) database.

Obtaining Hematopoietic Stem Cells for Transplantation

Hematopoietic stem cell transplantation (HCT) includes the transplantation of multipotent hematopoietic stem cells from a donor to a recipient, often the recipient is a subject in need thereof. For the methods described herein, HCT can be combined with radiation and administration of an immunostimulant to the recipient. In some aspects, the hematopoietic stem cells can be HLA-matched between the donor and the recipient.

In some aspects, the hematopoietic stem cells are isolated and purified from a donor, and the donor can be living or deceased. In aspects of a living donor, hematopoietic cells can be obtained using any of the various methods known to one of skill in the art, including apheresis of mobilized peripheral blood from living donors; harvesting hematopoietic cells from bone marrow of deceased donors, and the like. In aspects of a deceased donor, hematopoietic cells can be obtained from bone marrow. For example, the cells can be obtained from the bone marrow in vertebrae, pelvic bone, femur or any other bone which contains sufficient bone marrow from which to extract hematopoietic cells.

In some aspects, hematopoietic cells can be mobilized prior to isolation and purification. In some aspects hematopoietic cells can be mobilized by treating the donor with granulocyte colony stimulating factor (G-CSF). For example, the donor can be treated with one, two, three, four, five, six, seven, eight, nine, ten or more than ten doses of G-CSF prior to isolating and purifying hematopoietic cells.

In some aspects, the doses of G-CSF can be delivered to the donor on a single day (e.g., a 24 hour day) or over the course of multiple days. For example, multiple days can include two, three, four, five, six, seven, eight, nine, ten or more than ten days. In a preferred aspect, the donor receives two doses per day.

In some aspects, each dose of G-CSF delivered to the donor is 16 µg/kg of donor body weight. In other aspects, each dose of G-CSF delivered to the donor is 8 µg/kg of donor body weight. For example, each dose of G-CSF can be more than 1 µg/kg of donor body weight, 2 µg/kg of donor body weight, 3 µg/kg of donor body weight, 4 µg/kg of donor body weight, 5 µg/kg of donor body weight, 6 µg/kg of donor body weight, 7 µg/kg of donor body weight, 8 µg/kg of donor body weight, 9 µg/kg of donor body weight, 10 µg/kg of donor body weight, 11 µg/kg of donor body weight, 12 µg/kg of donor body weight, 13 µg/kg of donor body weight, 14 µg/kg of donor body weight, 15 µg/kg of donor body weight, 16 µg/kg of donor body weight, 17 µg/kg of donor body weight, 18 µg/kg of donor body weight, 19 µg/kg of donor body weight, 20 µg/kg of donor body weight, or more than 20 µg/kg of donor body weight. In a preferred aspect, each dose of G-CSF delivered to the donor is 8 µg/kg of donor body weight.

In some aspects, apheresis can be performed after the donor receives a single dose of G-CSF. For example, apheresis can be performed one hour, two hours, three hours, four hours, five hours, six hours, seven hours, eight hours, nine hours, ten hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, or more than 48 hours after the donor receives the single dose of G-CSF.

In some aspects, apheresis can be performed after the donor receives the final dose of multiple doses of G-CSF. For example, apheresis can be performed one hour, two hours, three hours, four hours, five hours, six hours, seven hours, eight hours, nine hours, ten hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, or more than 48 hours after the donor receives the final dose of multiple doses of G-CSF.

In some aspects, apheresis can be performed to obtain an apheresis product from a donor. For example, at least one apheresis product, two apheresis products, three apheresis products, four apheresis products or five apheresis products can be obtained from a donor. In some aspects, at least two apheresis products, three apheresis products, four apheresis products, five apheresis products, six apheresis products, seven apheresis products, eight apheresis products, nine apheresis products, ten apheresis products, 11 apheresis products, 12 apheresis products, 13 apheresis products, 14 apheresis products or at least 15 apheresis products can be obtained from a donor.

For the methods described herein, hematopoietic cells can be frozen (e.g., cryopreserved) after isolation or after isolation and purification from the donor. In some aspects, hematopoietic cells can be cryopreserved using a cryopreservation medium and a method of cryopreservation known to those of skill in the art. In some aspects, the hematopoietic cells can be cryopreserved using a cryopreservation medium containing dimethylsulfoxide (DMSO), Normosol, Hetastarch and human serum albumin (HSA).

In some aspects, the concentration of DMSO in the cryopreservation medium can be less than 0.1% DMSO, 0.2% DMSO, 0.3% DMSO, 0.4% DMSO, 0.5% DMSO, 0.6% DMSO, 0.7% DMSO, 0.8% DMSO, 0.9% DMSO, 1.0% DMSO, 1.1% DMSO, 1.2% DMSO, 1.3% DMSO, 1.4% DMSO, 1.5% DMSO, 1.6% DMSO, 1.7% DMSO, 1.8% DMSO, 1.9% DMSO, 2.0% DMSO, 2.1% DMSO, 2.2% DMSO, 2.3% DMSO, 2.4% DMSO, 2.5% DMSO, 2.6% DMSO, 2.7% DMSO, 2.8% DMSO, 2.9% DMSO, 3.0% DMSO, 3.1% DMSO, 3.2% DMSO, 3.3% DMSO, 3.4% DMSO, 3.5% DMSO, 3.6% DMSO, 3.7% DMSO, 3.8% DMSO, 3.9% DMSO, 4.0% DMSO, 4.1% DMSO, 4.2% DMSO, 4.3% DMSO, 4.4% DMSO, 4.5% DMSO, 4.6% DMSO, 4.7% DMSO, 4.8% DMSO, 4.9% DMSO, 5.0% DMSO, 5.1% DMSO, 5.2% DMSO, 5.3% DMSO, 5.4% DMSO, 5.5% DMSO, 5.6% DMSO, 5.7% DMSO, 5.8% DMSO, 5.9% DMSO, 6.0% DMSO, 6.1% DMSO, 6.2% DMSO, 6.3% DMSO, 6.4% DMSO, 6.5% DMSO, 6.6% DMSO, 6.7% DMSO, 6.8% DMSO, 6.9% DMSO, 7.0% DMSO, 7.1% DMSO, 7.2% DMSO, 7.3% DMSO, 7.4% DMSO, 7.5% DMSO, 7.6% DMSO, 7.7% DMSO, 7.8% DMSO, 7.9% DMSO, 8.0% DMSO, 8.1% DMSO, 8.2% DMSO, 8.3% DMSO, 8.4% DMSO, 8.5% DMSO, 8.6% DMSO, 8.7% DMSO, 8.8% DMSO, 8.9% DMSO, 9.0% DMSO, 9.1% DMSO, 9.2% DMSO, 9.3% DMSO, 9.4% DMSO, 9.5% DMSO, 9.6% DMSO, 9.7% DMSO, 9.8% DMSO, 9.9% DMSO, 10% DMSO, 10.5% DMSO, 11% DMSO, 11.5% DMSO, 12% DMSO, 12.5% DMSO, 13% DMSO, 13.5% DMSO, 14% DMSO, 14.5% DMSO, 15% DMSO, 15.5% DMSO, 16% DMSO, 16.5% DMSO, 17% DMSO, 17.5% DMSO, 18% DMSO, 18.5% DMSO, 19% DMSO, 20% DMSO, 20.5% DMSO, 21% DMSO, 21.5% DMSO, 22% DMSO, 22.5% DMSO, 23% DMSO, 23.5% DMSO, 24% DMSO, 24.5% DMSO, 25% DMSO, 25.5% DMSO, 26% DMSO, 26.5% DMSO, 27% DMSO, 27.5% DMSO, 28% DMSO, 28.5% DMSO, 29% DMSO, 29.5% DMSO, 30% DMSO, 40% DMSO or less than 50% DMSO.

In some aspects, the concentration of normosol in the cryopreservation medium can be less than 0.1% normosol, 0.2% normosol, 0.3% normosol, 0.4% normosol, 0.5% normosol, 0.6% normosol, 0.7% normosol, 0.8% normosol, 0.9% normosol, 1.0% normosol, 1.1% normosol, 1.2% normosol, 1.3% normosol, 1.4% normosol, 1.5% normosol, 1.6% normosol, 1.7% normosol, 1.8% normosol, 1.9% normosol, 2.0% normosol, 2.1% normosol, 2.2% normosol, 2.3% normosol, 2.4% normosol, 2.5% normosol, 2.6% normosol, 2.7% normosol, 2.8% normosol, 2.9% normosol, 3.0% normosol, 3.1% normosol, 3.2% normosol, 3.3% normosol, 3.4% normosol, 3.5% normosol, 3.6% normosol, 3.7% normosol, 3.8% normosol, 3.9% normosol, 4.0% normosol, 4.1% normosol, 4.2% normosol, 4.3% normosol, 4.4% normosol, 4.5% normosol, 4.6% normosol, 4.7% normosol, 4.8% normosol, 4.9% normosol, 5.0% normosol, 5.1% normosol, 5.2% normosol, 5.3% normosol, 5.4% normosol, 5.5% normosol, 5.6% normosol, 5.7% normosol, 5.8% normosol, 5.9% normosol, 6.0% normosol, 6.1% normosol, 6.2% normosol, 6.3% normosol, 6.4% normosol, 6.5% normosol, 6.6% normosol, 6.7% normosol, 6.8% normosol, 6.9% normosol, 7.0% normosol, 7.1% normosol, 7.2% normosol, 7.3% normosol, 7.4% normosol, 7.5% normosol, 7.6% normosol, 7.7% normosol, 7.8% normosol, 7.9% normosol, 8.0% normosol, 8.1% normosol, 8.2% normosol, 8.3% normosol, 8.4% normosol, 8.5% normosol, 8.6% normosol, 8.7% normosol, 8.8% normosol, 8.9% normosol, 9.0% normosol, 9.1% normosol, 9.2% normosol, 9.3% normosol, 9.4% normosol, 9.5% normosol, 9.6% normosol, 9.7% normosol, 9.8% normosol, 9.9% normosol, 10% normosol, 10.5% normosol, 11% normosol, 11.5% normosol, 12% normosol, 12.5% normosol, 13% normosol, 13.5% normosol, 14% normosol, 14.5% normosol, 15% normosol, 15.5% normosol, 16% normosol, 16.5% normosol, 17% normosol, 17.5% normosol, 18% normosol, 18.5% normosol, 19% normosol, 20% normosol, 20.5% normosol, 21% normosol, 21.5% normosol, 22% normosol, 22.5% normosol, 23% normosol, 23.5% normosol, 24% normosol, 24.5% normosol, 25% normosol, 25.5% normosol, 26% normosol, 26.5% normosol, 27% normosol, 27.5% normosol, 28% normosol, 28.5% normosol, 29% normosol, 29.5% normosol, 30% normosol, 40% normosol or less than 50% normosol.

In some aspects, the concentration of Hetastarch in the cryopreservation medium can be less than 0.1% Hetastarch, 0.2% Hetastarch, 0.3% Hetastarch, 0.4% Hetastarch, 0.5% Hetastarch, 0.6% Hetastarch, 0.7% Hetastarch, 0.8% Hetastarch, 0.9% Hetastarch, 1.0% Hetastarch, 1.1% Hetastarch, 1.2% Hetastarch, 1.3% Hetastarch, 1.4% Hetastarch, 1.5% Hetastarch, 1.6% Hetastarch, 1.7% Hetastarch, 1.8% Hetastarch, 1.9% Hetastarch, 2.0% Hetastarch, 2.1% Hetastarch, 2.2% Hetastarch, 2.3% Hetastarch, 2.4% Hetastarch, 2.5% Hetastarch, 2.6% Hetastarch, 2.7% Hetastarch, 2.8% Hetastarch, 2.9% Hetastarch, 3.0% Hetastarch, 3.1% Hetastarch, 3.2% Hetastarch, 3.3% Hetastarch, 3.4% Hetastarch, 3.5% Hetastarch, 3.6% Hetastarch, 3.7% Hetastarch, 3.8% Hetastarch, 3.9% Hetastarch, 4.0% Hetastarch, 4.1% Hetastarch, 4.2% Hetastarch, 4.3% Hetastarch, 4.4% Hetastarch, 4.5% Hetastarch, 4.6% Hetastarch, 4.7% Hetastarch, 4.8% Hetastarch, 4.9% Hetastarch, 5.0% Hetastarch, 5.1% Hetastarch, 5.2% Hetastarch, 5.3% Hetastarch, 5.4% Hetastarch, 5.5% Hetastarch, 5.6% Hetastarch, 5.7% Hetastarch, 5.8% Hetastarch, 5.9% Hetastarch, 6.0% Hetastarch, 6.1% Hetastarch, 6.2% Hetastarch, 6.3% Hetastarch, 6.4% Hetastarch, 6.5% Hetastarch, 6.6% Hetastarch, 6.7% Hetastarch, 6.8% Hetastarch, 6.9% Hetastarch, 7.0% Hetastarch, 7.1% Hetastarch, 7.2% Hetastarch, 7.3% Hetastarch, 7.4% Hetastarch, 7.5% Hetastarch, 7.6% Hetastarch, 7.7% Hetastarch, 7.8% Hetastarch, 7.9% Hetastarch, 8.0% Hetastarch, 8.1% Hetastarch, 8.2% Hetastarch, 8.3% Hetastarch, 8.4% Hetastarch, 8.5% Hetastarch, 8.6% Hetastarch, 8.7% Hetastarch, 8.8% Hetastarch, 8.9% Hetastarch, 9.0% Hetastarch, 9.1% Hetastarch, 9.2% Hetastarch, 9.3% Hetastarch, 9.4% Hetastarch, 9.5% Hetastarch, 9.6% Hetastarch, 9.7% Hetastarch, 9.8% Hetastarch, 9.9% Hetastarch, 10% Hetastarch, 10.5% Hetastarch, 11% Hetastarch, 11.5% Hetastarch, 12% Hetastarch, 12.5% Hetastarch, 13% Hetastarch, 13.5% Hetastarch, 14% Hetastarch, 14.5% Hetastarch, 15% Hetastarch, 15.5% Hetastarch, 16% Hetastarch, 16.5% Hetastarch, 17% Hetastarch, 17.5% Hetastarch, 18% Hetastarch, 18.5% Hetastarch, 19% Hetastarch, 20% Hetastarch, 20.5% Hetastarch, 21% Hetastarch, 21.5% Hetastarch, 22% Hetastarch, 22.5% Hetastarch, 23% Hetastarch, 23.5% Hetastarch, 24% Hetastarch, 24.5% Hetastarch, 25% Hetastarch, 25.5% Hetastarch, 26% Hetastarch, 26.5% Hetastarch, 27% Hetastarch, 27.5% Hetastarch, 28% Hetastarch, 28.5% Hetastarch, 29% Hetastarch, 29.5% Hetastarch, 30% Hetastarch, 40% Hetastarch or less than 50% Hetastarch.

In some aspects, the concentration of HSA in the cryopreservation medium can be less than 0.1% HSA, 0.2% HSA, 0.3% HSA, 0.4% HSA, 0.5% HSA, 0.6% HSA, 0.7% HSA, 0.8% HSA, 0.9% HSA, 1.0% HSA, 1.1% HSA, 1.2% HSA, 1.3% HSA, 1.4% HSA, 1.5% HSA, 1.6% HSA, 1.7% HSA, 1.8% HSA, 1.9% HSA, 2.0% HSA, 2.1% HSA, 2.2% HSA, 2.3% HSA, 2.4% HSA, 2.5% HSA, 2.6% HSA, 2.7% HSA, 2.8% HSA, 2.9% HSA, 3.0% HSA, 3.1% HSA, 3.2% HSA, 3.3% HSA, 3.4% HSA, 3.5% HSA, 3.6% HSA, 3.7% HSA, 3.8% HSA, 3.9% HSA, 4.0% HSA, 4.1% HSA, 4.2% HSA, 4.3% HSA, 4.4% HSA, 4.5% HSA, 4.6% HSA, 4.7% HSA, 4.8% HSA, 4.9% HSA, 5.0% HSA, 5.1% HSA, 5.2% HSA, 5.3% HSA, 5.4% HSA, 5.5% HSA, 5.6% HSA, 5.7% HSA, 5.8% HSA, 5.9% HSA, 6.0% HSA, 6.1% HSA, 6.2% HSA, 6.3% HSA, 6.4% HSA, 6.5% HSA, 6.6% HSA, 6.7% HSA, 6.8% HSA, 6.9% HSA, 7.0% HSA, 7.1% HSA, 7.2% HSA, 7.3% HSA, 7.4% HSA, 7.5% HSA, 7.6% HSA, 7.7% HSA, 7.8% HSA, 7.9% HSA, 8.0% HSA, 8.1% HSA, 8.2% HSA, 8.3% HSA, 8.4% HSA, 8.5% HSA, 8.6% HSA, 8.7% HSA, 8.8% HSA, 8.9% HSA, 9.0% HSA, 9.1% HSA, 9.2% HSA, 9.3% HSA, 9.4% HSA, 9.5% HSA, 9.6% HSA, 9.7% HSA, 9.8% HSA, 9.9% HSA, 10% HSA, 10.5% HSA, 11% HSA, 11.5% HSA, 12% HSA, 12.5% HSA, 13% HSA, 13.5% HSA, 14% HSA, 14.5% HSA, 15% HSA, 15.5% HSA, 16% HSA, 16.5% HSA, 17% HSA, 17.5% HSA, 18% HSA, 18.5% HSA, 19% HSA, 20% HSA, 20.5% HSA, 21% HSA, 21.5% HSA, 22% HSA, 22.5% HSA, 23% HSA, 23.5% HSA, 24% HSA, 24.5% HSA, 25% HSA, 25.5% HSA, 26% HSA, 26.5% HSA, 27% HSA, 27.5% HSA, 28% HSA, 28.5% HSA, 29% HSA, 29.5% HSA, 30% HSA, 40% HSA or less than 50% HSA.

In some aspects, the cryopreservation medium can contain other components in order to cryopreserve the hematopoietic cells in accordance with and for use with the methods described herein.

For the methods described herein, hematopoietic cells can be frozen (e.g., cryopreserved) after isolation or after isolation and purification from the donor. In some aspects, hematopoietic cells can be cryopreserved using a cryopreservation medium and method of cryopreservation known to those of skill in the art. In some aspects, the hematopoietic cells can be cryopreserved using a cryopreservation medium containing dimethylsulfoxide (DMSO), fetal calf serum (FCS) and RPMI medium.

In some aspects, the concentration of DMSO in the cryopreservation medium can be less than 0.1% DMSO, 0.2% DMSO, 0.3% DMSO, 0.4% DMSO, 0.5% DMSO, 0.6% DMSO, 0.7% DMSO, 0.8% DMSO, 0.9% DMSO, 1.0% DMSO, 1.1% DMSO, 1.2% DMSO, 1.3% DMSO, 1.4% DMSO, 1.5% DMSO, 1.6% DMSO, 1.7% DMSO, 1.8% DMSO, 1.9% DMSO, 2.0% DMSO, 2.1% DMSO, 2.2% DMSO, 2.3% DMSO, 2.4% DMSO, 2.5% DMSO, 2.6% DMSO, 2.7% DMSO, 2.8% DMSO, 2.9% DMSO, 3.0% DMSO, 3.1% DMSO, 3.2% DMSO, 3.3% DMSO, 3.4% DMSO, 3.5% DMSO, 3.6% DMSO, 3.7% DMSO, 3.8% DMSO, 3.9% DMSO, 4.0% DMSO, 4.1% DMSO, 4.2% DMSO, 4.3% DMSO, 4.4% DMSO, 4.5% DMSO, 4.6% DMSO, 4.7% DMSO, 4.8% DMSO, 4.9% DMSO, 5.0% DMSO, 5.1% DMSO, 5.2% DMSO, 5.3% DMSO, 5.4% DMSO, 5.5% DMSO, 5.6% DMSO, 5.7% DMSO, 5.8% DMSO, 5.9% DMSO, 6.0% DMSO, 6.1% DMSO, 6.2% DMSO, 6.3% DMSO, 6.4% DMSO, 6.5% DMSO, 6.6% DMSO, 6.7% DMSO, 6.8% DMSO, 6.9% DMSO, 7.0% DMSO, 7.1% DMSO, 7.2% DMSO, 7.3% DMSO, 7.4% DMSO, 7.5% DMSO, 7.6% DMSO, 7.7% DMSO, 7.8% DMSO, 7.9% DMSO, 8.0% DMSO, 8.1% DMSO, 8.2% DMSO, 8.3% DMSO, 8.4% DMSO, 8.5% DMSO, 8.6% DMSO, 8.7% DMSO, 8.8% DMSO, 8.9% DMSO, 9.0% DMSO, 9.1% DMSO, 9.2% DMSO, 9.3% DMSO, 9.4% DMSO, 9.5% DMSO, 9.6% DMSO, 9.7% DMSO, 9.8% DMSO, 9.9% DMSO, 10% DMSO, 10.5% DMSO, 11% DMSO, 11.5% DMSO, 12% DMSO, 12.5% DMSO, 13% DMSO, 13.5% DMSO, 14% DMSO, 14.5% DMSO, 15% DMSO, 15.5% DMSO, 16% DMSO, 16.5% DMSO, 17% DMSO, 17.5% DMSO, 18% DMSO, 18.5% DMSO, 19% DMSO, 20% DMSO, 20.5% DMSO, 21% DMSO, 21.5% DMSO, 22% DMSO, 22.5% DMSO, 23% DMSO, 23.5% DMSO, 24% DMSO, 24.5% DMSO, 25% DMSO, 25.5% DMSO, 26% DMSO, 26.5% DMSO, 27% DMSO, 27.5% DMSO, 28% DMSO, 28.5% DMSO, 29% DMSO, 29.5% DMSO, 30% DMSO, 40% DMSO or less than 50% DMSO.

In some aspects, the concentration of FCS in the cryopreservation medium can be greater than 1.0% FCS, 2.0% FCS, 3.0% FCS, 4.0% FCS, 5.0% FCS, 6.0% FCS, 7.0% FCS, 8.0% FCS, 9.0% FCS, 10% FCS, 10.5% FCS, 11% FCS, 11.5% FCS, 12% FCS, 12.5% FCS, 13% FCS, 13.5% FCS, 14% FCS, 14.5% FCS, 15% FCS, 15.5% FCS, 16% FCS, 16.5% FCS, 17% FCS, 17.5% FCS, 18% FCS, 18.5% FCS, 19% FCS, 20% FCS, 20.5% FCS, 21% FCS, 21.5% FCS, 22% FCS, 22.5% FCS, 23% FCS, 23.5% FCS, 24% FCS, 24.5% FCS, 25% FCS, 25.5% FCS, 26% FCS, 26.5% FCS, 27% FCS, 27.5% FCS, 28% FCS, 28.5% FCS, 29% FCS, 29.5% FCS, 30% FCS, 30.5% FCS, 31% FCS, 31.5% FCS, 32% FCS, 32.5% FCS, 33% FCS, 33.5% FCS, 34% FCS, 34.5% FCS, 35% FCS, 35.5% FCS, 36% FCS, 36.5% FCS, 37% FCS, 37.5% FCS, 38% FCS, 38.5% FCS, 39% FCS, 40% FCS, 40.5% FCS, 41% FCS, 41.5% FCS, 42% FCS, 42.5% FCS, 43% FCS, 43.5% FCS, 44% FCS, 44.5% FCS, 45% FCS, 45.5% FCS, 46% FCS, 46.5% FCS, 47% FCS, 47.5% FCS, 48% FCS, 48.5% FCS, 49% FCS, 50% FCS, 50.5% FCS, 51% FCS, 51.5% FCS, 52% FCS, 52.5% FCS, 53% FCS, 53.5% FCS, 54% FCS, 54.5% FCS, 55% FCS, 55.5% FCS, 56% FCS, 56.5% FCS, 57% FCS, 57.5% FCS, 58% FCS, 58.5% FCS, 59% FCS, 60% FCS, 60.5% FCS, 61% FCS, 61.5% FCS, 62% FCS, 62.5% FCS, 63% FCS, 63.5% FCS, 64% FCS, 64.5% FCS, 65% FCS, 65.5% FCS, 66% FCS, 66.5% FCS, 67% FCS, 67.5% FCS, 68% FCS, 68.5% FCS, 69% FCS, 70% FCS, 70.5% FCS, 71% FCS, 71.5% FCS, 72% FCS, 72.5% FCS, 73% FCS, 73.5% FCS, 74% FCS, 74.5% FCS, 75% FCS, 75.5% FCS, 76% FCS, 76.5% FCS, 77% FCS, 77.5% FCS, 78% FCS, 78.5% FCS, 79% FCS or greater than 80% FCS.

In some aspects, the concentration of RPMI in the cryopreservation medium can be greater than 1.0% RPMI, 2.0% RPMI, 3.0% RPMI, 4.0% RPMI, 5.0% RPMI, 6.0% RPMI, 7.0% RPMI, 8.0% RPMI, 9.0% RPMI, 10% RPMI, 10.5% RPMI, 11% RPMI, 11.5% RPMI, 12% RPMI, 12.5% RPMI, 13% RPMI, 13.5% RPMI, 14% RPMI, 14.5% RPMI, 15% RPMI, 15.5% RPMI, 16% RPMI, 16.5% RPMI, 17% RPMI, 17.5% RPMI, 18% RPMI, 18.5% RPMI, 19% RPMI, 20% RPMI, 20.5% RPMI, 21% RPMI, 21.5% RPMI, 22% RPMI, 22.5% RPMI, 23% RPMI, 23.5% RPMI, 24% RPMI, 24.5% RPMI, 25% RPMI, 25.5% RPMI, 26% RPMI, 26.5% RPMI, 27% RPMI, 27.5% RPMI, 28% RPMI, 28.5% RPMI, 29% RPMI, 29.5% RPMI, 30% RPMI, 30.5% RPMI, 31% RPMI, 31.5% RPMI, 32% RPMI, 32.5% RPMI, 33% RPMI, 33.5% RPMI, 34% RPMI, 34.5% RPMI, 35% RPMI, 35.5% RPMI, 36% RPMI, 36.5% RPMI, 37% RPMI, 37.5% RPMI, 38% RPMI, 38.5% RPMI, 39% RPMI, 40% RPMI, 40.5% RPMI, 41% RPMI, 41.5% RPMI, 42% RPMI, 42.5% RPMI, 43% RPMI, 43.5% RPMI, 44% RPMI, 44.5% RPMI, 45% RPMI, 45.5% RPMI, 46% RPMI, 46.5% RPMI, 47% RPMI, 47.5% RPMI, 48% RPMI, 48.5% RPMI, 49% RPMI, 50% RPMI, 50.5% RPMI, 51% RPMI, 51.5% RPMI, 52% RPMI, 52.5% RPMI, 53% RPMI, 53.5% RPMI, 54% RPMI, 54.5% RPMI, 55% RPMI, 55.5% RPMI, 56% RPMI, 56.5% RPMI, 57% RPMI, 57.5% RPMI, 58% RPMI, 58.5% RPMI, 59% RPMI, 60% RPMI, 60.5% RPMI, 61% RPMI, 61.5% RPMI, 62% RPMI, 62.5% RPMI, 63% RPMI, 63.5% RPMI, 64% RPMI, 64.5% RPMI, 65% RPMI, 65.5% RPMI, 66% RPMI, 66.5% RPMI, 67% RPMI, 67.5% RPMI, 68% RPMI, 68.5% RPMI, 69% RPMI, 70% RPMI, 70.5% RPMI, 71% RPMI, 71.5% RPMI, 72% RPMI, 72.5% RPMI, 73% RPMI, 73.5% RPMI, 74% RPMI, 74.5% RPMI, 75% RPMI, 75.5% RPMI, 76% RPMI, 76.5% RPMI, 77% RPMI, 77.5% RPMI, 78% RPMI, 78.5% RPMI, 79% RPMI or greater than 80% RPMI.

In some aspects, the cryopreservation medium can contain other components in order to cryopreserve the hematopoietic cells in accordance with and for use with the methods described herein.

Cryopreservation of hematopoietic cells includes a process of controlled rate freezing the cells once contained within cryopreservation medium. In some aspects, a cryofreezer equipped with a computer to control the rate and temperatures of controlled rate freezing can be used to perform cryopreservation of the hematopoietic cells. For example, the hematopoietic cells can be placed in a cryofreezer with a chamber temperature at or below 6.5° C. The computer can control the rate and temperatures of controlled rate freezing such that the cryofreezer reaches a temperature of at least or below −130° C. such that the hematopoietic cells are preserved in manner in accordance with the methods described herein. In some aspects, the cryofreezer uses liquid nitrogen to control the temperature of the freezer at which the hematopoietic cells are stored.

In some aspects, the hematopoietic cells can be cryopreserved and stored in a cryofreezer prior to delivery to the recipient. In some aspects, the hematopoietic cells can be cryopreserved for less than one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days or less than 60 days.

In some aspects, the hematopoietic cells can be cryopreserved for less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months or less than 60 months.

In some aspects, the hematopoietic cells can be cryopreserved for less than one year, two years, three years, four years, five years, six years, seven years, eight years, nine years, ten years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 51 years, 52 years, 53 years, 54 years, 55 years, 56 years, 57 years, 58 years, 59 years or less than 60 years.

In some aspects, the hematopoietic cells can be cryopreserved for more than one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days or more 60 days.

In some aspects, the hematopoietic cells can be cryopreserved for more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months, 24 months, 25 months, 26 months, 27 months, 28 months, 29 months, 30 months, 31 months, 32 months, 33 months, 34 months, 35 months, 36 months, 37 months, 38 months, 39 months, 40 months, 41 months, 42 months, 43 months, 44 months, 45 months, 46 months, 47 months, 48 months, 49 months, 50 months, 51 months, 52 months, 53 months, 54 months, 55 months, 56 months, 57 months, 58 months, 59 months or for more than 60 months.

In some aspects, the hematopoietic cells can be cryopreserved for more than one year, two years, three years, four years, five years, six years, seven years, eight years, nine years, ten years, 11 years, 12 years, 13 years, 14 years, 15 years, 16 years, 17 years, 18 years, 19 years, 20 years, 21 years, 22 years, 23 years, 24 years, 25 years, 26 years, 27 years, 28 years, 29 years, 30 years, 31 years, 32 years, 33 years, 34 years, 35 years, 36 years, 37 years, 38 years, 39 years, 40 years, 41 years, 42 years, 43 years, 44 years, 45 years, 46 years, 47 years, 48 years, 49 years, 50 years, 51 years, 52 years, 53 years, 54 years, 55 years, 56 years, 57 years, 58 years, 59 years or more than 60 years.

In some aspects, cryopreservation can result in hematopoietic cell death which is determined upon thawing of the cells prior to infusion into the recipient. Using conventional methods of determining cell death (e.g., trypan blue staining, flow cytometry, etc.) known to those of skill in the art, the percent of dead cells in batch of cryopreserved hematopoietic cells can be determined. In some aspects, after thawing cryopreserved cells, there can be less than 0.1% dead cells, 0.2% dead cells, 0.3% dead cells, 0.4% dead cells, 0.5% dead cells, 0.6% dead cells, 0.7% dead cells, 0.8% dead cells, 0.9% dead cells, 1.0% dead cells, 1.1% dead cells, 1.2% dead cells, 1.3% dead cells, 1.4% dead cells, 1.5% dead cells, 1.6% dead cells, 1.7% dead cells, 1.8% dead cells, 1.9% dead cells, 2.0% dead cells, 2.1% dead cells, 2.2% dead cells, 2.3% dead cells, 2.4% dead cells, 2.5% dead cells, 2.6% dead cells, 2.7% dead cells, 2.8% dead cells, 2.9% dead cells, 3.0% dead cells, 3.1% dead cells, 3.2% dead cells, 3.3% dead cells, 3.4% dead cells, 3.5% dead cells, 3.6% dead cells, 3.7% dead cells, 3.8% dead cells, 3.9% dead cells, 4.0% dead cells, 4.1% dead cells, 4.2% dead cells, 4.3% dead cells, 4.4% dead cells, 4.5% dead cells, 4.6% dead cells, 4.7% dead cells, 4.8% dead cells, 4.9% dead cells, 5.0% dead cells, 5.1% dead cells, 5.2% dead cells, 5.3% dead cells, 5.4% dead cells, 5.5% dead cells, 5.6% dead cells, 5.7% dead cells, 5.8% dead cells, 5.9% dead cells, 6.0% dead cells, 6.1% dead cells, 6.2% dead cells, 6.3% dead cells, 6.4% dead cells, 6.5% dead cells, 6.6% dead cells, 6.7% dead cells, 6.8% dead cells, 6.9% dead cells, 7.0% dead cells, 7.1% dead cells, 7.2% dead cells, 7.3% dead cells, 7.4% dead cells, 7.5% dead cells, 7.6% dead cells, 7.7% dead cells, 7.8% dead cells, 7.9% dead cells, 8.0% dead cells, 8.1% dead cells, 8.2% dead cells, 8.3% dead cells, 8.4% dead cells, 8.5% dead cells, 8.6% dead cells, 8.7% dead cells, 8.8% dead cells, 8.9% dead cells, 9.0% dead cells, 9.1% dead cells, 9.2% dead cells, 9.3% dead cells, 9.4% dead cells, 9.5% dead cells, 9.6% dead cells, 9.7% dead cells, 9.8% dead cells, 9.9% dead cells, 10% dead cells, 10.5% dead cells, 11% dead cells, 11.5% dead cells, 12% dead cells, 12.5% dead cells, 13% dead cells, 13.5% dead cells, 14% dead cells, 14.5% dead cells, 15% dead cells, 15.5% dead cells, 16% dead cells, 16.5% dead cells, 17% dead cells, 17.5% dead cells, 18% dead cells, 18.5% dead cells, 19% dead cells, 20% dead cells, 20.5% dead cells, 21% dead cells, 21.5% dead cells, 22% dead cells, 22.5% dead cells, 23% dead cells, 23.5% dead cells, 24% dead cells, 24.5% dead cells, 25% dead cells, 25.5% dead cells, 26% dead cells, 26.5% dead cells, 27% dead cells, 27.5% dead cells, 28% dead cells, 28.5% dead cells, 29% dead cells, 29.5% dead cells, 30% dead cells, 40% dead cells or less than 50% dead cells.

Hematopoietic Stem Cells

Hematopoietic cells can be freshly prepared or previously frozen (e.g., cryopreserved) prior to administration to a recipient as described herein. Methods of cryopreservation are described elsewhere herein. In some aspects, one aliquot of hematopoietic cells can be thawed. In other aspects, more than one aliquot of hematopoietic cells can be thawed. For example, at least one aliquot, two aliquots, three aliquots, four aliquots, five aliquots, six aliquots, seven aliquots, eight aliquots, nine aliquots, 10 aliquots, 11 aliquots, 12 aliquots, 13 aliquots, 14 aliquots, 15 aliquots, 16 aliquots, 17 aliquots, 18 aliquots, 19 aliquots, 20 aliquots, 21 aliquots, 22 aliquots, 23 aliquots, 24 aliquots, 25 aliquots, 26 aliquots, 27 aliquots, 28 aliquots, 29 aliquots, 30 aliquots, 31 aliquots, 32 aliquots, 33 aliquots, 34 aliquots, 35 aliquots, 36 aliquots, 37 aliquots, 38 aliquots, 39 aliquots, 40 aliquots, 41 aliquots, 42 aliquots, 43 aliquots, 44 aliquots, 45 aliquots, 46 aliquots, 47 aliquots, 48 aliquots, 49 aliquots, 50 aliquots or more than 50 aliquots of hematopoietic cells can be thawed.

In some aspects, freshly prepared engineered hematopoietic cells can be expanded ex vivo using methods known to those of skill in the art. In other aspects, previously frozen engineered hematopoietic cells can be expanded ex vivo using methods known to those of skill in the art. In some aspects, either freshly prepared or previously frozen engineered hematopoietic cells can be expanded ex vivo by use of at least one growth factor. In some aspects, more than one growth factor can be used to expand the cells. For example, a growth factor can be activin A, ADAM-10, Angiogenin, Angiopoietin-1, Angiopoietin-2, Angiopoietin-3, Angiopoietin-4, BIO, Bone Morpohogenetic Protien-2, Bone Morpohogenetic Protien-3, Bone Morphogenetic Protien-4, Bone Morpohogenetic Protien-5, Bone Morphogenetic Protien-6, Bone Morphogenetic Protien-7, Brain-derived neurotrophic factor, E-cadherin, Fc chimera, cathepsin G, ch2 inhibitor II, epidermal growth factor, eotaxin, eotaxin-2, eotaxin-3, Fas, fibroblast growth factor-4, fibroblast growth factor-5, fibroblast growth factor-6, fibroblast growth factor-8b, fibroblast growth factor-8c, fibroblast growth factor-9, fibroblast growth factor-10, fibroblast growth factor-17, fibroblast growth factor-18, fibroblast growth factor, fibroblast growth factor acidic, fibroblast growth factor basic, fibroblast growth factor basic fragment 1-24 bovine, fibroblast growth factor receptor 1a, fibroblast growth factor receptor 1b, fibroblast growth factor receptor 2a, fibroblast growth factor receptor 2b fibroblast growth factor receptor 3a, fibroblast growth factor receptor 4, flt-3, flk-2 ligand, granulocyte colony stimulating factor, granulocyte-macrophage colony stimulating factor, GROa, GROb, heparin-binding EGF-like growth factor, heregulin-a1 EGF domain, heregulin-b1 EGF domain, heregulin B, insulin-like growth factor-1, insulin-like growth factor-II fragment 33-40, insulin-like growth factor binding protein-2, insulin-like growth factor-1, insulin-like growth factor II, interferon a, interferon aA, interferon aA/D, interferon b, interferon g, interferon, interferon g receptor 1, interleukin-1a, interleukin-1b, interleukin soluble receptor type II, interleukin-2, interleukin-2 soluble receptor a, interleukin-2 soluble receptor b, interleukin-2 soluble receptor g, interleukin-3, interleukin-5, interleukin-6, interleukin-6 soluble receptor, interleukin-7, interleukin-8, interleukin-11, interleukin-12, leukemia inhibitory factor, LONG EGF, LONG R2 IGF-1, LYN A, macrophage inflammatory protein-1a, macrophage inflammatory protein-1b, macrophage inflammatory protein-1g, matrix metalloproteinase-1, matrix metalloproteinase-2, matrix metalloproteinase-9, MIG, monocyte chemotactic protein-1, monocyte chemotactic protein-3, monocyte chemotactic protein-4, monocyte chemotactic protein-5, nerve growth factor receptor, neurotrophin-3, neurotrophin-4, noggin, notch-1, oncostatin M, oncostatin M receptor b, osteopontin, osteoprotegrin, phenylarsine oxide, platelet-derived growth factor, platelet-derived growth factor-AB, platelet-derived growth factor-BB, platelet-derived growth factor soluble receptor a, platelet derived growth factor receptor b, anti-POU5F1, oct4, RANTES, SCF soluble receptor, L-selectin, stem cell factor, stromal cell-derived factor 1a, stromal cell-derived factor 1b, thromopoietin, Tie-1, tissue inhibitor of metalloproteinase-2, transforming growth factor-a, transforming growth factor-b1, transforming growth factor-b2, transforming growth factor-b3, transforming growth factor-b1 receptor II soluble fragment, transforming growth factor-b soluble receptor III, TrkB, vascular endothelial growth factor 120, vascular endothelial growth factor 121, vascular endothelial growth factor 164, VEGF receptor-2/Flk1/KDR and/or VEGF Receptor-3/Flt-4. The amount of each growth factor used for ex vivo expansion is known to one of skill in the art and suitable for use with the methods described herein.

In some aspects, either freshly prepared or previously frozen hematopoietic cells can be expanded ex vivo by use of at least one type of feeder cell. Any type of feeder cell can be used such that the feeder cells maintain viability of hematopoietic cells, and promote hematopoietic cell proliferation and differentiation. In some aspects, at least one growth factor combined with at least one feeder cell can be used such that the feeder cells maintain viability of hematopoietic cells, and promote hematopoietic cell proliferation and differentiation. In some aspects, feeder cells can be mitotically inactive. In some aspects, more than one type of feeder cell can be used to expand the cells. In some aspects, a type of feeder cell can be derived from adult mouse endothelial cells, embryonic mouse endothelial cells, adult mouse fibroblasts, embryonic mouse fibroblasts, adult human endothelial cells, embryonic human endothelial cells, adult human fibroblasts, embryonic human fibroblasts, adult non-human primate endothelial cells, embryonic non-human primate endothelial cells, adult non-human primate fibroblasts, embryonic non-human primate fibroblasts, adult bovine endothelial cells, embryonic bovine endothelial cells, adult bovine fibroblasts, embryonic bovine fibroblasts, adult porcine endothelial cells, embryonic porcine endothelial cells, adult porcine fibroblasts, embryonic porcine fibroblasts and the like.

In some aspects, feeder cells can be modified. For example, the modifications can be genetic. In some aspects, feeder cells can express non-native genes, repress expression of native genes or overexpress native genes. For example, feeder cells can express LacZ, GFP, RFP or the like.

The hematopoietic stem cells that can be used with the methods described herein can be supplied in the form of a pharmaceutical composition, comprising an isotonic excipient prepared under sufficiently sterile conditions for administration to a subject in need thereof. Choice of the cellular excipient and any accompanying elements of the composition can be adapted in accordance with the route and device used for administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

In some aspects, the pharmaceutical composition can contain agents which enhance engraftment of the hematopoietic cells in the recipient. In other aspects, the pharmaceutical composition can contain agents which do not affect engraftment of the hematopoietic cells in the recipient. In some aspects, the pharmaceutical composition can contain agents which prevent a negative reaction of the recipient to the hematopoietic cells. For example, any agent as mentioned above can be a cytokine, a chemokine, a growth factor, an excipient, a carrier, an inert molecule, an antibody or a fragment thereof, a small molecule, a drug, an agonist, an antagonist, a chemical or the like. Any agent used in a pharmaceutical composition of hematopoietic cells in the recipient is physiologically acceptable.

A variety of methods can be used to deliver hematopoietic cells to the recipient and any method known to one of skill in the art can be applied to the hematopoietic cells described herein. For example, the hematopoietic cells can be delivered to the recipient by injection using a needle, catheter, central line or the like. In some aspects, the hematopoietic cells can be delivered intravascularly, intravenously, intraarterially, intracranially, intraperitoneally, subcutaneously, intramuscularly, intraorbitally, or through any source which permits the hematopoietic cells to home to an appropriate site in the recipient such that the hematopoietic cells persist, regenerate and differentiate in the recipient.

The hematopoietic cells can also be accompanied with one or more other ingredients that facilitate the engraftment or functional mobilization of the cells. For example, ingredients can include matrix proteins that support the cells, promote adhesion of the cells, or complementary cell types (e.g., endothelial cells).

In some aspects, the hematopoietic cells can home to an organ, a tissue or a cell type within the recipient. For example, an organ can the brain, thyroid, eyes, skin, lungs, pancreas, spleen, bladder, prostate, kidneys, stomach, liver, heart, adrenal glands, bronchi, large intestine, small intestine, spinal cord, bone, bone marrow, pituitary gland, salivary gland, gall bladder, larynx, lymph nodes, prostate, skeletal muscles, appendix, esophagus, parathyroid glands, trachea, urethra, ovaries, testicles, uterus, ureters, fallopian tubes, or any gland in the body. In some aspects, a tissue or a cell type can be part of an organ. In some aspects, a tissue or a cell type can be a derived from an organ. In some aspects, a tissue or a cell type can be isolated from an organ.

Non-Myeloablative Conditioning

In some aspects, the recipient can be treated with non-myeloablative conditioning. In some aspects, non-myeloablative conditioning can be performed using methods known to those of skill in the art. In other aspects, recipients can receive non-myeloablative conditioning that includes a plurality of agents. In some aspects, the agents can include thymoglobulin (ATG), a T-cell depleting agent and/or radiation.

In some aspects, ATG can be delivered intravenously. In some aspects, a single dose of ATG can be delivered to the recipient. In other aspects, the recipient can receive more than one dose of ATG. For example, a recipient can receive at least one dose of ATG, two doses of ATG, three doses of ATG, four doses of ATG, five doses of ATG, six doses of ATG, seven doses of ATG, eight doses of ATG, nine doses of ATG, 10 doses of ATG, 11 doses of ATG, 12 doses of ATG, 13 doses of ATG, 14 doses of ATG, 15 doses of ATG, 16 doses of ATG, 17 doses of ATG, 18 doses of ATG, 19 doses of ATG, or at least 20 doses of ATG.

In some aspects, each dose of ATG can be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg or at least 20 mg/kg.

ATG can be administered on the same day of HCT. In some aspects, the plurality of ATG doses can be administered over a period of time after HCT. In some aspects, the plurality of ATG doses can be administered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

The ATG can be administered intravascularly, intravenously, intraarterially, intracranially, intraperitoneally, subcutaneously, intramuscularly, intraorbitally, orally, topically, or through any source which permits proper metabolism of the ATG by the recipient.

Corticosteroid therapy can be given as medication prior to administration of ATG. In some aspects, solumedrol can be administered although any corticosteroid known to one of skill in the art sufficient to reduce side effects of ATG can be used at an effective dose. In some aspects, the corticosterioid can be administered on the same day as ATG is administered. For example, solumedrol can be administered at a dose within the range of 0-40 mg, 5-50 mg, 10-60 mg, 15-65 mg, 20-70 mg, 25-75 mg, 30-80 mg, 35-85 mg, 40-90 mg, 45-95 mg, 50-100 mg, 55-105 mg, 60-110 mg, 65-115 mg, 70-120 mg, 75-125 mg, 80-130 mg, 85-135 mg, 90-140 mg, 95-145 mg, 100-150 mg, 105-155 mg, 110-160 mg, 115-165 mg, 120-170 mg, 125-175 mg, 130-180 mg, 135-185 mg, 140-190 mg, 145-195 mg or 150-200 mg.

Following the final dose of ATG administered to the recipient, prednisone can be administered. In some aspects, a single dose of prednisone can be administered. In other aspects, more than one dose of prednisone can be administered. For example, multiple doses of prednisone can be administered according to a tapering course or a constant course.

In some aspects, for a tapering course, the first dose of prednisone can start at 100 mg/d and then the dose reduced by 5 mg/d until constant at 5 mg/d for at least 15 days, the first dose of prednisone can start at 90 mg/d and reduced by 5 mg/d until constant for at least 15 days, the first dose of prednisone can start at 80 mg/d and reduced by 5 mg/d until constant for at least 15 days, the first dose of prednisone can start at 70 mg/d and reduced by 5 mg/d until constant for at least 15 days, the first dose of prednisone can start at 60 mg/d and reduced by 5 mg/d until constant for at least 15 days, the first dose of prednisone can start at 50 mg/d and reduced by 5 mg/d until constant for at least 15 days, the first dose of prednisone can start at 40 mg/d and reduced by 5 mg/d until constant for at least 15 days, the first dose of prednisone can start at 30 mg/d and reduced by 5 mg/d until constant for at least 15 days, the first dose of prednisone can start at 20 mg/d and reduced by 5 mg/d until constant for at least 15 days or the first dose of prednisone can start at 10 mg/d and reduced by 5 mg/d until constant for at least 15 days. In some aspects, for a constant course, the doses of prednisone can be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 15 days.

In some aspects, for a tapering course, the first dose of prednisone can start at 100 mg/d and reduced by 5 mg/d until constant for at least 30 days, the first dose of prednisone can start at 90 mg/d and reduced by 5 mg/d until constant for at least 30 days, the first dose of prednisone can start at 80 mg/d and reduced by 5 mg/d until constant for at least 30 days, the first dose of prednisone can start at 70 mg/d and reduced by 5 mg/d until constant for at least 30 days, the first dose of prednisone can start at 60 mg/d and reduced by 5 mg/d until constant for at least 30 days, the first dose of prednisone can start at 50 mg/d and reduced by 5 mg/d until constant for at least 30 days, the first dose of prednisone can start at 40 mg/d and reduced by 5 mg/d until constant for at least 30 days, the first dose of prednisone can start at 30 mg/d and reduced by 5 mg/d until constant for at least 30 days, the first dose of prednisone can start at 20 mg/d and reduced by 5 mg/d until constant for at least 30 days or the first dose of prednisone can start at 10 mg/d and reduced by 5 mg/d until constant for at least 30 days. In some aspects, for a constant course, the doses of prednisone can be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 30 days.

In some aspects, for a tapering course, the first dose of prednisone can start at 100 mg/d and reduced by 5 mg/d until constant for at least 45 days, the first dose of prednisone can start at 90 mg/d and reduced by 5 mg/d until constant for at least 45 days, the first dose of prednisone can start at 80 mg/d and reduced by 5 mg/d until constant for at least 45 days, the first dose of prednisone can start at 70 mg/d and reduced by 5 mg/d until constant for at least 45 days, the first dose of prednisone can start at 60 mg/d and reduced by 5 mg/d until constant for at least 45 days, the first dose of prednisone can start at 50 mg/d and reduced by 5 mg/d until constant for at least 45 days, the first dose of prednisone can start at 40 mg/d and reduced by 5 mg/d until constant for at least 45 days, the first dose of prednisone can start at 30 mg/d and reduced by 5 mg/d until constant for at least 45 days, the first dose of prednisone can start at 20 mg/d and reduced by 5 mg/d until constant for at least 45 days or the first dose of prednisone can start at 10 mg/d and reduced by 5 mg/d until constant for at least 45 days. In some aspects, for a constant course, the doses of prednisone can be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 45 days.

In some aspects, for a tapering course, the first dose of prednisone can start at 100 mg/d and reduced by 5 mg/d until constant for at least 60 days, the first dose of prednisone can start at 90 mg/d and reduced by 5 mg/d until constant for at least 60 days, the first dose of prednisone can start at 80 mg/d and reduced by 5 mg/d until constant for at least 60 days, the first dose of prednisone can start at 70 mg/d and reduced by 5 mg/d until constant for at least 60 days, the first dose of prednisone can start at 60 mg/d and reduced by 5 mg/d until constant for at least 60 days, the first dose of prednisone can start at 50 mg/d and reduced by 5 mg/d until constant for at least 60 days, the first dose of prednisone can start at 40 mg/d and reduced by 5 mg/d until constant for at least 60 days, the first dose of prednisone can start at 30 mg/d and reduced by 5 mg/d until constant for at least 60 days, the first dose of prednisone can start at 20 mg/d and reduced by 5 mg/d until constant for at least 60 days or the first dose of prednisone can start at 10 mg/d and reduced by 5 mg/d until constant for at least 60 days. In some aspects, for a constant course, the doses of prednisone can be 100 mg/d, 90 mg/d, 80 mg/d, 70 mg/d, 60 mg/d, 50 mg/d, 40 mg/d, 30 mg/d, 20 mg/d, 10 mg/d or 5 mg/d for at least 60 days.

The corticosteroid and/or prednisone can be administered intravascularly, intravenously, intraarterially, intracranially, intraperitoneally, subcutaneously, intramuscularly, intraorbitally, orally, topically, or through any source which permits proper metabolism of the corticosteroid and/or prednisone by the recipient.

In some aspects, any T-cell depleting agent known to one of skill in the art can be used as a portion of a non-myeloablative conditioning regime for the recipient. In some aspects, the T-cell depleting agent can be an anti-T-cell monoclonal antibody or a T-cell depleting drug (e.g., fludarabine). In some aspects, a single T-cell depleting agent is administered to the recipient. In other aspects, more than one T-cell depleting agent is administered to the recipient.

In some aspects, a T-cell depleting agent can be delivered intravenously. In some aspects, a single dose of a T-cell depleting agent can be delivered to the recipient. In other aspects, the recipient can receive more than one dose of a T-cell depleting agent. For example, a recipient can receive at least one dose of a T-cell depleting agent, two doses of a T-cell depleting agent, three doses of a T-cell depleting agent, four doses of a T-cell depleting agent, five doses of a T-cell depleting agent, six doses of a T-cell depleting agent, seven doses of a T-cell depleting agent, eight doses of a T-cell depleting agent, nine doses of a T-cell depleting agent, 10 doses of a T-cell depleting agent, 11 doses of a T-cell depleting agent, 12 doses of a T-cell depleting agent, 13 doses of a T-cell depleting agent, 14 doses of a T-cell depleting agent, 15 doses of a T-cell depleting agent, 16 doses of a T-cell depleting agent, 17 doses of a T-cell depleting agent, 18 doses of a T-cell depleting agent, 19 doses of a T-cell depleting agent, or 20 doses of a T-cell depleting agent.

A T-cell depleting agent can be administered on the same day of solid-organ transplantation. In some aspects, the plurality of T-cell depleting agent doses can be delivered over a period of time after organ transplantation. In some aspects, the plurality of T-cell depleting agent doses can be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some aspects, the T-cell depleting agent is delivered intra-operatively before the transplanted organ is perfused with host blood. In other aspects, the T-cell depleting agent is delivered intra-operatively after the transplanted organ is perfused with host blood. In some aspects, the T-cell depleting agent is delivered intravenously before the transplanted organ is perfused with host blood. In other aspects, the T-cell depleting agent is delivered intravenously after the transplanted organ is perfused with host blood. In some aspects, the T-cell depleting agent is delivered intra-arterially before the transplanted organ is perfused with host blood. In other aspects, the T-cell depleting agent is delivered intra-arterially after the transplanted organ is perfused with host blood. In some aspects, the T-cell depleting agent is delivered subcutaneously before the transplanted organ is perfused with host blood. In other aspects, the T-cell depleting agent is delivered subcutaneously after the transplanted organ is perfused with host blood. In some aspects, the T-cell depleting agent is delivered intraperitoneally before the transplanted organ is perfused with host blood. In other aspects, the T-cell depleting agent is delivered intraperitoneally after the transplanted organ is perfused with host blood.

In some aspects, fludarabine can be delivered intravenously. In some aspects, a single dose of fludarabine can be delivered to the recipient. In other aspects, the recipient can receive more than one dose of fludarabine. For example, a recipient can receive at least one dose of fludarabine, two doses of fludarabine, three doses of fludarabine, four doses of fludarabine, five doses of fludarabine, six doses of fludarabine, seven doses of fludarabine, eight doses of fludarabine, nine doses of fludarabine, 10 doses of fludarabine, 11 doses of fludarabine, 12 doses of fludarabine, 13 doses of fludarabine, 14 doses of fludarabine, 15 doses of fludarabine, 16 doses of fludarabine, 17 doses of fludarabine, 18 doses of fludarabine, 19 doses of fludarabine, or at least 20 doses of fludarabine.

In some aspects, each dose of fludarabine can be at least 0.1 mg/m2/d, 0.2 mg/m2/d, 0.3 mg/m2/d, 0.4 mg/m2/d, 0.5 mg/m2/d, 0.6 mg/m2/d, 0.7 mg/m2/d, 0.8 mg/m2/d, 0.9 mg/m2/d, 1.0 mg/m2/d, 1.1 mg/m2/d, 1.2 mg/m2/d, 1.3 mg/m2/d, 1.4 mg/m2/d, 1.5 mg/m2/d, 1.6 mg/m2/d, 1.7 mg/m2/d, 1.8 mg/m2/d, 1.9 mg/m2/d, 2.0 mg/m2/d, 2.1 mg/m2/d, 2.2 mg/m2/d, 2.3 mg/m2/d, 2.4 mg/m2/d, 2.5 mg/m2/d, 2.6 mg/m2/d, 2.7 mg/m2/d, 2.8 mg/m2/d, 2.9 mg/m2/d, 3.0 mg/m2/d, 3.1 mg/m2/d, 3.2 mg/m2/d, 3.3 mg/m2/d, 3.4 mg/m2/d, 3.5 mg/m2/d, 3.6 mg/m2/d, 3.7 mg/m2/d, 3.8 mg/m2/d, 3.9 mg/m2/d, 4.0 mg/m2/d, 4.1 mg/m2/d, 4.2 mg/m2/d, 4.3 mg/m2/d, 4.4 mg/m2/d, 4.5 mg/m2/d, 4.6 mg/m2/d, 4.7 mg/m2/d, 4.8 mg/m2/d, 4.9 mg/m2/d, 5.0 mg/m2/d, 5.1 mg/m2/d, 5.2 mg/m2/d, 5.3 mg/m2/d, 5.4 mg/m2/d, 5.5 mg/m2/d, 5.6 mg/m2/d, 5.7 mg/m2/d, 5.8 mg/m2/d, 5.9 mg/m2/d, 6.0 mg/m2/d, 6.1 mg/m2/d, 6.2 mg/m2/d, 6.3 mg/m2/d, 6.4 mg/m2/d, 6.5 mg/m2/d, 6.6 mg/m2/d, 6.7 mg/m2/d, 6.8 mg/m2/d, 6.9 mg/m2/d, 7.0 mg/m2/d, 7.1 mg/m2/d, 7.2 mg/m2/d, 7.3 mg/m2/d, 7.4 mg/m2/d, 7.5 mg/m2/d, 7.6 mg/m2/d, 7.7 mg/m2/d, 7.8 mg/m2/d, 7.9 mg/m2/d, 8.0 mg/m2/d, 8.1 mg/m2/d, 8.2 mg/m2/d, 8.3 mg/m2/d, 8.4 mg/m2/d, 8.5 mg/m2/d, 8.6 mg/m2/d, 8.7 mg/m2/d, 8.8 mg/m2/d, 8.9 mg/m2/d, 9.0 mg/m2/d, 9.1 mg/m2/d, 9.2 mg/m2/d, 9.3 mg/m2/d, 9.4 mg/m2/d, 9.5 mg/m2/d, 9.6 mg/m2/d, 9.7 mg/m2/d, 9.8 mg/m2/d, 9.9 mg/m2/d, 10 mg/m2/d, 10.5 mg/m2/d, 11 mg/m2/d, 11.5 mg/m2/d, 12 mg/m2/d, 12.5 mg/m2/d, 13 mg/m2/d, 13.5 mg/m2/d, 14 mg/m2/d, 14.5 mg/m2/d, 15 mg/m2/d, 15.5 mg/m2/d, 16 mg/m2/d, 16.5 mg/m2/d, 17 mg/m2/d, 17.5 mg/m2/d, 18 mg/m2/d, 18.5 mg/m2/d, 19 mg/m2/d, 20 mg/m2/d, 20.5 mg/m2/d, 21 mg/m2/d, 21.5 mg/m2/d, 22 mg/m2/d, 22.5 mg/m2/d, 23 mg/m2/d, 23.5 mg/m2/d, 24 mg/m2/d, 24.5 mg/m2/d, 25 mg/m2/d, 25.5 mg/m2/d, 26 mg/m2/d, 26.5 mg/m2/d, 27 mg/m2/d, 27.5 mg/m2/d, 28 mg/m2/d, 28.5 mg/m2/d, 29 mg/m2/d, 30 mg/m2/d, 30.5 mg/m2/d, 31 mg/m2/d, 31.5 mg/m2/d, 32 mg/m2/d, 32.5 mg/m2/d, 33 mg/m2/d, 33.5 mg/m2/d, 34 mg/m2/d, 34.5 mg/m2/d, 35 mg/m2/d, 35.5 mg/m2/d, 36 mg/m2/d, 36.5 mg/m2/d, 37 mg/m2/d, 37.5 mg/m2/d, 38 mg/m2/d, 38.5 mg/m2/d, 39 mg/m2/d, 40 mg/m2/d, 40.5 mg/m2/d, 41 mg/m2/d, 41.5 mg/m2/d, 42 mg/m2/d, 42.5 mg/m2/d, 43 mg/m2/d, 43.5 mg/m2/d, 44 mg/m2/d, 44.5 mg/m2/d, 45 mg/m2/d, 45.5 mg/m2/d, 46 mg/m2/d, 46.5 mg/m2/d, 47 mg/m2/d, 47.5 mg/m2/d, 48 mg/m2/d, 48.5 mg/m2/d, 49 mg/m2/d, 50 mg/m2/d, 50.5 mg/m2/d, 51 mg/m2/d, 51.5 mg/m2/d, 52 mg/m2/d, 52.5 mg/m2/d, 53 mg/m2/d, 53.5 mg/m2/d, 54 mg/m2/d, 54.5 mg/m2/d, 55 mg/m2/d, 55.5 mg/m2/d, 56 mg/m2/d, 56.5 mg/m2/d, 57 mg/m2/d, 57.5 mg/m2/d, 58 mg/m2/d, 58.5 mg/m2/d, 59 mg/m2/d or at least 60 mg/m2/d.

Fludarabine can be administered on the same day of solid-organ transplantation. In some aspects, the plurality of fludarabine doses can be delivered over a period of time after organ transplantation. In some aspects, the plurality of fludarabine doses can be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some aspects, the fludarabine is delivered intra-operatively before the transplanted organ is perfused with host blood. In other aspects, the fludarabine is delivered intra-operatively after the transplanted organ is perfused with host blood. In some aspects, the fludarabine is delivered intravenously before the transplanted organ is perfused with host blood. In other aspects, the fludarabine is delivered intravenously after the transplanted organ is perfused with host blood. In some aspects, the fludarabine is delivered intra-arterially before the transplanted organ is perfused with host blood. In other aspects, the fludarabine is delivered intra-arterially after the transplanted organ is perfused with host blood. In some aspects, the fludarabine is delivered subcutaneously before the transplanted organ is perfused with host blood. In other aspects, the fludarabine is delivered subcutaneously after the transplanted organ is perfused with host blood. In some aspects, the fludarabine is delivered intraperitoneally before the transplanted organ is perfused with host blood. In other aspects, the fludarabine is delivered intraperitoneally after the transplanted organ is perfused with host blood.

During non-myeloablative conditioning, recipients can be monitored for the development of conditions associated with non-myeloablative conditioning. Such diseases include neutropenia (e.g., granulocytes<2,000/mL), thrombocytopenia (e.g., platelets<60,000/mL) and secondary infections. In some aspects, G-CSF (e.g., 10 µg/kg/day) can be administered for neutropenia. In some aspects, any standard treatment known to one of skill in the art can be administered for thrombocytopenia or any secondary infections.

In some aspects, non-myeloablative conditioning can be temporarily stopped if a recipient develops neutropenia, thrombocytopenia or any secondary infections. Non-myeloablative conditioning can be continued once neutropenia, thrombocytopenia and or any secondary infections are resolved. In some aspects, if the recipient has a white blood count below 1,000 cells/mm$^3$, the recipient can be treated with G-CSF (e.g., 10 µg/kg/day) following non-myeloablative conditioning.

Immunosuppression and Graft Management

Following HCT, the recipient can receive an immunosuppressive regimen. The immunosuppressive regimen can have two phases, an induction phase and a maintenance phase. Induction and maintenance phase strategies can use different medicines at doses adjusted to achieve target therapeutic levels to enhance long term transplant persistence in the recipient. In some aspects, the induction phase can begin perioperatively. In some aspects, the induction phase can begin immediately after transplantation. In some aspects, the induction phase can be both perioperative and immediately after transplantation. In some aspects, the immunosuppressive regimen can continue as a maintenance therapy until the recipient achieves chimerism. For example, chimerism can be stable mixed chimerism as described herein.

In some aspects, the immunosuppressive regimen can include one agent. In other aspects, the immunosuppressive regimen can include more than one agent. For example, suitable agents for the immunosuppressive regimen can include a calcineurin inhibitor and/or an adjuvant. In some aspects, the primary immunosuppressive agents include calcineurin inhibitors, which combine with binding proteins to inhibit calcineurin activity. In some aspects, the calcineurin inhibitor can be tacrolimus, cyclosporine A, or any calcineurin inhibitor known to one of skill in the art and can be administered to the recipient at a dose effective to provide targeted immunosuppression as a calcineurin inhibitor.

In some aspects, cyclosporine A can be withdrawn from the recipient after a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months.

In some aspects, cyclosporine A can be withdrawn from the recipient after a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months.

In some aspects, the dose of cyclosporine A can slowly be tapered if the recipient meets clinical criteria for lack of rejection and GVHD. For example, the total amount of the cyclosporine A administered can be reduced over time. In some aspects, tapering of the cyclosporine A can occur for a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months such that at the end of the tapering regime, the dose of the cyclosporine A is tapered to zero. In some aspects, tapering of the cyclosporine A can occur for a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months such that at the end of the tapering regime, the dose of the cyclosporine A is tapered to zero.

In some aspects, the cyclosporine A can be delivered by a single dose to the recipient. In other aspects, the recipient can receive more than one dose of cyclosporine A. For example, a recipient can receive at least one dose of cyclosporine A, two doses of cyclosporine A, three doses of cyclosporine A, four doses of cyclosporine A, five doses of cyclosporine A, six doses of cyclosporine A, seven doses of cyclosporine A, eight doses of cyclosporine A, nine doses of cyclosporine A, 10 doses of cyclosporine A, 11 doses of cyclosporine A, 12 doses of cyclosporine A, 13 doses of cyclosporine A, 14 doses of cyclosporine A, 15 doses of cyclosporine A, 16 doses of cyclosporine A, 17 doses of cyclosporine A, 18 doses of cyclosporine A, 19 doses of cyclosporine A, or 20 doses of cyclosporine A.

In some aspects, a plurality of cyclosporine A doses can be delivered over a period of time after organ transplantation. In some aspects, the plurality of cyclosporine A doses can be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some aspects, each dose of cyclosporine A can be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or at least 10 mg/kg.

In some aspects, the amount of cyclosporine A administered to the patient can be determined by the amount of the cyclosporine A in the bloodstream. For example, the cyclosporine A can be administered at a dose to achieve a range of 0-40 mg, 5-50 mg, 10-60 mg, 15-65 mg, 20-70 mg, 25-75 mg, 30-80 mg, 35-85 mg, 40-90 mg, 45-95 mg, 50-100 mg, 55-105 mg, 60-110 mg, 65-115 mg, 70-120 mg, 75-125 mg, 80-130 mg, 85-135 mg, 90-140 mg, 95-145 mg, 100-150 mg, 105-155 mg, 110-160 mg, 115-165 mg, 120-170 mg, 125-175 mg, 130-180 mg, 135-185 mg, 140-190 mg, 145-195 mg, 150-200 mg, 160-210 mg, 170-220 mg, 180-230 mg, 190-240 mg, 200-250 mg, 210-260 mg, 220-270 mg, 230-280 mg, 240-290 mg, 250-300 mg, 260-310 mg, 270-320 mg, 280-330 mg, 290-340 mg, 300-350 mg, 310-360 mg, 320-370 mg, 330-380 mg, 340-390 mg, 350-400 mg, 360-410 mg, 370-420 mg, 380-430 mg, 390-440 mg, 400-450 mg, 410-460 mg, 420-470 mg, 430-480 mg, 440-490 mg, 450-500 mg, 46-510 mg, 470-520 mg, 480-530 mg, 490-540 mg, 500-550 mg, 510-560 mg, 520-570 mg, 530-580 mg, 540-590 mg, 550-600 mg, 560-610 mg, 570-620 mg, 580-630 mg, 590-640 mg, 600-650 mg, 610-660 mg, 620-670 mg, 630-680 mg, 640-690 mg, 650-700 mg or more than 700 mg.

In some aspects, tacrolimus can be withdrawn from the recipient after a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months. In some aspects, the dose of tacrolimus can slowly be tapered providing the recipient meets clinical criteria for lack of rejection and GVHD. For example, the total amount of tacrolimus administered can be reduced over time. In some aspects, tapering of tacrolimus can occur for a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months such that at the end of the tapering regime, the dose of tacrolimus is tapered to zero.

In some aspects, tacrolimus can be withdrawn from the recipient after a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months. In some aspects, the dose of tacrolimus can slowly be tapered providing the recipient meets clinical criteria for lack of rejection and GVHD. For example, the total amount of tacrolimus administered can be reduced over time. In some aspects, tapering of tacrolimus can occur for a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months months or more than 24 months such that at the end of the tapering regime, the dose of tacrolimus is tapered to zero.

In some aspects, tacrolimus can be delivered by a single to the recipient. In other aspects, the recipient can receive more than one dose of Tacrolimus. For example, a recipient can receive at least one dose of Tacrolimus, two doses of Tacrolimus, three doses of Tacrolimus, four doses of Tacrolimus, five doses of Tacrolimus, six doses of Tacrolimus, seven doses of Tacrolimus, eight doses of Tacrolimus, nine doses of Tacrolimus, 10 doses of Tacrolimus, 11 doses of Tacrolimus, 12 doses of Tacrolimus, 13 doses of Tacrolimus, 14 doses of Tacrolimus, 15 doses of Tacrolimus, 16 doses of Tacrolimus, 17 doses of Tacrolimus, 18 doses of Tacrolimus, 19 doses of Tacrolimus, or at least 20 doses of Tacrolimus.

In some aspects, a plurality of tacrolimus doses can be delivered over a period of time after organ transplantation. In some aspects, the plurality of tacrolimus doses can be delivered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2d days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

In some aspects, each dose of tacrolimus can be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, or at least10 mg/kg.

In some aspects, the amount of tacrolimus administered to the patient is determined by the amount of tacrolimus in the bloodstream. For example, tacrolimus can be administered at a dose to achieve a range of 0-40 mg, 5-50 mg, 10-60 mg, 15-65 mg, 20-70 mg, 25-75 mg, 30-80 mg, 35-85 mg, 40-90 mg, 45-95 mg, 50-100 mg, 55-105 mg, 60-110 mg, 65-115 mg, 70-120 mg, 75-125 mg, 80-130 mg, 85-135 mg, 90-140 mg, 95-145 mg, 100-150 mg, 105-155 mg, 110-160 mg, 115-165 mg, 120-170 mg, 125-175 mg, 130-180 mg, 135-185 mg, 140-190 mg, 145-195 mg, 150-200 mg, 160-210 mg, 170-220 mg, 180-230 mg, 190-240 mg, 200-250 mg, 210-260 mg, 220-270 mg, 230-280 mg, 240-290 mg, 250-300 mg, 260-310 mg, 270-320 mg, 280-330 mg, 290-340 mg, 300-350 mg, 310-360 mg, 320-370 mg, 330-380 mg, 340-390 mg, 350-400 mg, 360-410 mg, 370-420 mg, 380-430 mg, 390-440 mg, 400-450 mg, 410-460 mg, 420-470 mg, 430-480 mg, 440-490 mg, 450-500 mg, 46-510 mg, 470-520 mg, 480-530 mg, 490-540 mg, 500-550 mg, 510-560 mg, 520-570 mg, 530-580 mg, 540-590 mg, 550-600 mg, 560-610 mg, 570-620 mg, 580-630 mg, 590-640 mg, 600-650 mg, 610-660 mg, 620-670 mg, 630-680 mg, 640-690 mg, 650-700 mg or more than 700 mg.

The levels of either cyclosporine or tacrolimus in the recipient can be monitored. At the onset of immunosuppression, the levels of either cyclosporine or tacrolimus can be, for example, in the range of 0-15 ng/mL, 5-15 ng/mL, 10-20 ng/mL, 15-25 ng/mL, 20-30 ng/mL, 25-35 ng/mL, 30-40 ng/mL, 35-45 ng/mL or 40-50 ng/mL in the recipient. In some aspects, the levels of either cyclosporine or tacrolimus can be reduced after a period of time in the recipient. For example, the period of time can be less than one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks or less than 33 weeks. In some aspects, the levels of either cyclosporine or tacrolimus can be reduced to within the range of 0-1 ng/mL, 0.5-1.5 ng/mL, 1.0-2.0 ng/mL, 1.5-2.5 ng/mL, 2.0-3.0 ng/mL, 2.5-3.5 ng/mL, 3.0-4.0 ng/mL, 3.5-4.5 ng/mL, 4.0-5.0 ng/mL, 5.5-6.5 ng/mL, 6.0-7.0 ng/mL, 6.5-7.5 ng/mL, 7.0-8.0 ng/mL, 8.5-9.5 ng/mL or 9.0-10.0 ng/mL in the recipient.

In some aspects, a calcineurin inhibitor can be administered to the recipient in combination with an inhibitor of purine metabolism (e.g., mycophenolate mofetil). For example, cyclosporine A and mycophenolate mofetil can be used in the aspect of kidney transplantation.

In some aspects, the adjuvant can be withdrawn from the recipient after a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of more than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or more than 24 months such that at the end of the tapering regime, the dose of the purine metabolism inhibitor is tapered to zero.

In some aspects, the adjuvant can be withdrawn from the recipient after a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of less than one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or less than 24 months such that at the end of the tapering regime, the dose of the purine metabolism inhibitor is tapered to zero.

Adjuvant agents can be used to enhance immunosuppression while decreasing the dose and toxicity of other individual agents that are part of the immunosuppressive regimen. In some aspects, adjuvant agents can be combined with a calcineurin inhibitor. For example, adjuvant agents can include steroids, azathioprine, mycophenolate mofetil, sirolimus, an antibody or any adjuvant agent known to one of skill in the art and can be administered to the recipient at a dose effective to enhance immunosuppression.

In some aspects, antibody-based therapy can be used to avoid or reduce the dose of calcineurin inhibitors in the immunosuppressive regimen. For example, antibody-based therapy can include monoclonal (e.g., muromonab-CD3) antibodies, polyclonal antibodies and/or anti-CD25 antibodies (e.g., basiliximab, daclizumab). In some aspects, antibody-based therapy can be administered during the early post-transplant period. For example, early post-transplant can be up to 8 weeks following the transplant.

Graft management can include preventing, inhibiting or suppressing acute rejection with immunosuppressive drugs. In some aspects, multiple agents can be used to prevent, inhibit or suppress episodes of acute rejection. For example, an agent can be a steroid. In some aspects, one or more than one steroid can be used to prevent, inhibit or suppress episodes of acute rejection. Any steroid known to one of skill in the art suitable for preventing, inhibiting or suppressing acute rejection can be used. For example, any dose, mode of administration and duration of administration for any steroid known to one of skill in the art suitable for preventing, inhibiting or suppressing acute rejection can be used. In some aspects, administration of the steroid can be tapered to a maintenance dose.

For example, an agent can be antithymocyte globulin. In some aspects, antithymocyte globulin can be used to prevent, inhibit or suppress episodes of acute rejection. Any dose, mode of administration and duration of administration for antithymocyte globulin suitable for preventing, inhibiting or suppressing acute rejection can be used. In some aspects, administration of antithymocyte globulin can be tapered to a maintenance dose.

For example, an agent can be muromonab-CD3. In some aspects, muromonab-CD3 can be used to prevent, inhibit or suppress episodes of acute rejection. Any dose, mode of administration and duration of administration for muromonab-CD3 suitable for preventing, inhibiting or suppressing acute rejection can be used. In some aspects, administration of muromonab-CD3 can be tapered to a maintenance dose.

Chimerism

Following HCT, the recipient can be monitored for chimerism. Recipients who exhibit greater than 95% donor cells in a given blood cell lineage by any analysis to determine chimerism at any time post-transplantation can be classified as having full donor chimerism. In some aspects, mixed chimerism can be greater than 1% donor-derived cells of a given lineage but less than 95% donor-derived DNA.

Individuals who exhibit mixed chimerism can be further classified according to the evolution of chimerism, where improving mixed chimerism can be a continuous increase in the proportion of donor cells over a period of time (e.g., at least a 6-months). In some aspects, stable mixed chimerism can include fluctuations in the percentage of recipienT-cells over time, without complete loss of donor cells.

Chimerism is defined as greater than 1% recipient DNA. In some aspects, chimerism can include a percentage of cells derived from the donor and a percentage of cells derived from the recipient. In some aspects, chimerism is more than 70% of the cells in the recipient being derived from the donor. In other aspects, chimerism is more than 10% of the cells in the recipient being derived from the donor, more than 15% of the cells in the recipient being derived from the donor, more than 20% of the cells in the recipient being derived from the donor, more than 25% of the cells in the recipient being derived from the donor, more than 30% of the cells in the recipient being derived from the donor, more than 35% of the cells in the recipient being derived from the donor, more than 40% of the cells in the recipient being derived from the donor, more than 45% of the cells in the recipient being derived from the donor, more than 50% of the cells in the recipient being derived from the donor, more than 55% of the cells in the recipient being derived from the donor, more than 56% of the cells in the recipient being derived from the donor, more than 57% of the cells in the recipient being derived from the donor, more than 58% of the cells in the recipient being derived from the donor, more than 59% of the cells in the recipient being derived from the donor, more than 60% of the cells in the recipient being derived from the donor, more than 61% of the cells in the recipient being derived from the donor, more than 62% of the cells in the recipient being derived from the donor, more than 63% of the cells in the recipient being derived from the donor, more than 64% of the cells in the recipient being derived from the donor, more than 65% of the cells in the recipient being derived from the donor, more than 66% of the cells in the recipient being derived from the donor, more than 67% of the cells in the recipient being derived from the donor, more than 68% of the cells in the recipient being derived from the donor, more than 69% of the cells in the recipient being derived from the donor, more than 70% of the cells in the recipient being derived from the donor, more than 71% of the cells in the recipient being derived from the donor, more than 72% of the cells in the recipient being derived from the donor, more than 73% of the cells in the recipient being derived from the donor, more than 74% of the cells in the recipient being derived from the donor, more than 75% of the cells in the recipient being derived from the donor, more than 76% of the cells in the recipient being derived from the donor, more than 77% of the cells in the recipient being derived from the donor, more than 78% of the cells in the recipient being derived from the donor, more than 79% of the cells in the recipient being derived from the donor, more than 80% of the cells in the recipient being derived from the donor, more than 81% of the cells in the recipient being derived from the donor, more than 82% of the cells in the recipient being derived from the donor, more than 83% of the cells in the recipient being derived from the donor, more than 84% of the cells in the recipient being derived from the donor, more than 85% of the cells in the recipient being derived from the donor, more than 86% of the cells in the recipient being derived from the donor, more than 87% of the cells in the recipient being derived from the donor, more than 88% of the cells in the recipient being derived from the donor, more than 89% of the cells in the recipient being derived from the donor, more than 90% of the cells in the recipient being derived from the donor, more than 91% of the cells in the recipient being derived from the donor, more than 92% of the cells in the recipient being derived from the donor, more than 93% of the cells in the recipient being derived from the donor, more than 94% of the cells in the recipient being derived from the donor, more than 95% of the cells in the recipient being derived from the donor, more than 96% of the cells in the recipient being derived from the donor, more than 97% of the cells in the recipient being derived from the donor, more than 98% of the cells in the recipient being derived from the donor ore more than 99% of the cells in the recipient being derived from the donor.

Chimerism can be stable following HCT. In some aspects, stable chimerism lasts for at least 6 months after HCT. In some aspects, stable chimerism can persist for more than five days, more than 10 days, more than 15 days, more than 20 days, more than 25 days, more than 30 days, more than 35 days, more than 40 days, more than 45 days, more than 50 days, more than 55 days, more than 60 days, more than 65 days, more than 70 days, more than 75 days, more than 80 days, more than 85 days, more than 90 days, more than 95 days, more than 100 days, more than 105 days, more than 110 days, more than 115 days, more than 120 days, more than 125 days, more than 130 days, more than 135 days, more than 140 days, more than 145 days, more than 150 days, more than 155 days, more than 160 days, more than 165 days, more than 170 days, more than 175 days, more than 180 days, more than 185 days, more than 190 days, more than 195 days, more than 200 days, more than 205 days, more than 210 days, more than 215 days, more than 220 days, more than 225 days, more than 230 days, more than 235 days, more than 240 days, more than 245 days, more than 250 days, more than 255 days, more than 260 days, more than 265 days, more than 270 days, more than 275 days, more than 280 days, more than 285 days, more than 290 days, more than 295 days, more than 300 days, more than 305 days, more than 310 days, more than 315 days, more than 320 days, more than 325 days, more than 330 days, more than 335 days, more than 340 days, more than 345 days, more than 350 days, more than 355 days, more than 360 days, more than 365 days, more than 370 days, more than 375 days, more than 380 days, more than 385 days, more than 390 days, more than 395 days, more than 400 days, more than 405 days, more than 410 days, more than 415 days, more than 420 days, more than 425 days, more than 430 days, more than 435 days, more than 440 days, more than 445 days, more than 450 days, more than 455 days, more than 460 days, more than 465 days, more than 470 days, more than 475 days, more than 480 days, more than 485 days, more than 490 days, more than 495 days, or more than 500 days.

Chimerism can be determined by measuring the percentage of donor cells for a single cell type within the recipient. For example, chimerism can be determined by the percentage of donor-derived granulocytes in the recipient. In some aspects, chimerism can be determined by measuring the percentage of donor cells for a plurality of cell types within the recipient. For example, chimerism can be determined by the percentage of donor-derived granulocytes, natural killer cells, B-cells and T-cells in the recipient.

In some aspects, the percentage of donor-derived granulocytes in the recipient can be measured. In some aspects, the percentage of donor-derived granulocytes can be constant in the recipient after transplantation. In other aspects, the percentage of donor-derived granulocytes can not be constant in the recipient after transplantation. In other aspects, the percentage of donor-derived granulocytes changes over time in the recipient after transplantation. For example, over a period of 60 days after transplantation, the percentage of donor-derived granulocytes in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some aspects, the percentage of donor-derived natural killer cells in the recipient can be measured. In some aspects, the percentage of donor-derived natural killer cells can be constant in the recipient after transplantation. In other aspects, the percentage of donor-derived natural killer cells can not be constant in the recipient after transplantation. In other aspects, the percentage of donor-derived natural killer cells changes over time in the recipient after transplantation. For example, over a period of 60 days after transplantation, the percentage of donor-derived natural killer cells in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some aspects, the percentage of donor-derived B-cells in the recipient can be measured. In some aspects, the percentage of donor-derived B-cells can be constant in the recipient after transplantation. In other aspects, the percentage of donor-derived B-cells can not be constant in the recipient after transplantation. In other aspects, the percentage of donor-derived B-cells change over time in the recipient after transplantation. For example, over a period of 60 days after transplantation, the percentage of donor-derived B-cells in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some aspects, the percentage of donor-derived T-cells in the recipient can be measured. In some aspects, the percentage of donor-derived T-cells can Te constant in the recipient after transplantation. In other aspects, the percentage of donor-derived T-cells can not be constant in the recipient after transplantation. In other aspects, the percentage of donor-derived T-cells change over time in the recipient after transplantation. For example, over a period of 60 days after transplantation, the percentage of donor-derived T-cells in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

There are a plurality of methods of testing for chimerism that are readily available and known to those of skill in the art. Any method of testing for chimerism that distinguishes donor or recipient origin of a cell is suitable for use in the methods described herein.

In some aspects, the methods of testing for chimerism can include genetic based methods. For example, polymerase chain reaction (PCR) based methods which utilize probes can be used. In some aspects, probes for PCR based methods can be probes for microsatellite analysis. For another example, commercial kits that distinguish polymorphisms in short terminal repeat lengths of donor and host origin are readily available and known to those of skill in the art.

In some aspects, major histocompatibility complex (MHC) typing can be used for testing chimerism. For example, MHC typing can be used to test the type of cells in the blood. In some aspects, MHC typing can be used in combination with flow cytometry. In some aspect, an analysis of HLA-stained cells by flow cytometry can be performed.

The methods described herein are provided such that a recipient can achieve stable chimerism sufficient to allow withdrawal of immunosuppressive drugs. For example, withdrawal of immunosuppressive drugs can include tapering immunosuppressive drugs. In other aspects, withdrawal of immunosuppressive drugs can include immediate withdrawal of immunosuppressive drugs. In some aspects, stable chimerism persists for at least six months prior to withdrawal of immunosuppressive drugs. In other aspects, mixed chimerism persists for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some aspects, a lack of rejection episodes can coincide with chimerism prior to withdrawal of immunosuppressive drugs. In some aspects, a lack of rejection episodes can be consistent for at least six months prior to withdrawal of immunosuppressive drugs. In other aspects, a lack of rejection episodes can be consistent for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some aspects, a lack of GVHD and lack of rejection episodes coincides with chimerism prior to withdrawal of immunosuppressive drugs. In some aspects, a lack of GVHD and lack of rejection episodes can be consistent for at least six months prior to withdrawal of immunosuppressive drugs. In other aspects, a lack of GVHD and lack of rejection episodes can be consistent for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In order to determine if tapering of the immunosuppressive regimen is appropriate for the recipient, the recipient can be tested for chimerism, usually at regular intervals. For example, regular intervals can be monthly, semi-monthly, weekly, bi-monthly, annually, bi-annually or the like.

The methods described herein can be administered to a subject in the absence of GVHD. In some aspects, the methods can protect against a subject developing GVHD. Often GVHD is acute GVHD however GVHD can be chronic GVHD. In some aspects, the incidence of acute GVHD is less than 20%, 15%, 10%, 9%, 8%, 7%, 6%, 5%, 4%, 3%, 2% or less than 1% of the subjects to which the methods can be administered. In some aspects, about the incidence of acute GVHD is less than about 20%, about 15%, about 10%, about 9%, about 8%, about 7%, about 6%, about 5%, about 4%, about 3%, about 2% or less than about 1% of the subjects to which the methods can be administered. In some aspects, the incidence of chronic GVHD is less than 20%, 15%, 10%, 9%, 8%, 7%, 6%, 5%, 4%, 3%, 2% or less than 1% of the subjects to which the methods can be administered. In some aspects, about the incidence of chronic GVHD is less than about 20%, about 15%, about 10%, about 9%, about 8%, about 7%, about 6%, about 5%, about 4%, about 3%, about 2% or less than about 1% of the subjects to which the methods can be administered.

Administration of Irradiation and an Immunostimulant to a Subject

Radiation therapy can be used with the methods described herein and can include a number of modalities, including but not limited to, radiation therapy or ionizing radiation, thermal stress or thermal therapy, irreversible electroporation (IRE), oxidative stress, radiofrequency ablation, and combinations thereof. In some aspects, tumors can be pretreated with a cell-sensitizing composition prior to exposure.

In some aspects, radiation therapy can include both "sealed" and "unsealed" sources of therapeutic radiation including, but not limited to, ionizing radiation therapy, brachytherapy, sealed source radiation therapy, systemic radioisotope therapy, unsealed source radiotherapy, radionuclide therapy, external beam radiation therapy, radiation surgery, charged-particle radiotherapy, neutron radiotherapy, x-ray therapy, gamma-ray therapy, and cobalt therapy.

In some aspects, recipients can be treated with radiation. The radiation can be fractionated or unfractionated. In the aspect that a recipient is treated with more than one dose of radiation, all doses can be fractionated. In another aspect that a recipient is treated with more than one dose of irradiation, all doses can be unfractionated. In another aspect that a recipient is treated with more than one dose of irradiation, the doses can be a mix of fractionated unfractionated.

In some aspects, the radiation is delivered intraoperatively. In some aspects, the radiation is delivered intravenously. In some aspects, the radiation is delivered intraarterially. In some aspects, the radiation is delivered subcutaneously. In some aspects, the radiation is delivered intraperitoneally. In some aspects, the radiation is delivered intratumorally.

In some aspects, radiation can be delivered locally to the tumor and can be delivered at a non-curative dose. For example, the non-curative dose can be from about 1 to about 36 Gy, from about 2 to about 30 Gy, from about 3 to about 20 Gy, or around about 4, 8, 12, 16, 20 Gy. In other aspects, radiation is delivered locally to the tumor and can be delivered at a non-curative dose. For example, the non-curative dose can be from 1 to 36 Gy, from 2 to 30 Gy, from 3 to 20 Gy, or 4, 8, 12, 16, 20 Gy.

In some other aspects, radiation can be delivered locally to the tumor and can be delivered at a non-curative dose which can include shielding of the subject. For example, the non-curative dose can be from about 1 to about 36 Gy, from about 2 to about 30 Gy, from about 3 to about 20 Gy, or around about 4, 8, 12, 16, 20 Gy. In other aspects, radiation is delivered locally to the tumor and can be delivered at a non-curative dose which can include shielding of the subject. For example, the non-curative dose can be from 1 to 36 Gy, from 2 to 30 Gy, from 3 to 20 Gy, or 4, 8, 12, 16, 20 Gy. However, the use of higher doses is not necessarily contraindicated, depending on the patient status.

In some aspects, each dose of radiation can be at least 1 Gy, 2 Gy, 3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy, 20 Gy, 21 Gy, 22 Gy, 23 Gy, 24 Gy, 25 Gy, 26 Gy, 27 Gy, 28 Gy, 29 Gy, 30 Gy, 31 Gy, 32 Gy, 33 Gy, 34 Gy, 35 Gy, 36 Gy, 37 Gy, 38 Gy, 39 Gy, 40 Gy, 41 Gy, 42 Gy, 43 Gy, 44 Gy, 45 Gy, 46 Gy, 47 Gy, 48 Gy, 49 Gy or at least 50 Gy.

In other aspects, about each dose of radiation can be at least about 1 Gy, about 2 Gy, about 3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy, about 20 Gy, about 21 Gy, about 22 Gy, about 23 Gy, about 24 Gy, about 25 Gy, about 26 Gy, about 27 Gy, about 28 Gy, about 29 Gy, about 30 Gy, about 31 Gy, about 32 Gy, about 33 Gy, about 34 Gy, about 35 Gy, about 36 Gy, about 37 Gy, about 38 Gy, about 39 Gy, about 40 Gy, about 41 Gy, about 42 Gy, about 43 Gy, about 44 Gy, about 45 Gy, about 46 Gy, about 47 Gy, about 48 Gy, about 49 Gy or at least about 50 Gy.

In some aspects, a single dose of radiation can be delivered to the recipient. In other aspects, the recipient can receive more than one dose of radiation. For example, a recipient can receive at least one dose of radiation, two doses of radiation, three doses of radiation, four doses of radiation, five doses of radiation, six doses of radiation, seven doses of radiation, eight doses of radiation, nine doses of radiation, 10 doses of radiation, 11 doses of radiation, 12 doses of radiation, 13 doses of radiation, 14 doses of radiation, 15 doses of radiation, 16 doses of radiation, 17 doses of radiation, 18 doses of radiation, 19 doses of radiation, or at least 20 doses of radiation.

The radiation can be image guided. For example, clinical HIFU procedures are typically image-guided to permit treatment planning and targeting before applying a therapeutic or ablative level of ultrasound energy. When MRI is used for guidance, the technique is sometimes called Magnetic Resonance-guided Focused Ultrasound, often shortened to MRgFU. When ultrasonography is used, the technique is sometimes called Ultrasound-guided Focused Ultrasound, often shortened to USgFUS.

Using the methods described herein, a tumor nodule or tumor mass can be irradiated as described above. In some aspects, the radiation can be localized radiation at the involved field (e.g., tumor nodule or tumor mass). For example, the dose or doses of radiation administered to a subject can be sufficient to induce tumor cell death and the release of antigens therefrom. At least one tumor site can be irradiated using the methods described herein.

In some aspects, various radiation modalities can be used for this purpose, including radiofrequency ablation (RFA); light combined with a photosensitizer; X-rays, proton beam, gamma radiation; etc. Non-curative radiation therapy can be administered to the subject at a dose adequate to induce tumor cell death, but not a dose which could affect the ability for subjects to receive subsequent doses of radiation. In some aspects, the subsequent dose can be a higher treatment dose to the same site. In some aspects, the subsequent dose can be a lower treatment dose to the same site. In some aspects, the subsequent dose can be a higher treatment dose to a different site. In some aspects, the subsequent dose can be a lower treatment dose to a different site.

In other aspects, thermal stress or therapy can be used with the methods described herein. For example, thermal stress or therapy can include focused ultrasound (FUS or HIFU), radiofrequency, infrared sauna, microwave heating, induction heating, magnetic hyperthermia, infusion of warmed liquids, or direct application of heat. The thermal stress can include local hyperthermia and/or regional hyperthermia. The thermal stress or thermal therapy can also include exposure to sub-lethal heat. For example, a hyperthermia modality can heat a cancer cell too much lower therapeutic temperatures compared to other tissue ablation techniques. For instance, the elevation above a normal body temperature of 37° C. will fall within a range of 42° C. to 45° C.

Irreversible electroporation uses a series of microsecond electrical pulses instead of extreme heat, freezing, radiation or microwave energy-to permanently open cell membranes in tumors. Once the cell membrane pores are opened, the death of the targeted cancer cells is induced. Surrounding veins, nerves and ducts within the targeted area are largely unaffected by the process around them.

The methods described herein further include administration of an immunostimulant to a subject following irradiation. In some aspects, the immunostimulant can be administered to the subject less than 24 hours after administration of radiation. For example, the immunostimulant can be administered to the subject less than 22 hours after administration of radiation, less than 20 hours after administration of radiation, less than 18 hours after administration of radiation, less than 16 hours after administration of radiation, less than 14 hours after administration of radiation, less than 12 hours after administration of radiation, less than 10 hours after administration of radiation, less than 8 hours after administration of radiation, less than 6 hours after administration of radiation, less than 4 hours after administration of radiation or less than 2 hours after administration of radiation. In some aspects, the immunostimulant can be administered to the subject less than about 24 hours after administration of radiation. For example, the immunostimulant can be administered to the subject less than about 22 hours after administration of radiation, less than about 20 hours after administration of radiation, less than about 18 hours after administration of radiation, less than about 16 hours after administration of radiation, less than about 14 hours after administration of radiation, less than about 12 hours after administration of radiation, less than about 10 hours after administration of radiation, less than about 8 hours after administration of radiation, less than about 6 hours after administration of radiation, less than about 4 hours after administration of radiation or less than about 2 hours after administration of radiation.

In some aspects, the immunostimulant can be administered to the subject greater than 24 hours after administration of radiation. For example, the immunostimulant can be administered to the subject greater than 22 hours after administration of radiation, greater than 20 hours after administration of radiation, greater than 18 hours after administration of radiation, greater than 16 hours after administration of radiation, greater than 14 hours after administration of radiation, greater than 12 hours after administration of radiation, greater than 10 hours after administration of radiation, greater than 8 hours after administration of radiation, greater than 6 hours after administration of radiation, greater than 4 hours after administration of radiation or greater than 2 hours after administration of radiation. In some aspects, the immunostimulant can be administered to the subject greater than about 24 hours after administration of radiation. For example, the immunostimulant can be administered to the subject greater than about 22 hours after administration of radiation, greater than about 20 hours after administration of radiation, greater than about 18 hours after administration of radiation, greater than about 16 hours after administration of radiation, greater than about 14 hours after administration of radiation, greater than about 12 hours after administration of radiation, greater than about 10 hours after administration of radiation, greater than about 8 hours after administration of radiation, greater than about 6 hours after administration of radiation, greater than about 4 hours after administration of radiation or greater than about 2 hours after administration of radiation.

In an exemplary aspect, within about 24 hours of radiation, the irradiated lymph node or skin plaque can be injected with an immunostimulant, including without limitation, immunostimulatory sequences (ISS), e.g. oligodeoxynucleotides (ODN) containing CpG. In some aspects, the ODN containing CpG can bind to the Toll-like receptor (TLR) 9 and activate dendritic cells and B-cells. Other immunostimulants of interest with the methods described herein include for example, anti-CTLA4, anti-PD1, GM-CSF, dendritic cells, and the like.

An effective dose is delivered, i.e. a dose that increases the response of allogeneic T-cells to tumor and/or allogeneic histocompatibility antigens and results in an overall decrease of tumor cells in the individual being treated. The dose of the immunostimulant delivered to a subject in need thereof is determined for each immunostimulant of the present disclosure. In some aspects, the dose of the immunostimulant can be classified in mg/injection. For example, an immunostimulant can be administered to a subject in need thereof at a dose of 0.1 mg/injection, 0.2 mg/injection, 0.3 mg/injection, 0.4 mg/injection, 0.5 mg/injection, 0.6 mg/injection, 0.7 mg/injection, 0.8 mg/injection, 0.9 mg/injection, 1.0 mg/injection, 1.1. mg/injection, 1.2 mg/injection, 1.3 mg/injection, 1.4 mg/injection, 1.5 mg/injection, 1.6 mg/injection, 1.7 mg/injection, 1.8 mg/injection, 1.9 mg/injection, 2.0 mg/injection, 2.1 mg/injection, 2.2 mg/injection, 2.3 mg/injection, 2.4 mg/injection, 2.5 mg/injection, 2.6 mg/injection, 2.7 mg/injection, 2.8 mg/injection, 2.9 mg/injection, 3.0 mg/injection, 3.1 mg/injection, 3.2 mg/injection, 3.3 mg/injection, 3.4 mg/injection, 3.5 mg/injection, 3.6 mg/injection, 3.7 mg/injection, 3.8 mg/injection, 3.9 mg/injection, 4.0 mg/injection, 4.1 mg/injection, 4.2 mg/injection, 4.3 mg/injection, 4.4. mg/injection, 4.5 mg/injection, 4.6 mg/injection, 4.7 mg/injection, 4.8 mg/injection, 4.9 mg/injection, 5.0 mg/injection, 5.1 mg/injection, 5.2 mg/injection, 5.3 mg/injection, 5.4 mg/injection, 5.5 mg/injection, 5.6 mg/injection, 5.7 mg/injection, 5.8 mg/injection, 5.9 mg/injection, 6.0 mg/injection, 6.1 mg/injection, 6.2 mg/injection, 6.3 mg/injection, 6.4 mg/injection, 6.5 mg/injection, 6.6 mg/injection, 6.7 mg/injection, 6.8 mg/injection, 6.9 mg/injection, 7.0 mg/injection, 7.1 mg/injection, 7.2 mg/injection, 7.3 mg/injection, 7.4 mg/injection, 7.5 mg/injection, 7.6 mg/injection, 7.7 mg/injection, 7.8 mg/injection, 7.9 mg/injection, 8.0 mg/injection, 8.1 mg/injection, 8.2 mg/injection, 8.3 mg/injection, 8.4 mg/injection, 8.5 mg/injection, 8.6 mg/injection, 8.7 mg/injection, 8.8 mg/injection, 8.9 mg/injection, 9.0 mg/injection, 9.1 mg/injection, 9.2 mg/injection, 9.3 mg/injection, 9.4 mg/injection, 9.5 mg/injection, 9.6 mg/injection, 9.7 mg/injection, 9.8 mg/injection, 9.9 mg/injection or up to 10 mg/injection. For another example, an immunostimulant can be administered to a subject in need thereof at a dose of about 0.1 mg/injection, about 0.2 mg/injection, about 0.3 mg/injection, about 0.4 mg/injection, about 0.5 mg/injection, about 0.6 mg/injection, about 0.7 mg/injection, about 0.8 mg/injection, about 0.9 mg/injection, about 1.0 mg/injection, about 1.1. mg/injection, about 1.2 mg/injection, about 1.3 mg/injection, about 1.4 mg/injection, about 1.5 mg/injection, about 1.6 mg/injection, about 1.7 mg/injection, about 1.8 mg/injection, about 1.9 mg/injection, about 2.0 mg/injection, about 2.1 mg/injection, about 2.2 mg/injection, about 2.3 mg/injection, about 2.4 mg/injection, about 2.5 mg/injection, about 2.6 mg/injection, about 2.7 mg/injection, about 2.8 mg/injection, about 2.9 mg/injection, about 3.0 mg/injection, about 3.1 mg/injection, about 3.2 mg/injection, about 3.3 mg/injection, about 3.4 mg/injection, about 3.5 mg/injection, about 3.6 mg/injection, about 3.7 mg/injection, about 3.8 mg/injection, about 3.9 mg/injection, about 4.0 mg/injection, about 4.1 mg/injection, about 4.2 mg/injection, about 4.3 mg/injection, about 4.4. mg/injection, about 4.5 mg/injection, about 4.6 mg/injection, about 4.7 mg/injection, about 4.8 mg/injection, about 4.9 mg/injection, about 5.0 mg/injection, about 5.1 mg/injection, about 5.2 mg/injection, about 5.3 mg/injection, about 5.4 mg/injection, about 5.5 mg/injection, about 5.6 mg/injection, about 5.7 mg/injection, about 5.8 mg/injection, about 5.9 mg/injection, about 6.0 mg/injection, about 6.1 mg/injection, about 6.2 mg/injection, about 6.3 mg/injection, about 6.4 mg/injection, about 6.5 mg/injection, about 6.6 mg/injection, about 6.7 mg/injection, about 6.8 mg/injection, about 6.9 mg/injection, about 7.0 mg/injection, about 7.1 mg/injection, about 7.2 mg/injection, about 7.3 mg/injection, about 7.4 mg/injection, about 7.5 mg/injection, about 7.6 mg/injection, about 7.7 mg/injection, about 7.8 mg/injection, about 7.9 mg/injection, about 8.0 mg/injection, about 8.1 mg/injection, about 8.2 mg/injection, about 8.3 mg/injection, about 8.4 mg/injection, about 8.5 mg/injection, about 8.6 mg/injection, about 8.7 mg/injection, about 8.8 mg/injection, about 8.9 mg/injection, about 9.0 mg/injection, about 9.1 mg/injection, about 9.2 mg/injection, about 9.3 mg/injection, about 9.4 mg/injection, about 9.5 mg/injection, about 9.6 mg/injection, about 9.7 mg/injection, about 9.8 mg/injection, about 9.9 mg/injection or up to about 10 mg/injection.

The dose of immunostimulant can be delivered at appropriate intervals, e.g. 1, 2, 3, or more injections at daily, semi-daily, weekly intervals concurrent with, or following radiation.

In some aspects, the dose of immunostimulant can be delivered to subject in need thereof at appropriate intervals with at least one injection per day concurrent with radiation. In other aspects, the dose of immunostimulant can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day concurrent with radiation. In some aspects, the dose of immunostimulant can be delivered to subject in need thereof at appropriate intervals with at least one injection per day following radiation. In other aspects, the dose of immunostimulant can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day following radiation.

In some aspects, the dose of immunostimulant can be delivered to subject in need thereof at appropriate intervals with at least one injection semi-daily concurrent with radiation. In other aspects, the dose of immunostimulant can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily concurrent with radiation. In some aspects, the dose of immunostimulant can be delivered to subject in need thereof at appropriate intervals with at least one injection semi-daily following radiation. In other aspects, the dose of immunostimulant can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily following radiation.

In some aspects, the dose of immunostimulant can be delivered to subject in need thereof at appropriate intervals with at least one injection weekly concurrent with radiation. In other aspects, the dose of immunostimulant can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly concurrent with radiation. In some aspects, the dose of immunostimulant can be delivered to subject in need thereof at appropriate intervals with at least one injection weekly following radiation. In other aspects, the dose of immunostimulant can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly following radiation.

An effective dose is delivered, i.e. a dose that increases the response of allogeneic T-cells to tumor and/or allogeneic histocompatibility antigens and results in an overall decrease of tumor cells in the individual being treated. The dose of the CpG delivered to a subject in need thereof is determined for each CpG of the present disclosure. In some aspects, the dose of the CpG can be classified in mg/injection. For example, an CpG can be administered to a subject in need thereof at a dose of 0.1 mg/injection, 0.2 mg/injection, 0.3 mg/injection, 0.4 mg/injection, 0.5 mg/injection, 0.6 mg/injection, 0.7 mg/injection, 0.8 mg/injection, 0.9 mg/injection, 1.0 mg/injection, 1.1. mg/injection, 1.2 mg/injection, 1.3 mg/injection, 1.4 mg/injection, 1.5 mg/injection, 1.6 mg/injection, 1.7 mg/injection, 1.8 mg/injection, 1.9 mg/injection, 2.0 mg/injection, 2.1 mg/injection, 2.2 mg/injection, 2.3 mg/injection, 2.4 mg/injection, 2.5 mg/injection, 2.6 mg/injection, 2.7 mg/injection, 2.8 mg/injection, 2.9 mg/injection, 3.0 mg/injection, 3.1 mg/injection, 3.2 mg/injection, 3.3 mg/injection, 3.4 mg/injection, 3.5 mg/injection, 3.6 mg/injection, 3.7 mg/injection, 3.8 mg/injection, 3.9 mg/injection, 4.0 mg/injection, 4.1 mg/injection, 4.2 mg/injection, 4.3 mg/injection, 4.4. mg/injection, 4.5 mg/injection, 4.6 mg/injection, 4.7 mg/injection, 4.8 mg/injection, 4.9 mg/injection, 5.0 mg/injection, 5.1 mg/injection, 5.2 mg/injection, 5.3 mg/injection, 5.4 mg/injection, 5.5 mg/injection, 5.6 mg/injection, 5.7 mg/injection, 5.8 mg/injection, 5.9 mg/injection, 6.0 mg/injection, 6.1 mg/injection, 6.2 mg/injection, 6.3 mg/injection, 6.4 mg/injection, 6.5 mg/injection, 6.6 mg/injection, 6.7 mg/injection, 6.8 mg/injection, 6.9 mg/injection, 7.0 mg/injection, 7.1 mg/injection, 7.2 mg/injection, 7.3 mg/injection, 7.4 mg/injection, 7.5 mg/injection, 7.6 mg/injection, 7.7 mg/injection, 7.8 mg/injection, 7.9 mg/injection, 8.0 mg/injection, 8.1 mg/injection, 8.2 mg/injection, 8.3 mg/injection, 8.4 mg/injection, 8.5 mg/injection, 8.6 mg/injection, 8.7 mg/injection, 8.8 mg/injection, 8.9 mg/injection, 9.0 mg/injection, 9.1 mg/injection, 9.2 mg/injection, 9.3 mg/injection, 9.4 mg/injection, 9.5 mg/injection, 9.6 mg/injection, 9.7 mg/injection, 9.8 mg/injection, 9.9 mg/injection or up to 10 mg/injection. For another example, an CpG can be administered to a subject in need thereof at a dose of about 0.1 mg/injection, about 0.2 mg/injection, about 0.3 mg/injection, about 0.4 mg/injection, about 0.5 mg/injection, about 0.6 mg/injection, about 0.7 mg/injection, about 0.8 mg/injection, about 0.9 mg/injection, about 1.0 mg/injection, about 1.1. mg/injection, about 1.2 mg/injection, about 1.3 mg/injection, about 1.4 mg/injection, about 1.5 mg/injection, about 1.6 mg/injection, about 1.7 mg/injection, about 1.8 mg/injection, about 1.9 mg/injection, about 2.0 mg/injection, about 2.1 mg/injection, about 2.2 mg/injection, about 2.3 mg/injection, about 2.4 mg/injection, about 2.5 mg/injection, about 2.6 mg/injection, about 2.7 mg/injection, about 2.8 mg/injection, about 2.9 mg/injection, about 3.0 mg/injection, about 3.1 mg/injection, about 3.2 mg/injection, about 3.3 mg/injection, about 3.4 mg/injection, about 3.5 mg/injection, about 3.6 mg/injection, about 3.7 mg/injection, about 3.8 mg/injection, about 3.9 mg/injection, about 4.0 mg/injection, about 4.1 mg/injection, about 4.2 mg/injection, about 4.3 mg/injection, about 4.4. mg/injection, about 4.5 mg/injection, about 4.6 mg/injection, about 4.7 mg/injection, about 4.8 mg/injection, about 4.9 mg/injection, about 5.0 mg/injection, about 5.1 mg/injection, about 5.2 mg/injection, about 5.3 mg/injection, about 5.4 mg/injection, about 5.5 mg/injection, about 5.6 mg/injection, about 5.7 mg/injection, about 5.8 mg/injection, about 5.9 mg/injection, about 6.0 mg/injection, about 6.1 mg/injection, about 6.2 mg/injection, about 6.3 mg/injection, about 6.4 mg/injection, about 6.5 mg/injection, about 6.6 mg/injection, about 6.7 mg/injection, about 6.8 mg/injection, about 6.9 mg/injection, about 7.0 mg/injection, about 7.1 mg/injection, about 7.2 mg/injection, about 7.3 mg/injection, about 7.4 mg/injection, about 7.5 mg/injection, about 7.6 mg/injection, about 7.7 mg/injection, about 7.8 mg/injection, about 7.9 mg/injection, about 8.0 mg/injection, about 8.1 mg/injection, about 8.2 mg/injection, about 8.3 mg/injection, about 8.4 mg/injection, about 8.5 mg/injection, about 8.6 mg/injection, about 8.7 mg/injection, about 8.8 mg/injection, about 8.9 mg/injection, about 9.0 mg/injection, about 9.1 mg/injection, about 9.2 mg/injection, about 9.3 mg/injection, about 9.4 mg/injection, about 9.5 mg/injection, about 9.6 mg/injection, about 9.7 mg/injection, about 9.8 mg/injection, about 9.9 mg/injection or up to about 10 mg/injection.

The dose of CpG can be delivered at appropriate intervals, e.g. 1, 2, 3, or more injections at daily, semi-daily, weekly intervals concurrent with, or following radiation.

In some aspects, the dose of CpG can be delivered to subject in need thereof at appropriate intervals with at least one injection per day concurrent with radiation. In other aspects, the dose of CpG can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day concurrent with radiation. In some aspects, the dose of CpG can be delivered to subject in need thereof at appropriate intervals with at least one injection per day following radiation. In other aspects, the dose of CpG can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day following radiation.

In some aspects, the dose of CpG can be delivered to subject in need thereof at appropriate intervals with at least one injection semi-daily concurrent with radiation. In other aspects, the dose of CpG can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily concurrent with radiation. In some aspects, the dose of CpG can be delivered to subject in need thereof at appropriate intervals with at least one injection semi-daily following radiation. In other aspects, the dose of CpG can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily following radiation.

In some aspects, the dose of CpG can be delivered to subject in need thereof at appropriate intervals with at least one injection weekly concurrent with radiation. In other aspects, the dose of CpG can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly concurrent with radiation. In some aspects, the dose of CpG can be delivered to subject in need thereof at appropriate intervals with at least one injection weekly following radiation. In other aspects, the dose of CpG can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly following radiation.

In some aspects, the subject can be tumor bearing prior to administration of the immunostimulant. In other aspects, the subject cannot be tumor bearing prior to administration of the immunostimulant. In other aspects, the subject cannot be tumor bearing prior to administration of the immunostimulant but become tumor bearing after administration of the immunostimulant. In other aspects, the subject cannot be tumor bearing prior to administration of the immunostimulant and cannot become tumor bearing after administration of the immunostimulant. For example, the tumors can be cancer tumors.

The compositions described herein can be administered to a subject in need thereof as a immunostimulant. In some aspects, the subject can be treated with one dose of the immunostimulant. In other aspects, the subject can be treated with more than one dose of the immunostimulant. For example, the subject can be treated with more than one, more than two, more than three, more than four, more than five, more than six, more than seven, more than eight, more than nine, more than ten, more than 11, more than 12, more than 13, more than 14, more than 15, more than 16, more than 17, more than 18, more than 19 or more than 20 doses of the immunostimulant. In an exemplary aspect, the subject is treated with three doses of the immunostimulant.

In the aspects that a subject receives more than one dose of the immunostimulant, time can elapse between the first dose and each subsequent dose of the immunostimulant. In some aspects, the time that elapses between the first dose an each subsequent dose of the immunostimulant can be seconds, minutes, hours, days, weeks, months or years. For example, more than one dose can be administered to the subject by intervals. In some aspects, the intervals can occur over seconds, minutes, hours, days, weeks, months or years. In some aspects, subjects can receive a booster dose. For example, the booster can be administered to the subject more than one, more than two, more than three, more than four, more than five, more than six, more than seven, more than eight, more than nine, more than ten, more than 11, more than 12, more than 13, more than 14, more than 15, more than 16, more than 17, more than 18, more than 19 or more than 20 booster doses of the immunostimulant. In an exemplary aspect, the subject can receive up to three boosters of the immunostimulant.

In some aspects, intervals can be the same between each dose of the immunostimulant. In some aspects, intervals can be the same between each booster of the immunostimulant. In some aspects, intervals can be different between each dose of the immunostimulant. In some aspects, intervals can be different between each booster of the immunostimulant.

In an exemplary aspect, more than one dose is administered to the subject over a interval of at least one day. In some aspects, the interval can be a one day, two day, three day, four day, five day, six day, seven day, eight day, nine day, ten day, 11 day, 12 day, 13 day, 14 day, 15 day, 16 day, 17 day, 18 day, 19 day, 20 day, 21 day, 22 day, 23 day, 24 day, 25 day, 26 day, 27 day, 28 day, 29 day or 30 day interval. In other aspects, the interval can be a range of days, for example, the range of days can be 1-5 days, 1-7 days, 1-10 days, 3-15 days, 5-10 days, 5-15 days, 5-20 days, 7-10 days, 7-15 days, 7-20 days, 7-25 days, 10-15 days, 10-20 days, 10-25 days, 15-20 days, 15-25 days, 15-30 days, 20-30 days, 20-35 days, 20-40 days, 20-50 days, 25-50 days, 30-50 days, 35-50 days, or 40-50 days.

Subjects can be evaluated after administration of the immunostimulant. In some aspects, the subject can be evaluated within one month (e.g., short term) of the final administration of the immunostimulant. For example, short term can be one day, two days, three days, four days, five days, six days, seven days, eight days, nine days, ten days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days or 31 days after the final administration of the immunostimulant. In some aspects, the subject can be evaluated within four month (e.g., long term) of the final administration of the immunostimulant. For example, short term can be one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or 31 weeks after the final administration of the immunostimulant.

In some aspects, the subject can receive at least one booster dose of the immunostimulant after the final administration of the immunostimulant doses. For example, at least one booster dose can be administered to the subject one week, two weeks, three weeks, four weeks, five weeks, six weeks, seven weeks, eight weeks, nine weeks, ten weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, 25 weeks, 26 weeks, 27 weeks, 28 weeks, 29 weeks, 30 weeks or 31 weeks after the final administration of the immunostimulant doses. In some aspects, the subject can receive one booster, two boosters, three boosters, four boosters, five boosters, six boosters, seven boosters, eight boosters, nine boosters, ten boosters, 11 boosters, 12 boosters, 13 boosters, 14 boosters, 15 boosters, 16 boosters, 17 boosters, 18 boosters, 19 boosters, 20 boosters, 21 boosters, 22 boosters, 23 boosters, 24 boosters, 25 boosters, 26 boosters, 27 boosters, 28 boosters, 29 boosters or 30 booster doses.

The disclosure provides in a further aspect a pharmaceutical kit comprising an intradermal administration device and an immunostimulant formulation as described herein. The device is preferably supplied already filled with the immunostimulant. Preferably the immunostimulant is in a liquid volume smaller than for conventional intramuscular immunostimulants as described herein, particularly a volume of between about 0.05 ml and 0.2 ml. Preferably the device is a short needle delivery device for administering the immunostimulant to the dermis.

The methods of the disclosure can further include administration of an immunostimulant using techniques well known to those in the art. Techniques for formulation and administration can be found in "Remington's Pharmaceutical Sciences", 18th ed., 1990, Mack Publishing Co., Easton, Pa. Suitable routes can include parenteral delivery, such as intramuscular, intradermal, subcutaneous, intramedullary injections, as well as, intrathecal, direct intraventricular, intravenous, intraperitoneal, intranasal, or intraocular injections, just to name a few. Other routes include oral or transdermal delivery.

For parenteral application, which includes intramuscular, intradermal, subcutaneous, intranasal, intracapsular, intraspinal, intrasternal, and intravenous injection, particularly suitable are injectable, sterile solutions, preferably oily or aqueous solutions, as well as suspensions, emulsions, or implants, including suppositories. Formulations fix injection can be presented in unit dosage form, e.g., in ampoules or in multi-dose containers, with an added preservative. The immunostimulant can take such forms as suspensions, solutions or emulsions in oily or aqueous vehicles, and can contain formulator agents such as suspending, stabilizing and/or dispersing agents. Alternatively, the active ingredient can be in powder form for constitution with a suitable vehicle, e.g., sterile pyrogen-free water.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

Type of Cancer and Subjects

The methods described herein can further include use of a conditioning regimen, often a low-intensity conditioning regimen, lymphoid irradiation, often total lymphoid irradiation, and administration of anti-thymocyte globulin (TLI/ATG) to a subject in need thereof. In some aspects, the methods described herein can extend the use of allogeneic hematopoietic cell transplantation (HCT) for treatment of advanced lymphoma to patients with co-morbid medical problems and/or elderly patients. The methods of the disclosure further include the administration of allogeneic immune cells to generate an anti-tumor response in a subject, and induce a systemic allogeneic anti-tumor immune response that results in tumor regression in untreated sites of disease, i.e. non-injected, non-irradiated, etc.

In some aspects the cancer is a lymphoma, where the lymphoma can be Hodgkin's Lymphoma or Non-Hodgkin's Lymphoma. In other aspects the cancer is a leukemia or myeloma with or without skin or lymph node invasion. In other aspects the cancer is a non-hematolymphoid malignancy with or without a lymph node invasion, including without limitation carcinomas, e.g. carcinoma, renal cell carcinoma, and the like.

"Subject" refers to any member without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The disclosure is intended for use involving any of the above vertebrate species, since the immune systems of all of these vertebrates operate similarly.

A subject identified as having residual, relapsed or refractory cancer with any tumor mass or nodule can be treated. In some aspects, the subject can be a healthy individual. In some aspects, the subject can be an individual with cancer, often lymphoma. For example, the individual can be a patient. In some aspects, the subject is a human individual. In other aspects, the subject is a non-human individual. For example, non-human individuals can be a non-human primate, monkey, macaque, baboon, chimpanzee, orangutan, mouse, rat, guinea pig, rabbit, horse, cow, pig, dog, cat or any individual that can have or has cancer.

Treatment of a relapsed tumor at a single site with local tumor radiation and intratumoral injection of immunostimulants can induce remission of the local tumor and remission of tumors at sites distant from the site of local tumor irradiation. In some aspects, remission can be incomplete. In other aspects, remission can be complete. For example, remission can be at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. For another example, remission can be at least about one month, about two months, about three months, about four months, about five months, about six months, about seven months, about eight months, about nine months, about ten months, about 11 months, about 12 months, about 13 months, about 14 months, about 15 months, about 16 months, about 17 months, about 18 months, about 19 months, about 20 months, about 21 months, about 22 months, about 23 months or at least 24 months. In some aspects, about the dose of the adjuvant can slowly be tapered providing the recipient meets clinical criteria for lack of rejection and GVHD. For example, about the total amount of the adjuvant administered can be reduced over time. In some aspects, about tapering of the adjuvant can occur for a duration of at least one month, about two months, about three months, about four months, about five months, about six months, about seven months, about eight months, about nine months, about ten months, about 11 months, about 12 months, about 13 months, about 14 months, about 15 months, about 16 months, about 17 months, about 18 months, about 19 months, about 20 months, about 21 months, about 22 months, about 23 months or at least 24 months.

As described herein, the disclosure also includes a kit for treatment of residual, relapsed or refractory cancer. The kit can include an immunostimulant, e.g. ISS, in an amount sufficient to induce a systemic allogeneic tumor-specific immune response that results in tumor regression in untreated sites of disease when administered to a subject at a tumor nodule or mass in combination with involved field radiation, when administered to a subject chimeric for allogeneic leukocytes. The kit can also include a reagent for HLA typing leukocytes as part of a step of determining chimerism. The kit can also include allogeneic hematopoietic stem cells, e.g., allogeneic BMT, mobilized peripheral blood cells, cord blood cells, or hematopoietic cells derived from cultured stem/progenitor cells for inducing complete or mixed chimerism.

Mouse Model

The methods described herein further include a mouse model of lymphoma relapse following HCT, often allogeneic HCT. In some aspects, the mouse model can model human clinical studies. The methods of the mouse model can include conditioning a recipient mouse, often a BALB/c genetic strain, with TLI/ATG as described herein. In some aspects, the mouse can be transplanted with MHC-matched bone marrow cells immediately following completion of a conditioning treatment. The conditioning treatment can comprise at least one dose of radiation and at least one dose of ATG. In some aspects, the conditioning treatment can comprise one dose, two doses, three doses, four doses, five doses, six doses, seven doses, eight doses, nine doses, 10 doses, 11 doses, 12 doses, 13 doses, 14 doses, 15 doses, 16 doses, 17 doses, 18 doses, 19 doses, 20 doses, 21 doses, 22 doses, 23 doses, 24 doses, 25 doses, 26 doses, 27 doses, 28 doses, 29 doses or 30 doses of radiation. In some aspects, the conditioning treatment can comprise more than one dose, two doses, three doses, four doses, five doses, six doses, seven doses, eight doses, nine doses, 10 doses, 11 doses, 12 doses, 13 doses, 14 doses, 15 doses, 16 doses, 17 doses, 18 doses, 19 doses, 20 doses, 21 doses, 22 doses, 23 doses, 24 doses, 25 doses, 26 doses, 27 doses, 28 doses, 29 doses or more than 30 doses of radiation.

In some aspects, about the conditioning treatment can comprise about one dose, about two doses, about three doses, about four doses, about five doses, about six doses, about seven doses, about eight doses, about nine doses, about 10 doses, about 11 doses, about 12 doses, about 13 doses, about 14 doses, about 15 doses, about 16 doses, about 17 doses, about 18 doses, about 19 doses, about 20 doses, about 21 doses, about 22 doses, about 23 doses, about 24 doses, about 25 doses, about 26 doses, about 27 doses, about 28 doses, about 29 doses or 30 doses of radiation. In some aspects, about the conditioning treatment can comprise more than about one dose, about two doses, about three doses, about four doses, about five doses, about six doses, about seven doses, about eight doses, about nine doses, about 10 doses, about 11 doses, about 12 doses, about 13 doses, about 14 doses, about 15 doses, about 16 doses, about 17 doses, about 18 doses, about 19 doses, about 20 doses, about 21 doses, about 22 doses, about 23 doses, about 24 doses, about 25 doses, about 26 doses, about 27 doses, about 28 doses, about 29 doses or more than 30 doses of radiation.

In some aspects, a dose of radiation can be 10 Gy, 20 Gy, 30 Gy, 40 Gy, 50 Gy, 60 Gy, 70 Gy, 80 Gy, 90 Gy, 100 Gy, 110 Gy, 120 Gy, 130 Gy, 140 Gy, 150 Gy, 160 Gy, 170 Gy, 180 Gy, 190 Gy, 200 Gy, 205 Gy, 210 Gy, 215 Gy, 220 Gy, 225 Gy, 230 Gy, 235 Gy, 240 Gy, 245 Gy, 250 Gy, 255 Gy, 260 Gy, 265 Gy, 270 Gy, 275 Gy, 280 Gy, 285 Gy, 290 Gy, 295 Gy, 300 Gy or 300 Gy. In some aspects, a dose of radiation can be more than 10 Gy, 20 Gy, 30 Gy, 40 Gy, 50 Gy, 60 Gy, 70 Gy, 80 Gy, 90 Gy, 100 Gy, 110 Gy, 120 Gy, 130 Gy, 140 Gy, 150 Gy, 160 Gy, 170 Gy, 180 Gy, 190 Gy, 200 Gy, 205 Gy, 210 Gy, 215 Gy, 220 Gy, 225 Gy, 230 Gy, 235 Gy, 240 Gy, 245 Gy, 250 Gy, 255 Gy, 260 Gy, 265 Gy, 270 Gy, 275 Gy, 280 Gy, 285 Gy, 290 Gy, 295 Gy, 300 Gy or more than 300 Gy.

In some aspects, about a dose of radiation can be 10 Gy, about 20 Gy, 30 Gy, about 40 Gy, about 50 Gy, about 60 Gy, about 70 Gy, about 80 Gy, about 90 Gy, about 100 Gy, about 110 Gy, about 120 Gy, about 130 Gy, about 140 Gy, about 150 Gy, about 160 Gy, about 170 Gy, about 180 Gy, about 190 Gy, about 200 Gy, about 205 Gy, about 210 Gy, about 215 Gy, about 220 Gy, about 225 Gy, about 230 Gy, about 235 Gy, about 240 Gy, about 245 Gy, about 250 Gy, about 255 Gy, about 260 Gy, about 265 Gy, about 270 Gy, about 275 Gy, about 280 Gy, about 285 Gy, about 290 Gy, about 295 Gy, about 300 Gy or 300 Gy. In some aspects, about a dose of radiation can be more than 10 Gy, about 20 Gy, 30 Gy, about 40 Gy, about 50 Gy, about 60 Gy, about 70 Gy, about 80 Gy, about 90 Gy, about 100 Gy, about 110 Gy, about 120 Gy, about 130 Gy, about 140 Gy, about 150 Gy, about 160 Gy, about 170 Gy, about 180 Gy, about 190 Gy, about 200 Gy, about 205 Gy, about 210 Gy, about 215 Gy, about 220 Gy, about 225 Gy, about 230 Gy, about 235 Gy, about 240 Gy, about 245 Gy, about 250 Gy, about 255 Gy, about 260 Gy, about 265 Gy, about 270 Gy, about 275 Gy, about 280 Gy, about 285 Gy, about 290 Gy, about 295 Gy, about 300 Gy or more than 300 Gy.

In some aspects, ATG can be delivered intravenously. In some aspects, a single dose of ATG can be delivered to the recipient. In other aspects, the recipient can receive more than one dose of ATG. For example, a recipient can receive at least one dose of ATG, two doses of ATG, three doses of ATG, four doses of ATG, five doses of ATG, six doses of ATG, seven doses of ATG, eight doses of ATG, nine doses of ATG, 10 doses of ATG, 11 doses of ATG, 12 doses of ATG, 13 doses of ATG, 14 doses of ATG, 15 doses of ATG, 16 doses of ATG, 17 doses of ATG, 18 doses of ATG, 19 doses of ATG, or at least 20 doses of ATG.

In some aspects, each dose of ATG can be at least 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4.0 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5.0 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6.0 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7.0 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8.0 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9.0 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg or at least 20 mg/kg.

ATG can be administered on the same day of HCT. In some aspects, the plurality of ATG doses can be administered over a period of time after HCT. In some aspects, the plurality of ATG doses can be administered over a period of at least 0.1 days, 0.2 days, 0.3 days, 0.4 days, 0.5 days, 0.6 days, 0.7 days, 0.8 days, 0.9 days, 1.0 days, 1.1 days, 1.2 days, 1.3 days, 1.4 days, 1.5 days, 1.6 days, 1.7 days, 1.8 days, 1.9 days, 2.0 days, 2.1 days, 2.2 days, 2.3 days, 2.4 days, 2.5 days, 2.6 days, 2.7 days, 2.8 days, 2.9 days, 3.0 days, 3.1 days, 3.2 days, 3.3 days, 3.4 days, 3.5 days, 3.6 days, 3.7 days, 3.8 days, 3.9 days, 4.0 days, 4.1 days, 4.2 days, 4.3 days, 4.4 days, 4.5 days, 4.6 days, 4.7 days, 4.8 days, 4.9 days, 5.0 days, 5.1 days, 5.2 days, 5.3 days, 5.4 days, 5.5 days, 5.6 days, 5.7 days, 5.8 days, 5.9 days, 6.0 days, 6.1 days, 6.2 days, 6.3 days, 6.4 days, 6.5 days, 6.6 days, 6.7 days, 6.8 days, 6.9 days, 7.0 days, 7.1 days, 7.2 days, 7.3 days, 7.4 days, 7.5 days, 7.6 days, 7.7 days, 7.8 days, 7.9 days, 8.0 days, 8.1 days, 8.2 days, 8.3 days, 8.4 days, 8.5 days, 8.6 days, 8.7 days, 8.8 days, 8.9 days, 9.0 days, 9.1 days, 9.2 days, 9.3 days, 9.4 days, 9.5 days, 9.6 days, 9.7 days, 9.8 days, 9.9 days, 10 days, 10.5 days, 11 days, 11.5 days, 12 days, 12.5 days, 13 days, 13.5 days, 14 days, 14.5 days, 15 days, 15.5 days, 16 days, 16.5 days, 17 days, 17.5 days, 18 days, 18.5 days, 19 days or at least 20 days.

The ATG can be administered intravascularly, intravenously, intraarterially, intracranially, intraperitoneally, subcutaneously, intramuscularly, intraorbitally, orally, topically, or through any source which permits proper metabolism of the ATG by the recipient.

The methods described herein can further comprise administration of lymphoma cells, often A20 lymphoma cells, to the mouse. In some aspects, the lymphoma cells can be administered 70 days following conditioning. In other aspects, the lymphoma cells can be administered one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days or 100 days following conditioning. In other aspects, about the lymphoma cells can be administered about one day, about two days, about three days, about four days, about five days, about six days, about seven days, about eight days, about nine days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days or about 100 days following conditioning.

In other aspects, the lymphoma cells can be administered at least one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days or at least 100 days following conditioning. In other aspects, about the lymphoma cells can be administered at least about one day, about two days, about three days, about four days, about five days, about six days, about seven days, about eight days, about nine days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days or at least about100 days following conditioning.

The lymphoma cells can be injected into at least one, often two sites in the mouse. In some aspects, the lymphoma cells can be injected into one, two, three, four, five, six, seven, eight, nine or ten sites in the mouse. In some aspects, the sites include the upper flank, the lower flank, the back, the cranium, the tail vein or the like.

In some aspects, the lymphoma tumors can grow for 21 days. In other aspects, the lymphoma tumors can grow for at least one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days or at least 50 days. In other aspects, the tumors can grow until a desired size is reached, often 1 cm diameter. In some aspects, the tumors can grow until 0.2 cm, 0.4 cm, 0.6 cm, 0.8 cm, 1 cm, 1.2 cm, 1.4 cm, 1.6 cm, 1.8 cm, 2.0 cm, 2.2 cm, 2.4 cm, 2.6 cm, 2.8 cm or 3.0 cm. In some aspects, about the tumors can grow until about 0.2 cm, about 0.4 cm, about 0.6 cm, about 0.8 cm, about 1 cm, about 1.2 cm, about 1.4 cm, about 1.6 cm, about 1.8 cm, about 2.0 cm, about 2.2 cm, about 2.4 cm, about 2.6 cm, about 2.8 cm or about 3.0 cm.

The methods can further include administration of local irradiation to at least one of the tumors of the mouse. In an exemplary aspect, the tumors can be given local tumor radiation (2 daily doses of 10 Gy each), and 3 injections of 30 ug CpG days 1, 7, and 14 after radiation.

In some aspects, the local irradiation can comprise one dose, two doses, three doses, four doses, five doses, six doses, seven doses, eight doses, nine doses or 10 doses of radiation. In some aspects, the local irradiation can comprise more than one dose, two doses, three doses, four doses, five doses, six doses, seven doses, eight doses, nine doses or 10 doses of radiation.

The methods can further include administration of local irradiation to at least one of the tumors of the mouse. In some aspects, about the local irradiation can comprise about one dose, about two doses, about three doses, about four doses, about five doses, about six doses, about seven doses, about eight doses, about nine doses or about 10 doses of radiation. In some aspects, the local irradiation can comprise about more than one dose, about two doses, about three doses, about four doses, about five doses, about six doses, about seven doses, about eight doses, about nine doses or about 10 doses of radiation.

In some aspects, a dose of radiation can be 1 Gy, 2 Gy,3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy or 20 Gy of radiation. In some aspects, a dose of radiation can be more than 1 Gy, 2 Gy,3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy or 20 Gy of radiation.

In some aspects, a dose of radiation can be 1 Gy, about 2 Gy,3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy or 20 Gy of radiation. In some aspects, a dose of radiation can be more than 1 Gy, about 2 Gy,3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy or 20 Gy of radiation.

The lower tumors were given local tumor radiation (2 daily doses of 10 Gy each), and 3 injections of 30 ug CpG days 1, 7, and 14 after radiation.

An effective dose is delivered, i.e. a dose that increases the response of allogeneic T-cells to tumor and/or allogeneic histocompatibility antigens and results in an overall decrease of tumor cells in the individual being treated. The dose of the CpG delivered to a subject in need thereof is determined for each CpG of the present disclosure. In some aspects, the dose of the CpG can be classified in μg/injection. For example, an CpG can be administered to a subject in need thereof at a dose of 0.1 μg/injection, 0.2 μg/injection, 0.3 μg/injection, 0.4 μg/injection, 0.5 μg/injection, 0.6 μg/injection, 0.7 μg/injection, 0.8 μg/injection, 0.9 μg/injection, 1.0 μg/injection, 1.1. μg/injection, 1.2 μg/injection, 1.3 μg/injection, 1.4 μg/injection, 1.5 μg/injection, 1.6 μg/injection, 1.7 μg/injection, 1.8 μg/injection, 1.9 μg/injection, 2.0 μg/injection, 2.1 μg/injection, 2.2 μg/injection, 2.3 μg/injection, 2.4 µg/injection, 2.5 µg/injection, 2.6 µg/injection, 2.7 µg/injection, 2.8 µg/injection, 2.9 µg/injection, 3.0 µg/injection, 3.1 µg/injection, 3.2 µg/injection, 3.3 µg/injection, 3.4 µg/injection, 3.5 µg/injection, 3.6 µg/injection, 3.7 µg/injection, 3.8 µg/injection, 3.9 µg/injection, 4.0 µg/injection, 4.1 µg/injection, 4.2 µg/injection, 4.3 µg/injection, 4.4. µg/injection, 4.5 µg/injection, 4.6 µg/injection, 4.7 µg/injection, 4.8 µg/injection, 4.9 µg/injection, 5.0 µg/injection, 5.1 µg/injection, 5.2 µg/injection, 5.3 µg/injection, 5.4 µg/injection, 5.5 µg/injection, 5.6 µg/injection, 5.7 µg/injection, 5.8 µg/injection, 5.9 µg/injection, 6.0 µg/injection, 6.1 µg/injection, 6.2 µg/injection, 6.3 µg/injection, 6.4 µg/injection, 6.5 µg/injection, 6.6 µg/injection, 6.7 µg/injection, 6.8 µg/injection, 6.9 µg/injection, 7.0 µg/injection, 7.1 µg/injection, 7.2 µg/injection, 7.3 µg/injection, 7.4 µg/injection, 7.5 µg/injection, 7.6 µg/injection, 7.7 µg/injection, 7.8 µg/injection, 7.9 µg/injection, 8.0 µg/injection, 8.1 µg/injection, 8.2 µg/injection, 8.3 µg/injection, 8.4 µg/injection, 8.5 µg/injection, 8.6 µg/injection, 8.7 µg/injection, 8.8 µg/injection, 8.9 µg/injection, 9.0 µg/injection, 9.1 µg/injection, 9.2 µg/injection, 9.3 µg/injection, 9.4 µg/injection, 9.5 µg/injection, 9.6 µg/injection, 9.7 µg/injection, 9.8 µg/injection, 9.9 µg/injection or up to 10 µg/injection. For another example, an CpG can be administered to a subject in need thereof at a dose of about 0.1 µg/injection, about 0.2 µg/injection, about 0.3 µg/injection, about 0.4 µg/injection, about 0.5 µg/injection, about 0.6 µg/injection, about 0.7 µg/injection, about 0.8 µg/injection, about 0.9 µg/injection, about 1.0 µg/injection, about 1.1. µg/injection, about 1.2 µg/injection, about 1.3 µg/injection, about 1.4 µg/injection, about 1.5 µg/injection, about 1.6 µg/injection, about 1.7 µg/injection, about 1.8 µg/injection, about 1.9 µg/injection, about 2.0 µg/injection, about 2.1 µg/injection, about 2.2 µg/injection, about 2.3 µg/injection, about 2.4 µg/injection, about 2.5 µg/injection, about 2.6 µg/injection, about 2.7 µg/injection, about 2.8 µg/injection, about 2.9 µg/injection, about 3.0 µg/injection, about 3.1 µg/injection, about 3.2 µg/injection, about 3.3 µg/injection, about 3.4 µg/injection, about 3.5 µg/injection, about 3.6 µg/injection, about 3.7 µg/injection, about 3.8 µg/injection, about 3.9 µg/injection, about 4.0 µg/injection, about 4.1 µg/injection, about 4.2 µg/injection, about 4.3 µg/injection, about 4.4. µg/injection, about 4.5 µg/injection, about 4.6 µg/injection, about 4.7 µg/injection, about 4.8 µg/injection, about 4.9 µg/injection, about 5.0 µg/injection, about 5.1 µg/injection, about 5.2 µg/injection, about 5.3 µg/injection, about 5.4 µg/injection, about 5.5 µg/injection, about 5.6 µg/injection, about 5.7 µg/injection, about 5.8 µg/injection, about 5.9 µg/injection, about 6.0 µg/injection, about 6.1 µg/injection, about 6.2 µg/injection, about 6.3 µg/injection, about 6.4 µg/injection, about 6.5 µg/injection, about 6.6 µg/injection, about 6.7 µg/injection, about 6.8 µg/injection, about 6.9 µg/injection, about 7.0 µg/injection, about 7.1 µg/injection, about 7.2 µg/injection, about 7.3 µg/injection, about 7.4 µg/injection, about 7.5 µg/injection, about 7.6 µg/injection, about 7.7 µg/injection, about 7.8 µg/injection, about 7.9 µg/injection, about 8.0 µg/injection, about 8.1 µg/injection, about 8.2 µg/injection, about 8.3 µg/injection, about 8.4 µg/injection, about 8.5 µg/injection, about 8.6 µg/injection, about 8.7 µg/injection, about 8.8 µg/injection, about 8.9 µg/injection, about 9.0 µg/injection, about 9.1 µg/injection, about 9.2 µg/injection, about 9.3 µg/injection, about 9.4 µg/injection, about 9.5 µg/injection, about 9.6 µg/injection, about 9.7 µg/injection, about 9.8 µg/injection, about 9.9 µg/injection or up to about 10 µg/injection.

An effective dose is delivered, i.e. a dose that increases the response of allogeneic T-cells to tumor and/or allogeneic histocompatibility antigens and results in an overall decrease of tumor cells in the individual being treated. The dose of the CpG delivered to a subject in need thereof is determined for each CpG of the present disclosure. In some aspects, the dose of the CpG can be classified in mg/injection. For example, an CpG can be administered to a subject in need thereof at a dose of 0.1 mg/injection, 0.2 mg/injection, 0.3 mg/injection, 0.4 mg/injection, 0.5 mg/injection, 0.6 mg/injection, 0.7 mg/injection, 0.8 mg/injection, 0.9 mg/injection, 1.0 mg/injection, 1.1. mg/injection, 1.2 mg/injection, 1.3 mg/injection, 1.4 mg/injection, 1.5 mg/injection, 1.6 mg/injection, 1.7 mg/injection, 1.8 mg/injection, 1.9 mg/injection, 2.0 mg/injection, 2.1 mg/injection, 2.2 mg/injection, 2.3 mg/injection, 2.4 mg/injection, 2.5 mg/injection, 2.6 mg/injection, 2.7 mg/injection, 2.8 mg/injection, 2.9 mg/injection, 3.0 mg/injection, 3.1 mg/injection, 3.2 mg/injection, 3.3 mg/injection, 3.4 mg/injection, 3.5 mg/injection, 3.6 mg/injection, 3.7 mg/injection, 3.8 mg/injection, 3.9 mg/injection, 4.0 mg/injection, 4.1 mg/injection, 4.2 mg/injection, 4.3 mg/injection, 4.4. mg/injection, 4.5 mg/injection, 4.6 mg/injection, 4.7 mg/injection, 4.8 mg/injection, 4.9 mg/injection, 5.0 mg/injection, 5.1 mg/injection, 5.2 mg/injection, 5.3 mg/injection, 5.4 mg/injection, 5.5 mg/injection, 5.6 mg/injection, 5.7 mg/injection, 5.8 mg/injection, 5.9 mg/injection, 6.0 mg/injection, 6.1 mg/injection, 6.2 mg/injection, 6.3 mg/injection, 6.4 mg/injection, 6.5 mg/injection, 6.6 mg/injection, 6.7 mg/injection, 6.8 mg/injection, 6.9 mg/injection, 7.0 mg/injection, 7.1 mg/injection, 7.2 mg/injection, 7.3 mg/injection, 7.4 mg/injection, 7.5 mg/injection, 7.6 mg/injection, 7.7 mg/injection, 7.8 mg/injection, 7.9 mg/injection, 8.0 mg/injection, 8.1 mg/injection, 8.2 mg/injection, 8.3 mg/injection, 8.4 mg/injection, 8.5 mg/injection, 8.6 mg/injection, 8.7 mg/injection, 8.8 mg/injection, 8.9 mg/injection, 9.0 mg/injection, 9.1 mg/injection, 9.2 mg/injection, 9.3 mg/injection, 9.4 mg/injection, 9.5 mg/injection, 9.6 mg/injection, 9.7 mg/injection, 9.8 mg/injection, 9.9 mg/injection or up to 10 mg/injection. For another example, an CpG can be administered to a subject in need thereof at a dose of about 0.1 mg/injection, about 0.2 mg/injection, about 0.3 mg/injection, about 0.4 mg/injection, about 0.5 mg/injection, about 0.6 mg/injection, about 0.7 mg/injection, about 0.8 mg/injection, about 0.9 mg/injection, about 1.0 mg/injection, about 1.1. mg/injection, about 1.2 mg/injection, about 1.3 mg/injection, about 1.4 mg/injection, about 1.5 mg/injection, about 1.6 mg/injection, about 1.7 mg/injection, about 1.8 mg/injection, about 1.9 mg/injection, about 2.0 mg/injection, about 2.1 mg/injection, about 2.2 mg/injection, about 2.3 mg/injection, about 2.4 mg/injection, about 2.5 mg/injection, about 2.6 mg/injection, about 2.7 mg/injection, about 2.8 mg/injection, about 2.9 mg/injection, about 3.0 mg/injection, about 3.1 mg/injection, about 3.2 mg/injection, about 3.3 mg/injection, about 3.4 mg/injection, about 3.5 mg/injection, about 3.6 mg/injection, about 3.7 mg/injection, about 3.8 mg/injection, about 3.9 mg/injection, about 4.0 mg/injection, about 4.1 mg/injection, about 4.2 mg/injection, about 4.3 mg/injection, about 4.4. mg/injection, about 4.5 mg/injection, about 4.6 mg/injection, about 4.7 mg/injection, about 4.8 mg/injection, about 4.9 mg/injection, about 5.0 mg/injection, about 5.1 mg/injection, about 5.2 mg/injection, about 5.3 mg/injection, about 5.4 mg/injection, about 5.5 mg/injection, about 5.6 mg/injection, about 5.7 mg/injection, about 5.8 mg/injection, about 5.9 mg/injection, about 6.0 mg/injection, about 6.1 mg/injection, about 6.2 mg/injection, about 6.3 mg/injection, about 6.4 mg/injection, about 6.5 mg/injection, about 6.6 mg/injection, about 6.7 mg/injection, about 6.8 mg/injection, about 6.9 mg/injection, about 7.0 mg/injection, about 7.1 mg/injection, about 7.2 mg/injection, about 7.3 mg/injection, about 7.4 mg/injection, about 7.5 mg/injection, about 7.6 mg/injection, about 7.7 mg/injection, about 7.8 mg/injection, about 7.9 mg/injection, about 8.0 mg/injection, about 8.1 mg/injection, about 8.2 mg/injection, about 8.3 mg/injection, about 8.4 mg/injection, about 8.5 mg/injection, about 8.6 mg/injection, about 8.7 mg/injection, about 8.8 mg/injection, about 8.9 mg/injection, about 9.0 mg/injection, about 9.1 mg/injection, about 9.2 mg/injection, about 9.3 mg/injection, about 9.4 mg/injection, about 9.5 mg/injection, about 9.6 mg/injection, about 9.7 mg/injection, about 9.8 mg/injection, about 9.9 mg/injection or up to about 10 mg/injection.

The dose of CpG can be delivered at appropriate intervals, e.g. 1, 2, 3, or more injections at daily, semi-daily, weekly intervals concurrent with, or following radiation.

In some aspects, the dose of CpG can be delivered to subject in need thereof at appropriate intervals with at least one injection per day concurrent with radiation. In other aspects, the dose of CpG can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day concurrent with radiation. In some aspects, the dose of CpG can be delivered to subject in need thereof at appropriate intervals with at least one injection per day following radiation. In other aspects, the dose of CpG can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day following radiation.

In some aspects, the dose of CpG can be delivered to subject in need thereof at appropriate intervals with at least one injection semi-daily concurrent with radiation. In other aspects, the dose of CpG can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily concurrent with radiation. In some aspects, the dose of CpG can be delivered to subject in need thereof at appropriate intervals with at least one injection semi-daily following radiation. In other aspects, the dose of CpG can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily following radiation.

In some aspects, the dose of CpG can be delivered to subject in need thereof at appropriate intervals with at least one injection weekly concurrent with radiation. In other aspects, the dose of CpG can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly concurrent with radiation. In some aspects, the dose of CpG can be delivered to subject in need thereof at appropriate intervals with at least one injection weekly following radiation. In other aspects, the dose of CpG can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly following radiation.

The methods can further include bone marrow transplantation using at least one donor mouse of a genotype that is the same as the recipient mouse. For example, same donor and same recipient genotype could be BALB/c (H-$2^d$), DBA/2 (H-$2^d$) or C576U6 (H-$2^b$). Often, the recipient mouse can be treated with irradiation and/or ATG as described herein.

The methods can further include bone marrow transplantation using at least one donor mouse of a genotype that is different from the recipient mouse. In some aspects, the donor mouse could be BALB/c (H-$2^d$), DBA/2 (H-$2^d$) or C57BL/6 (H-$2^b$). In some aspects, the recipient mouse could be BALB/c (H-$2^d$), DBA/2 (H-$2^d$) or C57BL/6 (H-$2^b$). Often, the recipient mouse can be treated with irradiation and/or ATG as described herein.

In an exemplary aspect, mixed chimeras can be generated by injecting only $50 \times 10^6$ DBA/2 cells. In other aspects, mixed chimera can be generated by injecting $10 \times 10^6$ DBA/2 cells, $20 \times 10^6$ DBA/2 cells, $30 \times 10^6$ DBA/2 cells, $40 \times 10^6$ DBA/2 cells, $50 \times 10^6$ DBA/2 cells, $60 \times 10^6$ DBA/2 cells, $70 \times 10^6$ DBA/2 cells, $80 \times 10^6$ DBA/2 cells, $90 \times 10^6$ DBA/2 cells or $100 \times 10^6$ DBA/2 cells. In other aspects, about mixed chimera can be generated by injecting $10 \times 10^6$ DBA/2 cells, about $20 \times 10^6$ DBA/2 cells, about $30 \times 10^6$ DBA/2 cells, about $40 \times 10^6$ DBA/2 cells, about $50 \times 10^6$ DBA/2 cells, about $60 \times 10^6$ DBA/2 cells, about $70 \times 10^6$ DBA/2 cells, about $80 \times 10^6$ DBA/2 cells, about $90 \times 10^6$ DBA/2 cells or about $100 \times 10^6$ DBA/2 cells.

In an exemplary aspect, mixed chimeras can be generated by injecting only $50 \times 10^6$ C57/Bl6 cells. In other aspects, mixed chimera can be generated by injecting $10 \times 10^6$ C57/Bl6 cells, $20 \times 10^6$ C57/Bl6 cells, $30 \times 10^6$ C57/Bl6 cells, $40 \times 10^6$ C57/Bl6 cells, $50 \times 10^6$ C57/Bl6 cells, $60 \times 10^6$ C57/Bl6 cells, $70 \times 10^6$ C57/Bl6 cells, $80 \times 10^6$ C57/Bl6 cells, $90 \times 10^6$ C57/Bl6 cells or $100 \times 10^6$ C57/Bl6 cells. In other aspects, mixed chimera can be generated by injecting about $10 \times 10^6$ C57/Bl6 cells, about $20 \times 10^6$ C57/Bl6 cells, about $30 \times 10^6$ C57/Bl6 cells, about $40 \times 10^6$ C57/Bl6 cells, about $50 \times 10^6$ C57/Bl6 cells, about $60 \times 10^6$ C57/Bl6 cells, about $70 \times 10^6$ C57/Bl6 cells, about $80 \times 10^6$ C57/Bl6 cells, about $90 \times 10^6$ C57/Bl6 cells or about $100 \times 10^6$ C57/Bl6 cells.

In an exemplary aspect, complete chimeras can be generated by injecting only $50 \times 10^6$ DBA/2 spleen and marrow cells. In other aspects, mixed chimera can be generated by injecting $10 \times 10^6$ DBA/2 spleen and marrow cells, $20 \times 10^6$ DBA/2 spleen and marrow cells, $30 \times 10^6$ DBA/2 spleen and marrow cells, $40 \times 10^6$ DBA/2 spleen and marrow cells, $50 \times 10^6$ DBA/2 spleen and marrow cells, $60 \times 10^6$ DBA/2 spleen and marrow cells, $70 \times 10^6$ DBA/2 spleen and marrow cells, $80 \times 10^6$ DBA/2 spleen and marrow cells, $90 \times 10^6$ DBA/2 spleen and marrow spleen and marrow spleen and marrow cells or $100 \times 10^6$ DBA/2 spleen and marrow cells. In other aspects, complete chimeras can be generated by injecting about $10 \times 10^6$ DBA/2 spleen and marrow cells, about $20 \times 10^6$ DBA/2 spleen and marrow cells, about $30 \times 10^6$ DBA/2 spleen and marrow cells, about $40 \times 10^6$ DBA/2 spleen and marrow cells, about $50 \times 10^6$ DBA/2 spleen and marrow cells, about $60 \times 10^6$ DBA/2 spleen and marrow cells, about 70×10⁶ DBA/2 spleen and marrow cells, about 80×10⁶ DBA/2 spleen and marrow cells, about 90×10⁶ DBA/2 spleen and marrow spleen and marrow spleen and marrow cells or about 100×10⁶ DBA/2 spleen and marrow cells.

In an exemplary aspect, complete chimeras can be generated by injecting only 50×10⁶ C57/Bl6 spleen and marrow cells. In other aspects, mixed chimera can be generated by injecting 10×10⁶ C57/Bl6 spleen and marrow cells, 20×10⁶ C57/Bl6 spleen and marrow cells, 30×10⁶ C57/Bl6 spleen and marrow cells, 40×10⁶ C57/Bl6 spleen and marrow cells, 50×10⁶ C57/Bl6 spleen and marrow cells, 60×10⁶ C57/Bl6 spleen and marrow cells, 70×10⁶ C57/Bl6 spleen and marrow cells, 80×10⁶ C57/Bl6 spleen and marrow cells, 90×10⁶ C57/Bl6 spleen and marrow spleen and marrow spleen and marrow cells or 100×10⁶ C57/Bl6 spleen and marrow cells. In other aspects, about complete chimera can be generated by injecting 10×10⁶ C57/Bl6 spleen and marrow cells, about 20×10⁶ C57/Bl6 spleen and marrow cells, about 30×10⁶ C57/Bl6 spleen and marrow cells, about 40×10⁶ C57/Bl6 spleen and marrow cells, about 50×10⁶ C57/Bl6 spleen and marrow cell, about 60×10⁶ C57/Bl6 spleen and marrow cells, about 70×10⁶ C57/Bl6 spleen and marrow cells, about 80×10⁶ C57/Bl6 spleen and marrow cells, about 90×10⁶ C57/Bl6 spleen and marrow spleen and marrow spleen and marrow cells or about 100×10⁶ C57/Bl6 spleen and marrow cells.

In some aspects, the method can further include a model of tumor relapse. The tumor relapse aspect can further comprise administration of lymphoma cells, often A20 lymphoma cells, to the mouse. In some aspects, the lymphoma cells can be administered 70 days following conditioning. In other aspects, the lymphoma cells can be administered one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days or 100 days following conditioning. In other aspects, about the lymphoma cells can be administered about one day, about two days, about three days, about four days, about five days, about six days, about seven days, about eight days, about nine days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days or about 100 days following conditioning.

In other aspects, the lymphoma cells can be administered at least one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, 60 days, 61 days, 62 days, 63 days, 64 days, 65 days, 66 days, 67 days, 68 days, 69 days, 70 days, 71 days, 72 days, 73 days, 74 days, 75 days, 76 days, 77 days, 78 days, 79 days, 80 days, 81 days, 82 days, 83 days, 84 days, 85 days, 86 days, 87 days, 88 days, 89 days, 90 days, 91 days, 92 days, 93 days, 94 days, 95 days, 96 days, 97 days, 98 days, 99 days or at least 100 days following conditioning. In other aspects, about the lymphoma cells can be administered at least about one day, about two days, about three days, about four days, about five days, about six days, about seven days, about eight days, about nine days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days or at least about 100 days following conditioning.

The lymphoma cells can be injected into at least one, often two sites in the mouse. In some aspects, the lymphoma cells can be injected into one, two, three, four, five, six, seven, eight, nine or ten sites in the mouse. In some aspects, the sites include the upper flank, the lower flank, the back, the cranium, the tail vein or the like.

In some aspects, the lymphoma tumors can grow for 21 days. In other aspects, the lymphoma tumors can grow for at least one day, two days, three days, four days, five days, six days, seven days, eight days, nine days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days or at least 50 days. In other aspects, the tumors can grow until a desired size is reached, often 1 cm diameter. In some aspects, the tumors can grow until 0.2 cm, 0.4 cm, 0.6 cm, 0.8 cm, 1 cm, 1.2 cm, 1.4 cm, 1.6 cm, 1.8 cm, 2.0 cm, 2.2 cm, 2.4 cm, 2.6 cm, 2.8 cm or 3.0 cm. In some aspects, about the tumors can grow until about 0.2 cm, about 0.4 cm, about 0.6 cm, about 0.8 cm, about 1 cm, about 1.2 cm, about 1.4 cm, about 1.6 cm, about 1.8 cm, about 2.0 cm, about 2.2 cm, about 2.4 cm, about 2.6 cm, about 2.8 cm or about 3.0 cm.

The methods can further include administration of local irradiation to at least one of the tumors of the mouse. In an exemplary aspect, the tumors can be given local tumor radiation (2 daily doses of 10 Gy each), and 3 injections of 30 ug CpG days 1, 7, and 14 after radiation.

In some aspects, the local irradiation can comprise one dose, two doses, three doses, four doses, five doses, six doses, seven doses, eight doses, nine doses or 10 doses of radiation. In some aspects, the local irradiation can comprise more than one dose, two doses, three doses, four doses, five doses, six doses, seven doses, eight doses, nine doses or 10 doses of radiation.

The methods can further include administration of local irradiation to at least one of the tumors of the mouse. In some aspects, about the local irradiation can comprise about one dose, about two doses, about three doses, about four doses, about five doses, about six doses, about seven doses, about eight doses, about nine doses or about 10 doses of radiation. In some aspects, the local irradiation can comprise about more than one dose, about two doses, about three doses, about four doses, about five doses, about six doses, about seven doses, about eight doses, about nine doses or about 10 doses of radiation.

In some aspects, a dose of radiation can be 1 Gy, 2 Gy, 3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy or 20 Gy of radiation. In some aspects, a dose of radiation can be more than 1 Gy, 2 Gy, 3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy or 20 Gy of radiation.

In some aspects, a dose of radiation can be 1 Gy, about 2 Gy, 3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy or 20 Gy of radiation. In some aspects, a dose of radiation can be more than 1 Gy, about 2 Gy,3 Gy, about 4 Gy, about 5 Gy, about 6 Gy, about 7 Gy, about 8 Gy, about 9 Gy, about 10 Gy, about 11 Gy, about 12 Gy, about 13 Gy, about 14 Gy, about 15 Gy, about 16 Gy, about 17 Gy, about 18 Gy, about 19 Gy or 20 Gy of radiation.

The lower tumors were given local tumor radiation (2 daily doses of 10 Gy each), and 3 injections of 30 ug CpG days 1, 7, and 14 after radiation.

The method can further comprise administering at least one dose of radiation to a mouse using an escalated dosing scheme. For example, the radiation dose can be escalated from a total dose of 4Gy (e.g., 2×2 Gy) during one stage to 20 Gy (e.g., 2×10 Gy) during a subsequent stage to 30 Gy (e.g., 3×10 Gy) in a final stage. In some aspects, the radiation dosing scheme can include a fractionated schedule, for example 10×2 Gy over 5 days or for example 10×3 Gy over 5 days. Any dose of radiation disclosed herein can be administered to a mouse to achieve a total dose disclosed using an escalated dosing scheme as exemplified above. Also, any dose of radiation disclosed herein can be administered to a mouse where each dose disclosed is administered using an escalated dosing scheme as exemplified above. In some aspects, the total dose administered to a mouse during each stage.

An effective dose is delivered, i.e. a dose that increases the response of allogeneic T-cells to tumor and/or allogeneic histocompatibility antigens and results in an overall decrease of tumor cells in the individual being treated. The dose of the CpG delivered to a subject in need thereof is determined for each CpG of the present disclosure. In some aspects, the dose of the CpG can be classified in mg/injection. For example, an CpG can be administered to a subject in need thereof at a dose of 0.1 mg/injection, 0.2 mg/injection, 0.3 mg/injection, 0.4 mg/injection, 0.5 mg/injection, 0.6 mg/injection, 0.7 mg/injection, 0.8 mg/injection, 0.9 mg/injection, 1.0 mg/injection, 1.1. mg/injection, 1.2 mg/injection, 1.3 mg/injection, 1.4 mg/injection, 1.5 mg/injection, 1.6 mg/injection, 1.7 mg/injection, 1.8 mg/injection, 1.9 mg/injection, 2.0 mg/injection, 2.1 mg/injection, 2.2 mg/injection, 2.3 mg/injection, 2.4 mg/injection, 2.5 mg/injection, 2.6 mg/injection, 2.7 mg/injection, 2.8 mg/injection, 2.9 mg/injection, 3.0 mg/injection, 3.1 mg/injection, 3.2 mg/injection, 3.3 mg/injection, 3.4 mg/injection, 3.5 mg/injection, 3.6 mg/injection, 3.7 mg/injection, 3.8 mg/injection, 3.9 mg/injection, 4.0 mg/injection, 4.1 mg/injection, 4.2 mg/injection, 4.3 mg/injection, 4.4. mg/injection, 4.5 mg/injection, 4.6 mg/injection, 4.7 mg/injection, 4.8 mg/injection, 4.9 mg/injection, 5.0 mg/injection, 5.1 mg/injection, 5.2 mg/injection, 5.3 mg/injection, 5.4 mg/injection, 5.5 mg/injection, 5.6 mg/injection, 5.7 mg/injection, 5.8 mg/injection, 5.9 mg/injection, 6.0 mg/injection, 6.1 mg/injection, 6.2 mg/injection, 6.3 mg/injection, 6.4 mg/injection, 6.5 mg/injection, 6.6 mg/injection, 6.7 mg/injection, 6.8 mg/injection, 6.9 mg/injection, 7.0 mg/injection, 7.1 mg/injection, 7.2 mg/injection, 7.3 mg/injection, 7.4 mg/injection, 7.5 mg/injection, 7.6 mg/injection, 7.7 mg/injection, 7.8 mg/injection, 7.9 mg/injection, 8.0 mg/injection, 8.1 mg/injection, 8.2 mg/injection, 8.3 mg/injection, 8.4 mg/injection, 8.5 mg/injection, 8.6 mg/injection, 8.7 mg/injection, 8.8 mg/injection, 8.9 mg/injection, 9.0 mg/injection, 9.1 mg/injection, 9.2 mg/injection, 9.3 mg/injection, 9.4 mg/injection, 9.5 mg/injection, 9.6 mg/injection, 9.7 mg/injection, 9.8 mg/injection, 9.9 mg/injection or up to 10 mg/injection. For another example, an CpG can be administered to a subject in need thereof at a dose of about 0.1 mg/injection, about 0.2 mg/injection, about 0.3 mg/injection, about 0.4 mg/injection, about 0.5 mg/injection, about 0.6 mg/injection, about 0.7 mg/injection, about 0.8 mg/injection, about 0.9 mg/injection, about 1.0 mg/injection, about 1.1. mg/injection, about 1.2 mg/injection, about 1.3 mg/injection, about 1.4 mg/injection, about 1.5 mg/injection, about 1.6 mg/injection, about 1.7 mg/injection, about 1.8 mg/injection, about 1.9 mg/injection, about 2.0 mg/injection, about 2.1 mg/injection, about 2.2 mg/injection, about 2.3 mg/injection, about 2.4 mg/injection, about 2.5 mg/injection, about 2.6 mg/injection, about 2.7 mg/injection, about 2.8 mg/injection, about 2.9 mg/injection, about 3.0 mg/injection, about 3.1 mg/injection, about 3.2 mg/injection, about 3.3 mg/injection, about 3.4 mg/injection, about 3.5 mg/injection, about 3.6 mg/injection, about 3.7 mg/injection, about 3.8 mg/injection, about 3.9 mg/injection, about 4.0 mg/injection, about 4.1 mg/injection, about 4.2 mg/injection, about 4.3 mg/injection, about 4.4. mg/injection, about 4.5 mg/injection, about 4.6 mg/injection, about 4.7 mg/injection, about 4.8 mg/injection, about 4.9 mg/injection, about 5.0 mg/injection, about 5.1 mg/injection, about 5.2 mg/injection, about 5.3 mg/injection, about 5.4 mg/injection, about 5.5 mg/injection, about 5.6 mg/injection, about 5.7 mg/injection, about 5.8 mg/injection, about 5.9 mg/injection, about 6.0 mg/injection, about 6.1 mg/injection, about 6.2 mg/injection, about 6.3 mg/injection, about 6.4 mg/injection, about 6.5 mg/injection, about 6.6 mg/injection, about 6.7 mg/injection, about 6.8 mg/injection, about 6.9 mg/injection, about 7.0 mg/injection, about 7.1 mg/injection, about 7.2 mg/injection, about 7.3 mg/injection, about 7.4 mg/injection, about 7.5 mg/injection, about 7.6 mg/injection, about 7.7 mg/injection, about 7.8 mg/injection, about 7.9 mg/injection, about 8.0 mg/injection, about 8.1 mg/injection, about 8.2 mg/injection, about 8.3 mg/injection, about 8.4 mg/injection, about 8.5 mg/injection, about 8.6 mg/injection, about 8.7 mg/injection, about 8.8 mg/injection, about 8.9 mg/injection, about 9.0 mg/injection, about 9.1 mg/injection, about 9.2 mg/injection, about 9.3 mg/injection, about 9.4 mg/injection, about 9.5 mg/injection, about 9.6 mg/injection, about 9.7 mg/injection, about 9.8 mg/injection, about 9.9 mg/injection or up to about 10 mg/injection.

The dose of CpG can be delivered at appropriate intervals, e.g. 1, 2, 3, or more injections at daily, semi-daily, weekly intervals concurrent with, or following radiation.

In some aspects, the dose of CpG can be delivered to subject in need thereof at appropriate intervals with at least one injection per day concurrent with radiation. In other aspects, the dose of CpG can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day concurrent with radiation. In some aspects, the dose of CpG can be delivered to subject in need thereof at appropriate intervals with at least one injection per day following radiation. In other aspects, the dose of CpG can be delivered to subject in need thereof at appropriate intervals with at least two injections per day, at least three injections per day, at least four injections per day, at least five injections per day, at least six injections per day, at least seven injections per day, at least eight injections per day, at least nine injections per day or at least ten injections per day following radiation.

In some aspects, the dose of CpG can be delivered to subject in need thereof at appropriate intervals with at least one injection semi-daily concurrent with radiation. In other aspects, the dose of CpG can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily concurrent with radiation. In some aspects, the dose of CpG can be delivered to subject in need thereof at appropriate intervals with at least one injection semi-daily following radiation. In other aspects, the dose of CpG can be delivered to subject in need thereof at appropriate intervals with at least two injections semi-daily, at least three injections semi-daily, at least four injections semi-daily, at least five injections semi-daily, at least six injections semi-daily, at least seven injections semi-daily, at least eight injections semi-daily, at least nine injections semi-daily or at least ten injections semi-daily following radiation.

In some aspects, the dose of CpG can be delivered to subject in need thereof at appropriate intervals with at least one injection weekly concurrent with radiation. In other aspects, the dose of CpG can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly concurrent with radiation. In some aspects, the dose of CpG can be delivered to subject in need thereof at appropriate intervals with at least one injection weekly following radiation. In other aspects, the dose of CpG can be delivered to subject in need thereof at appropriate intervals with at least two injections weekly, at least three injections weekly, at least four injections weekly, at least five injections weekly, at least six injections weekly, at least seven injections weekly, at least eight injections weekly, at least nine injections weekly or at least ten injections weekly following radiation.

In some aspects, the tumor relapse model can be performed using mice as stable chimeras. Following HCT, the recipient can be monitored for chimerism. Recipients who exhibit greater than 95% donor cells in a given blood cell lineage by any analysis to determine chimerism at any time post-transplantation can be classified as having full donor chimerism. In some aspects, mixed chimerism can be greater than 1% donor-derived cells of a given lineage but less than 95% donor-derived DNA.

Individuals who exhibit mixed chimerism can be further classified according to the evolution of chimerism, where improving mixed chimerism can be a continuous increase in the proportion of donor cells over a period of time (e.g., at least a 6-months). In some aspects, stable mixed chimerism can include fluctuations in the percentage of recipienT-cells over time, without complete loss of donor cells.

Chimerism is defined as greater than 1% recipient DNA. In some aspects, chimerism can include a percentage of cells derived from the donor and a percentage of cells derived from the recipient. In some aspects, chimerism is more than 70% of the cells in the recipient being derived from the donor. In other aspects, chimerism is more than 10% of the cells in the recipient being derived from the donor, more than 15% of the cells in the recipient being derived from the donor, more than 20% of the cells in the recipient being derived from the donor, more than 25% of the cells in the recipient being derived from the donor, more than 30% of the cells in the recipient being derived from the donor, more than 35% of the cells in the recipient being derived from the donor, more than 40% of the cells in the recipient being derived from the donor, more than 45% of the cells in the recipient being derived from the donor, more than 50% of the cells in the recipient being derived from the donor, more than 55% of the cells in the recipient being derived from the donor, more than 56% of the cells in the recipient being derived from the donor, more than 57% of the cells in the recipient being derived from the donor, more than 58% of the cells in the recipient being derived from the donor, more than 59% of the cells in the recipient being derived from the donor, more than 60% of the cells in the recipient being derived from the donor, more than 61% of the cells in the recipient being derived from the donor, more than 62% of the cells in the recipient being derived from the donor, more than 63% of the cells in the recipient being derived from the donor, more than 64% of the cells in the recipient being derived from the donor, more than 65% of the cells in the recipient being derived from the donor, more than 66% of the cells in the recipient being derived from the donor, more than 67% of the cells in the recipient being derived from the donor, more than 68% of the cells in the recipient being derived from the donor, more than 69% of the cells in the recipient being derived from the donor, more than 70% of the cells in the recipient being derived from the donor, more than 71% of the cells in the recipient being derived from the donor, more than 72% of the cells in the recipient being derived from the donor, more than 73% of the cells in the recipient being derived from the donor, more than 74% of the cells in the recipient being derived from the donor, more than 75% of the cells in the recipient being derived from the donor, more than 76% of the cells in the recipient being derived from the donor, more than 77% of the cells in the recipient being derived from the donor, more than 78% of the cells in the recipient being derived from the donor, more than 79% of the cells in the recipient being derived from the donor, more than 80% of the cells in the recipient being derived from the donor, more than 81% of the cells in the recipient being derived from the donor, more than 82% of the cells in the recipient being derived from the donor, more than 83% of the cells in the recipient being derived from the donor, more than 84% of the cells in the recipient being derived from the donor, more than 85% of the cells in the recipient being derived from the donor, more than 86% of the cells in the recipient being derived from the donor, more than 87% of the cells in the recipient being derived from the donor, more than 88% of the cells in the recipient being derived from the donor, more than 89% of the cells in the recipient being derived from the donor, more than 90% of the cells in the recipient being derived from the donor, more than 91% of the cells in the recipient being derived from the donor, more than 92% of the cells in the recipient being derived from the donor, more than 93% of the cells in the recipient being derived from the donor, more than 94% of the cells in the recipient being derived from the donor, more than 95% of the cells in the recipient being derived from the donor, more than 96% of the cells in the recipient being derived from the donor, more than 97% of the cells in the recipient being derived from the donor, more than 98% of the cells in the recipient being derived from the donor ore more than 99% of the cells in the recipient being derived from the donor.

Chimerism can be stable following HCT. In some aspects, stable chimerism lasts for at least 6 months after HCT. In some aspects, stable chimerism can persist for more than five days, more than 10 days, more than 15 days, more than 20 days, more than 25 days, more than 30 days, more than 35 days, more than 40 days, more than 45 days, more than 50 days, more than 55 days, more than 60 days, more than 65 days, more than 70 days, more than 75 days, more than 80 days, more than 85 days, more than 90 days, more than 95 days, more than 100 days, more than 105 days, more than 110 days, more than 115 days, more than 120 days, more than 125 days, more than 130 days, more than 135 days, more than 140 days, more than 145 days, more than 150 days, more than 155 days, more than 160 days, more than 165 days, more than 170 days, more than 175 days, more than 180 days, more than 185 days, more than 190 days, more than 195 days, more than 200 days, more than 205 days, more than 210 days, more than 215 days, more than 220 days, more than 225 days, more than 230 days, more than 235 days, more than 240 days, more than 245 days, more than 250 days, more than 255 days, more than 260 days, more than 265 days, more than 270 days, more than 275 days, more than 280 days, more than 285 days, more than 290 days, more than 295 days, more than 300 days, more than 305 days, more than 310 days, more than 315 days, more than 320 days, more than 325 days, more than 330 days, more than 335 days, more than 340 days, more than 345 days, more than 350 days, more than 355 days, more than 360 days, more than 365 days, more than 370 days, more than 375 days, more than 380 days, more than 385 days, more than 390 days, more than 395 days, more than 400 days, more than 405 days, more than 410 days, more than 415 days, more than 420 days, more than 425 days, more than 430 days, more than 435 days, more than 440 days, more than 445 days, more than 450 days, more than 455 days, more than 460 days, more than 465 days, more than 470 days, more than 475 days, more than 480 days, more than 485 days, more than 490 days, more than 495 days, or more than 500 days.

Chimerism can be determined by measuring the percentage of donor cells for a single cell type within the recipient. For example, chimerism can be determined by the percentage of donor-derived granulocytes in the recipient. In some aspects, chimerism can be determined by measuring the percentage of donor cells for a plurality of cell types within the recipient. For example, chimerism can be determined by the percentage of donor-derived granulocytes, natural killer cells, B-cells and T-cells in the recipient.

In some aspects, the percentage of donor-derived granulocytes in the recipient can be measured. In some aspects, the percentage of donor-derived granulocytes can be constant in the recipient after transplantation. In other aspects, the percentage of donor-derived granulocytes can not be constant in the recipient after transplantation. In other aspects, the percentage of donor-derived granulocytes changes over time in the recipient after transplantation. For example, over a period of 60 days after transplantation, the percentage of donor-derived granulocytes in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some aspects, the percentage of donor-derived natural killer cells in the recipient can be measured. In some aspects, the percentage of donor-derived natural killer cells can be constant in the recipient after transplantation. In other aspects, the percentage of donor-derived natural killer cells can not be constant in the recipient after transplantation. In other aspects, the percentage of donor-derived natural killer cells changes over time in the recipient after transplantation. For example, over a period of 60 days after transplantation, the percentage of donor-derived natural killer cells in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some aspects, the percentage of donor-derived B-cells in the recipient can be measured. In some aspects, the percentage of donor-derived B-cells can be constant in the recipient after transplantation. In other aspects, the percentage of donor-derived B-cells can not be constant in the recipient after transplantation. In other aspects, the percentage of donor-derived B-cells change over time in the recipient after transplantation. For example, over a period of 60 days after transplantation, the percentage of donor-derived B-cells in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

In some aspects, the percentage of donor-derived T-cells in the recipient can be measured. In some aspects, the percentage of donor-derived T-cells can be constant in the recipient after transplantation. In other aspects, the percentage of donor-derived T-cells is not constant in the recipient after transplantation. In other aspects, the percentage of donor-derived T-cells change over time in the recipient after transplantation. For example, over a period of 60 days after transplantation, the percentage of donor-derived T-cells in the recipient can be at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 20%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99%.

There are a plurality of methods of testing for chimerism that are readily available and known to those of skill in the art. Any method of testing for chimerism that distinguishes donor or recipient origin of a cell is suitable for use in the methods described herein.

In some aspects, the methods of testing for chimerism can include genetic based methods. For example, polymerase chain reaction (PCR) based methods which utilize probes can be used. In some aspects, probes for PCR based methods can be probes for microsatellite analysis. For another example, commercial kits that distinguish polymorphisms in short terminal repeat lengths of donor and host origin are readily available and known to those of skill in the art.

In some aspects, major histocompatibility complex (MHC) typing can be used for testing chimerism. For example, MHC typing can be used to test the type of cells in the blood. In some aspects, MHC typing can be used in combination with flow cytometry. In some aspect, an analysis of HLA-stained cells by flow cytometry can be performed.

The methods described herein are provided such that a recipient can achieve stable chimerism sufficient to allow withdrawal of immunosuppressive drugs. For example, withdrawal of immunosuppressive drugs can include tapering immunosuppressive drugs. In other aspects, withdrawal of immunosuppressive drugs can include immediate withdrawal of immunosuppressive drugs. In some aspects, stable chimerism persists for at least six months prior to withdrawal of immunosuppressive drugs. In other aspects, mixed chimerism persists for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some aspects, a lack of rejection episodes can coincide with chimerism prior to withdrawal of immunosuppressive drugs. In some aspects, a lack of rejection episodes can be consistent for at least six months prior to withdrawal of immunosuppressive drugs. In other aspects, a lack of rejection episodes can be consistent for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In some aspects, a lack of GVHD and lack of rejection episodes coincides with chimerism prior to withdrawal of immunosuppressive drugs. In some aspects, a lack of GVHD and lack of rejection episodes can be consistent for at least six months prior to withdrawal of immunosuppressive drugs. In other aspects, a lack of GVHD and lack of rejection episodes can be consistent for at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months. In some aspects, the dose of the adjuvant can slowly be tapered providing the recipient meets clinical criteria for lack of rejection and GVHD. For example, the total amount of the adjuvant administered can be reduced over time. In some aspects, tapering of the adjuvant can occur for a duration of at least one month, two months, three months, four months, five months, six months, seven months, eight months, nine months, ten months, 11 months, 12 months, 13 months, 14 months, 15 months, 16 months, 17 months, 18 months, 19 months, 20 months, 21 months, 22 months, 23 months or at least 24 months.

In order to determine if tapering of the immunosuppressive regimen is appropriate for the recipient, the recipient can be tested for chimerism, usually at regular intervals. For example, regular intervals can be monthly, semi-monthly, weekly, bi-monthly, annually, bi-annually or the like.

The methods of the mouse model may further comprise monitoring the immune cell infiltrates in the local and distant tumors before and after treatment, and the immune response of donor blood T-cells after treatment to stimulation with tumor cells in vitro as measured by proliferation, effector molecule expression, and cytokine secretion. In some aspects, the mouse model may further comprise monitoring the onset and progression of GVHD as described herein, and the ability of T-cells from recipients in remission to transfer anti-tumor immunity to adoptive hosts bearing the A20 lymphoma.

For example, T-cells can be isolated from the blood and the spleen. In some aspects, the T-cells can be stimulated in vitro with tumor cells, often A20 tumor cells, and proliferation, IFNγ secretion and granzyme B and perforin expression can be measured using methods known to one of ordinary skill in the art.

In addition, the method further comprises transfer and administration of chimeric DBA/2 or C57BL/6 cells to irradiated, often total body irradiated, DBA/2 or C57BL/6 hosts. Often, the hosts can be injected with T-cell depleted DBA/2 or C57BL/6 marrow cells. In some aspects, A20 tumor cells can be included.

The method may further comprise analysis of tumor infiltrating lymphocyte (TIL) using any method known to one of ordinary skill in the art, for example, immunofluorescent staining. In some aspects, the immunofluorescent staining may comprise determining the percentage of $CD4^+$ $CD25^-$, $CD8^+$, $CD4^+$, $CD25^+FoxP3^+$ and $PD-1^+$ cells in the TIL population.

Clinical Efficacy and Response Rate

The methods described herein can include inhibiting cellular and molecular targets wherein biological end points and surrogate markers can be used to determine outcome. In some aspects, the outcomes of a clinical trial may be determined. In some aspects, the outcomes can include monitoring tumor growth and disease progression during treatment of cancer. In other aspects, the outcomes can include monitoring tumor growth and disease progression and after treatment of cancer. Often, clinical efficacy can be measured by any method known in the art, using an endpoint appropriate for the cancer being treated using the methods described herein. Clinical trial end points can include, for example, survival rate, tumor size and/or number of tumors. In some aspects, improvement in survival can be measured. In other aspects, improvement in disease-free survival can be measured. Often, time to progression (TTP) wherein progression includes time of remission to disease progression or wherein progression includes time of stable disease to disease progression. TTP may include all patients in a primary efficacy analysis and further, TTP can have the advantage of achieving an end point of the clinical sooner. In some aspects, TTP can be independent of crossover effects. In other aspects, TTP can be independent of second-line therapies.

Response rate can serve as evidence of antitumor activity of a treatment administered to a subject as a surrogate for clinical benefit. In some aspects, the response rate can be an early clinical trial end point that can be reached as an endpoint within 2-3 months of initiating treatment. In accordance with the methods described herein, the response criteria can be defined prospectively and applied consistently during the course of clinical studies. In some aspects, the validation of response by an independent review committee blinded to treatment assignment can be used. In some aspects, the assessment of response duration can be determined.

In some aspects, the number of tumor remissions can be monitored. Often, the time to tumor remission following a final administration of radiation and/or immunostimulant can be determined.

The type of immune cell infiltrates into tumors of subjects in accordance with the methods described herein can also be determined. In some aspects, the quantity of immune cells infiltrating a tumor in a subject can also be determined.

Often, the response of T-cells in a subject's blood to stimulation with tumor cells can be determined, for example the response can be measured by proliferation, effector molecule expression, and cytokine secretion.

The methods described herein can further include monitoring a subject for the onset, duration and severity of acute GVHD following HCT and/or administration of an immunostimulant. The methods described herein can further include monitoring a subject for the onset, duration and severity of chronic GVHD following HCT and/or administration of an immunostimulant.

The method may further comprise analysis of tumor infiltrating lymphocyte (TIL) using any method known to one of ordinary skill in the art, for example, immunofluorescent staining. In some aspects, the immunofluorescent staining may comprise determining the percentage of $CD4^+$ $CD25^-$, $CD8^+$, $CD4^+$, $CD25^+FoxP3^+$ and $PD-1^+$ cells in the TIL population.

Criteria for Progressive Disease

Progressive disease in solid tumors can be defined as tumor growth of more than 20 percent since treatment began. Tumor growth indicates that an existing tumor is enlarging or has enlarged. In some aspects, tumor growth can indicate that the tumor is spreading. Progression indicates that treatment has stopped working or has not worked. In some aspects, the criteria for progressive disease can be tumor specific. For example, in NHL, progressive disease can be defined as any new lesion or increase of 50% or more of previously involved sites from nadir. For another example, Hodgkins disease can be evaluated by Deauville criteria. Criteria of progressive disease for other cancers can be defined by methods known to one of ordinary skill in the art.

Refractory cancer, or resistant cancer can be unresponsive to first and sometimes second line chemotherapy drugs, biological agents and/or radiation therapy. Refractory cancer can regress, but not to the point where the treatment is determined to be effective. In most aspects, the tumor size can remain consistent with the tumor size prior to use of the methods described herein or standard treatments known to those of ordinary skill in the art. Often, refractory cancer can be a stable disease or a progressive disease.

Remission can be defined as a decrease in or disappearance of signs and symptoms of cancer. In partial remission, some, but not all, signs and symptoms of cancer have disappeared. In complete remission, all signs and symptoms of cancer have disappeared, although cancer still can be in the body.

Partial remission, or partial response, indicates there has been a decrease in tumor size, or in the extent of cancer in the body, after treatment. The definition of "partial" is different for every cancer. In most aspects it means tumors must be reduced by more than 50 percent, and stay that way for at least six months after treatment.

A tumor can regress following use of the methods described herein, but often the tumor does not regress enough to be categorized as a partial response (e.g., the reduction of the tumor size, the tumor number or the like is greater than 50 percent). On the contrary, a tumor can increase in size, but not enough to be considered progressive disease. Such tumors, in which there is no significant change in size, are classified as stable disease.

Disease-free survival is the length of time after treatment that a person experiences a complete remission (in which cancer is not detectable in the body). Disease-free survival can also refer to the percentage of people who experience complete remission for a certain time period.

Progression-free survival can define the length of time during and after treatment that the cancer does not grow. Progression-free survival includes the amount of time patients have experienced a complete response or a partial response, as well as the amount of time patients have experienced stable disease.

The disclosure now being generally described will be more readily understood by reference to the following examples which are included merely for purposes of illustration of certain aspects and aspects of the present disclosure, and are not intended to limit the disclosure.

While preferred aspects of the present disclosure have been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein can be employed in practicing the disclosure. It is intended that the following claims define the scope of the disclosure and that methods and structures within the scope of these claims and their equivalents be covered thereby.

EXAMPLES

Example 1

Mouse Model of Lymphoma Relapse After Bone Marrow Transplantation

Figure 3A:
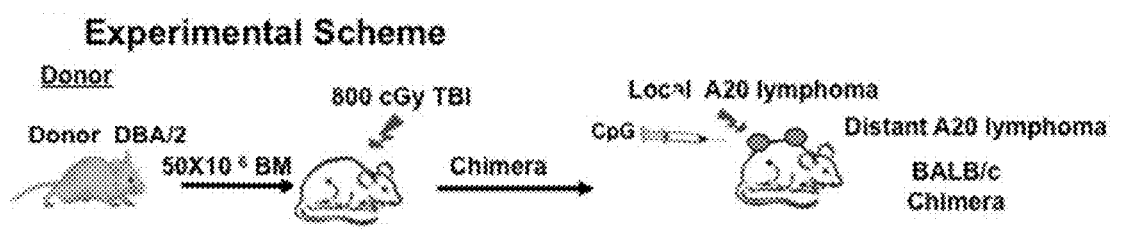
FIG. 3A-3B depicts growth of local and distant subcutaneous (sc) lymphoma tumors in chimeric and non-chimeric mice.
Figure 3B:
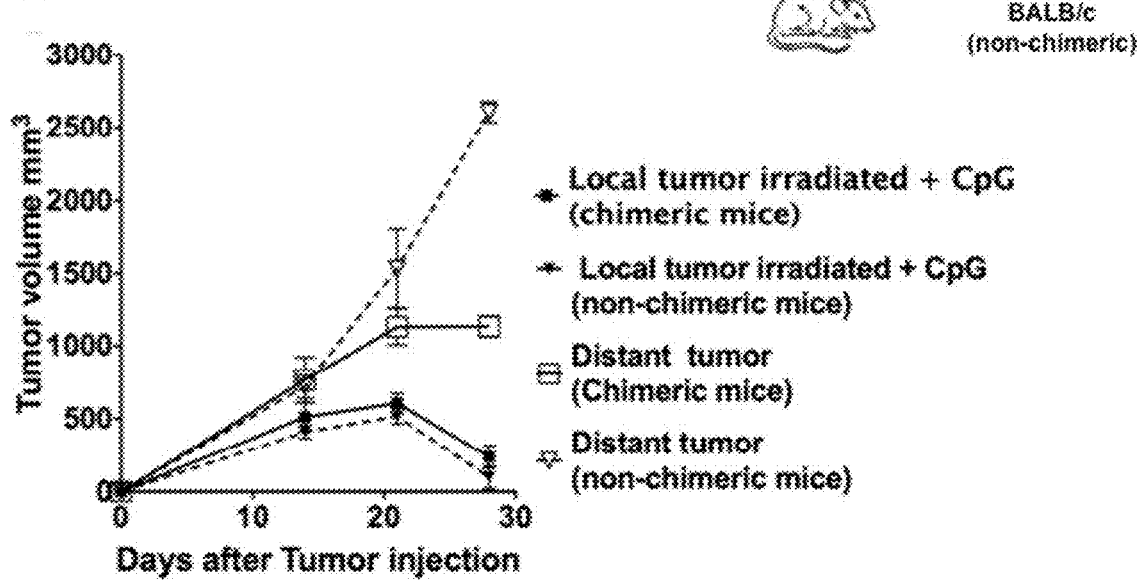

This example demonstrates a mouse model of lymphoma relapse after bone marrow transplantation. The mouse model comprises BALB/c mouse recipients with TLI/ATG as described herein, and transplanted MHC matched bone marrow cells delivered immediately after conditioning as shown in the experimental scheme in FIG. 3A. Conditioning consisted of 17 doses of 240 Gy each of TLI, and 3 doses of ATG given over 3 weeks. About 70 days later, A20 lymphoma cells were injected into two sites in the upper and lower flank. Tumors were allowed to grow for 21 days (about 1 cm diameter). The lower tumors were given local tumor radiation (2 daily doses of 10 Gy each), and 3 injections of 30 ug CpG days 1, 7, and 14 after radiation. Changes in tumor volume are shown in FIG. 3B. Control mice were untreated BALB/c recipients instead of radiation chimeras. The chimeras had about 50% donor type cells as judged by immunofluorescent staining of blood lymphocytes with the CD5.1 mAb that stains donor but not recipient T-cells. In both untreated BALB/c mice and BALB/c radiation chimeras, the lower tumors treated with radiation and CpG developed remissions and almost resolved by day 28. The upper tumors in control mice grew progressively and most mice were euthanized by day 28 due to tumor size. The growth of the upper tumors in radiation chimeras was slower than in controls, and the mean volumes were significantly lower (p<0.05) at day 28. The results suggested that local tumor treatment in chimeras slowed distant tumor growth.

Example 2

Administration of Local Tumor Irradiation and CpG Reduces Lymphoma Tumors in Mice This example demonstrates that lymphoma tumors are reduced in mice treated with local tumor irradiation and the immunostimulant CpG. For example, as shown in FIG. 1, CpG was combined with local tumor radiation to treat A20 lymphoma tumors established in chimeric recipients, after bone marrow transplantation used for lymphoma tumor relapse in mice. Two groups of BALB/c mice were used in the study depicted in FIG. 1. The control group did not receive treatment other than simultaneous rounds of subcutaneous injections of A20 lymphoma cells. The lymphoma cells were injected into the upper and the lower parts of body (flank and hind quarter, respectively) of the mouse. The mice in the experimental chimeric (allogeneic, "allo") group were given a bone marrow transplant. For the bone marrow transplant, $50 \times 10^6$ DBA/2 and MHC matched bone marrow cells were injected intravenously into lethally irradiated BALB/c mice (administered 800 rads of radiation). The latter mice became chimeric and were rested for about 2 months and then received tumor cells subcutaneously injected into the upper and the lower parts of the body. Local tumor irradiation was administered to the tumors in the lower part of the body in control and chimeric mice. The rate of local irradiation was delivered at 2 daily doses (radiation× 2), each dose of 1000 rad on day 21 and 22 after tumor growth. The local irradiation was followed by intra-tumoral injections of 30 µg of CpG within 24 hours after the final dose of radiation. CpG was further administered additionally at 7 and 14 days. The upper tumors received neither radiation nor CpG (no radiation). There were five mice were in each group. The tumor volume of all of the tumors was measured thereafter. The lower irradiated and CpG-treated tumors transitioned into remission whereas the non-radiated tumors in the flanks of the control mice grew progressively. The non-irradiated tumors in the flanks in the chimeric mice did not grow progressively. This demonstrated a systemic anti-tumor response affecting non-radiated tumors.

Example 3

Protocol for Intratumoral Injection of SD-101 and Local Radiation for Treatment of Recurrent or Progressive Lymphoma The combination of intratumoral injection of CpG and local radiation is more efficacious in tumor regression than each modality alone as demonstrated in this example. Radiation induced tumor necrosis and apoptosis, which resulted in the release of tumor antigens. The tumor antigens were processed by antigen presenting cells and generated a tumor-specific immune response that was augmented by the immunomodulatory effects of CpG injections.

Individuals selected for treatment had biopsy-confirmed relapsed, refractory, or progressive lymphoma. Two tumor sites were present—one palpable for biopsy and treatment (e.g., if >2 sites are present, the biopsy site can be different from the treatment site). One tumor site was measurable radiographically or by the modified severity-weighted assessment tool (mSWAT) assessment. The individual was more than 60 days post-allogeneic transplant for lymphoma, and had mixed (5-95%) or complete (>95%) chimerism with the allogeneic cells. For immediate disease control, patients received low dose radiation (4 Gy) locally to all bulky or symptomatic lesions on days −2 and −1.

The SD-101 oligonucleotide is a 30-mer phosphorothioate molecule of the following sequence: 5'-TCG AAC GTT CGA ACG TTC GAA CGT TCG AAT-3' (SEQ ID NO: 1). SD-101 contains juxtaposed unmethylated CpG motifs with flanking regions, in a self-complimentary palindromic sequence that is designated as a Class C-type sequence (CpG-C). The CpG-C type sequences are potent inducers of IFN-α production and B-cell proliferation.

SD-101 was administered intratumorally only to the largest palpable lesion within 24 hours after completion of radiation, on day 0. Two additional intratumoral SD-101 injections were administered to the same site on days 7 (+/−2 days) and 14 (+/−2 days). The first cohort of patients received a dose of SD-101 at 0.3 mg per injection. The dose could be escalated to 1 mg and 3 mg based on DLT. The tumor response was described by PET-CT scan imaging and/or mSWAT assessment prior to treatment, and 60 days after the first SD-101 injection to assess response.

Patient response to the treatment can be measured by various assays, including:

Mixed lymphocyte reaction: Total T-cells purified from tumors or PBMC using antibody coated microbeads were cultured for 6 days at 100,000 cells/well with either 50,000 tumor cells, 50,000 autologous dendritic cells or 50,000 each of tumor cells and dendritic cells, in 200 μl medium in round-bottom 96-well plates. The cultures were pulsed with 1 μCi/well of $^3$H-thymidine for the last 18 hours of culture. The cells were harvested by Harvester 400 (Tomtec) and radioactivity measured using a 1450 MicroBeta counter (LKB Wallac). To measure cytokines produced by the T-cells from these cultures, the T-cells were enriched from the cultures on day 6 by depleting CD11c+ cells using CD11c-PE followed by anti-PE microbeads (Miltenyi). The purified CD4+ T-cells were then washed and stimulated with 1 μg/ml anti-CD3 mAb (clone OKT, eBioscience) for 24 hours after which the supernatants were collected and assayed for specific cytokines by enzyme-linked immunosorbent assay (ELISA).

ELISA: To measure cytokines produced by tumor reactive T-cells, T-cells were enriched from the cultures on day 6 by depleting CD11c+ cells using CD11c-PE followed by anti-PE microbeads (Miltenyi). The purified T-cells were washed and stimulated with 1 μg/ml anti-CD3 mAb (clone OKT, eBioscience) for 24 hours after which the supernatants were collected and assayed for specific cytokines (IL-12, TNF-α, IFN-γ, IL-4, IL-5, IL-10, IL-13, and TGF-β) by ELISA (OptEIA, BD Biosciences for all cytokines except TGF-β (R&D).

Example 4

Treatment of Patient with Follicular NHL

In 2002, patient 1 was diagnosed with a follicular NHL, grade 2, overall stage 3A: received 6 cycles of R-CVP and achieved partial remission (PR). In March 2004 and 2008 the patient had disease recurrence with a diffuse large B-cell lymphoma. The patient received 6 cycles of rituximab, cyclophosphamide, hydroxydaunorubicin, oncovin and prednisone (R-CHOP) and 4 cycles of rituximab, ifosfamide, carboplatin, etoposide (R-ICE), respectively and achieved a PR.

In 2009, the patient received an autologous transplant following high dose conditioning with BCNU/etoposide/cyclophosphamide. Later in 2009, the patient received an allogeneic transplant from the patient's HLA-matched sibling following TLI-ATG conditioning. Post-transplant, the patient did not have GVHD. In August 2012, there was an extra-nodal lymphoma relapse with a left parotid mass measuring 4×2.5 cm, and a left lacrimal gland mass measuring 2×2 cm.

In accordance with the SD-101 protocol the patient received 4 Gy RT to the left parotid mass on day 1 and on day 11 (total RT dose=8 Gy). The patient then received the first weekly SD-101 intratumoral injection on day 12, and completed $3^{rd}$ injection two weeks later. The un-injected non-irradiated enlarged left lacrimal mass resolved. CTPET 5 months later confirmed continued complete remission. A CTPET showed an isolated recurrence in left lacrimal gland with SUV=9: therefore remission duration of 9 months Example 5

Treatment of Patient with Chronic Lymphocytic Leukemia

The second patient was a 63 year old with small lymphocytic leukemia (SLL) and high risk molecular features including Fludarabine refractory disease. In 2004, the patient was diagnosed with CLL/SLL and received 3 cycles of fludarabine, cyclophosphamide, and rituxan and had refractory disease; then received 3 cycles of R-CHOP with a poor response.

For chemo-unresponsive disease the patient received TLI-ATG conditioning and on Jul. 29, 2005, was infused with G-mobilized cells from his HLA matched sibling: the status of the patient's disease at the start of TLI was refractory with multiple enlarged PET avid LNs and 50% marrow involvement.

In February 2006: CTPET was negative (first time ever) and marrow showed 2% residual SLL consistent with near CR. In 2011, the patient had disease relapse but for personal issues deferred treatment. PET-CT imaging every 3 months confirmed steadily progressive and widespread disease.

In accordance with the SD-101 protocol, the patient received 4 Gy RT×2 to the right lower posterior cervical lymph node on day 1 and day 2, and received the 3 weekly SD-101 injections, starting day 3. The day+60 assessment by PETCT confirmed a 50% interval decrease in the size and FDG avidity of many (>7) un-injected and non-irradiated LNs and stable disease in some other LNs. On a 90 day follow up the patient remained in PR and without disease progression.

Example 6

Treatment of Patent with Mycosis Fungoides

The third patient was a 57 year-old diagnosed with stage 1B mycosis fungoides in 2011 with plaques distributed across >50% of his total body surface area.

The patient participated in a clinical trial including radiation and a drug (e.g., 12 Gy TSEBT+Zolinza) between Feb. 14, 2011-Jun. 2, 2011. The patient was randomized to the Zolinza arm, (PD). The patient received Targretin at a dose of 300 mg daily between Jun. 2, 2011-Jul. 11, 2011 and exhibtited a partial response in the skin. The Targretin was stopped due to hypertriglyceridemia. The patient also received nbUVB+topical steroids from August 2011-Oct. 23, 2011 and was at PD of tumor stage disease IIB. The patient also participated in the SGN-35 clinical trial between Nov. 15, 2011-May 15, 2012 and was in PR of the skin. The patient's term on the trial was terminated due to the decision of the clinical trial investigator due to too much toxicity. The patient then was administered Clobetasol at 0.05% in an ointment between May 16, 2012-July 2012. On Sep. 21, 2012 the patient received a combination of TLI-ATG and an allogeneic transplant from a matched sibling donor on Nov. 2, 2012: The biopsy demonstrated proven progressive disease post-transplant. In March 2013 the patient presented with progressive disease including new plaques and lesions. The patient presented with about 10% of the patient's body surface area covered with plaques for example, including the legs, some on trunk, arms and face.

In accordance with the SD-101 protocol, on day 1 and day 2, the pateint received radiation therapy for total of 8G to a single 3×3 cm plaque on the inner left thigh, followed by 3 weekly SD-101 injections starting day 3. At 6 weeks following treatment, the assessment of the patient confirmed the patient was in partial remission and only 3.25% of the patient's body surface area was covered with plaques. Finally, the assessment at 10 weeks confirmed the patient was in complete remission, and no plaques.

Example 7

Treatment of Relapsed Lymphoma in TLI/ATG Conditioned Patients Following HCT

Five patients with lymphoma relapse after allogeneic transplants combined with TLI and ATG conditioning have been treated with local tumor radiation (2×4 Gy) and intratumoral CpG from DynaVax, Inc. (SD-101). (see Table 1). Two patients achieved complete remissions as there was complete regression of all sites of disease including the un-irradiated and un-injected tumors with the duration of complete responses of at least 9 months. Two other patients had either a partial response or stable disease for around 6 months. The patient with the partial response is scheduled for retreatment with the goal of inducing a more meaningful anti-tumor response. Of the five patients treated, tumor tissue from the time of disease relapse, and blood lymphocytes from before and at designated time points after SD-101 injections was collected.

A pilot clinical trial in which patients with relapsed lymphoma after HCT with TLI/ATG conditioning were treated with local tumor radiation (2 doses of 2 Gy each) and 3 intratumoral injections of CpG (days 1,7, and 14 after radiation) to a single relapsed tumor nodule was initiated. The effect of the treatment was monitored by assessing the change in the treated tumor nodules as well as in tumor nodules at a distance by clinical examination, and PET/CT scans. Four patients developed either complete or partial remissions or stabilization of disease progression. The treatment regimen was based on previous preclinical and clinical studies that demonstrated the ability of the immunostimulatory nucleotide CpG, a TLR-9 agonist, combined with local tumor radiation to induce an anti-B-cell lymphoma immune response in patients with advanced disease who had not been given HCT.

The response to treatment in the HCT patients with tumor relapse was more robust than in the non-HCT patients. Ordinarily patients with lymphoma relapse after HCT are treated with chemotherapy with more severe side effects than tumor radiation and CpG injections, or with donor lymphocyte infusions (DLI) that can induce severe acute GVHD. Only a small minority of patients given chemotherapy or DLI develop durable complete remissions. Thus, the radiation and CpG treatment approach can improve on current therapy for relapse by reducing side effects while achieving durable complete remissions.

TABLE 1

Patient Data

| Pt | Dx | Age Sex | Therapy History | Time to Relapse (days) | CpG Dose level | History of GVHD | Immunosuppression prior to SD101 | Best response to SD101 (duration) | Adverse Events grade (≥2) | Status at last follow up time |
|---|---|---|---|---|---|---|---|---|---|---|
| 1 | FL Grade 1-2 | 58 M | R-CHOP R-ICE Autotx MRD-Allotx | 1073 | 0.3 mg | Yes | None | CR (276) | none | A:470 |
| 2 | CLL | 64 M | FCR R-CHOP URD-Allotx | 1932 | 0.3 mg | Yes | None | SD (158) | none | A:256 |
| 3 | MF | 59 M | TSEBT Vorinostat Bexarotene Brentuximab MRD-Allotx | 42 | 0.3 mg | Yes | None | CR (294) | none | A:294 |
| 4* | MZL | 54 M | CVP R-ESHAP mmURD-Allotx | 3234 | 1 mg | No | None | PR (149) | none | A:214* |

TABLE 1-continued

Patient Data

| Pt | Dx | Age Sex | Therapy History | Time to Relapse (days) | CpG Dose level | History of GVHD | Immuno-suppression prior to SD101 | Best response to SD101 (duration) | Adverse Events grade (≥2) | Status at last follow up time |
|---|---|---|---|---|---|---|---|---|---|---|
| 5 | FL DLCL | 49 F | R-CHOP, R-ICE Autotx URD-Allotx R-ICE, Gem-Ox DLI x2, R-DHAP | 275 | 1 mg | Yes | Pred 5 mg daily | PD | none | A:209 |

A = alive;
Allotx = allogeneic transplant;
Autotx = autologous transplant;
CLL = chronic lymphocytic leukemia;
CR = complete response;
DLCL = diffuse large B-cell lymphoma;
DLI = donor lymphocyte infusion;
F = female;
FL = follicular lymphoma;
GVHD = graft versus host disease;
IS = immune suppression;
M = male;
MF = mycosis fungoides;
mmURD = mismatched unrelated donor;
MRD = matched related donor;
MZL = marginal zone lymphoma;
PD = progressive disease;
PR = partial response;
Pt = patient,
SD = stable disease;
URD = unrelated donor;
* = planned for retreatment with SD101.

What is claimed:

1. A method of treating a cancer in a subject, the method comprising intratumorally administering into a tumor in the subject that has undergone an allogenic hematopoietic stem cell transplantation an immunostimulant while concurrently providing local field irradiation of the tumor in the subject's body, wherein a combination of the immunostimulant and the local field irradiation induces allogeneic immune cells to generate an anti-tumor response to HLA alloantigens expressed by the tumor, causing a systemic allogeneic anti-tumor T-cell immune response that results in tumor regression in a second, untreated site of disease in the subject's body.

2. The method of claim 1, wherein said allogeneic anti-tumor T cell immune response further comprises at least about 5% circulating allogeneic type CD3+ T cells.

3. The method of claim 1, wherein said subject has at least about 5% allogeneic type leukocytes.

4. The method of claim 1, wherein said irradiation is an irradiation at a tumor nodule.

5. The method of claim 1, wherein said irradiation is selected from the group consisting of ionizing radiation, thermal therapy, ultrasound, irreversible electroporation (IRE), oxidative stress, radiofrequency ablation and combinations thereof.

6. The method of claim 1, wherein said immunostimulant is an oligodeoxynucleotide (ODN), said ODN further comprises a CpG that binds to a Toll-Like Receptor (TLR) 9 so as to activate dendritic cells and B-cells.

7. The method of claim 1, wherein said cancer is a solid tumor or a lymphoma.

8. The method of claim 7, wherein said cancer is a lymphoma, said lymphoma is selected from the group consisting of a Non-Hodgkin's lymphoma, a Hodgkin's lymphoma, a cutaneous T-cell lymphoma and a mycosis fungoides.

9. The method of claim 1, wherein said cancer is a renal cell carcinoma.

10. The method of claim 1, wherein said cancer is selected from the group consisting of a residual cancer, a relapsed cancer and a refractory cancer.

11. The method of claim 1, wherein said second, untreated site of disease further comprises a tumor that has not been injected with said immunostimulant.

\* \* \* \* \*

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 1
tcgaacgttc gaacgttcga acgttcgaat        30

<210> SEQ ID NO 2
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 2
tccatgacgt tcctgacgtt        20